United States Patent [19]
Cochran

[11] Patent Number: 5,928,648
[45] Date of Patent: Jul. 27, 1999

[54] RECOMBINANT HERPESVIRUS OF TURKEYS AND USES THEREOF

[75] Inventor: Mark D. Cochran, Carlsbad, Calif.

[73] Assignee: Syntro Corporation, Lenexa, Kans.

[21] Appl. No.: 08/023,610

[22] Filed: Feb. 26, 1993

Related U.S. Application Data

[63] Continuation-in-part of application No. 07/898,087, Jun. 12, 1992, abandoned, and application No. 07/225,032, Jul. 27, 1988, Pat. No. 5,223,424, which is a continuation-in-part of application No. 07/078,519, Jul. 27, 1987, abandoned, application No. 06/902,887, Sep. 2, 1986, abandoned, application No. 06/823,102, Jan. 27, 1986, Pat. No. 5,068,192, and application No. 06/773,430, Sep. 6, 1985, Pat. No. 4,877,737, said application No. 08/023,610, is a continuation-in-part of application No. 07/649,380, Jan. 31, 1991, abandoned, which is a continuation of application No. 07/078,519, Jul. 27, 1987, abandoned, which is a continuation-in-part of application No. 06/933,107, Nov. 20, 1986, abandoned, application No. 06/902,877, Sep. 2, 1986, abandoned, application No. 06/887,140, Jul. 17, 1986, abandoned, application No. 06/823,102, Jan. 27, 1986, Pat. No. 5,068,192, and application No. 06/773,403, Sep. 6, 1985, Pat. No. 4,716,287, said application No. 08/023,610, is a continuation-in-part of application No. 07/914,057, Jul. 13, 1992, abandoned, which is a continuation-in-part of application No. 07/696,262, Apr. 30, 1991, abandoned, which is a continuation of application No. 06/933,107, Nov. 20, 1986, abandoned, which is a continuation-in-part of application No. 06/773,430, Sep. 6, 1985, Pat. No. 4,877,737, and application No. 06/823,102, Jan. 27, 1986, Pat. No. 5,068,192.

[51] Int. Cl.$^6$ ........................ A61K 39/255; A61K 39/295; C12N 7/01
[52] U.S. Cl. ........................ 424/199.1; 424/229.1; 435/235.1
[58] Field of Search ........................ 424/184.1, 199.1, 424/229.1, 204.1; 435/69.3, 172.3, 235.1, 236, 320.1, 252.3

[56] References Cited

U.S. PATENT DOCUMENTS

| | | |
|---|---|---|
| 4,877,737 | 10/1989 | Shih et al. . |
| 5,047,237 | 9/1991 | Cochran . |
| 5,171,677 | 12/1992 | Sakaguchi et al. . |
| 5,187,087 | 2/1993 | Sondermeijer et al. . |
| 5,223,424 | 6/1993 | Cochran et al. . |
| 5,225,336 | 7/1993 | Paoletti ........................ 435/69.1 |
| 5,240,703 | 8/1993 | Cochran . |
| 5,252,717 | 10/1993 | Velicer et al. . |
| 5,266,489 | 11/1993 | Rey-Senelonge et al. . |
| 5,686,287 | 11/1997 | Baxendale ........................ 435/235.1 |

FOREIGN PATENT DOCUMENTS

| | | |
|---|---|---|
| 0431668 | 6/1991 | European Pat. Off. . |
| 447303 | 9/1991 | European Pat. Off. . |
| 473210 | 3/1992 | European Pat. Off. . |
| 477056 | 3/1992 | European Pat. Off. . |
| 486106 | 5/1992 | European Pat. Off. . |
| WO 8807088 | 9/1988 | WIPO . |
| WO 8901040 | 2/1989 | WIPO . |
| 9002803 | 3/1990 | WIPO . |
| WO 9002802 | 3/1990 | WIPO . |
| WO 9203554 | 3/1992 | WIPO . |
| 92/15672 | 9/1992 | WIPO ........................ C12N 7/00 |
| WO 9215672 | 9/1992 | WIPO . |

OTHER PUBLICATIONS

Cantello, J., et al. (1991) "Isolation of a Marek's Disease Virus (MDV) Recombinant Containing the lacZ Gene of *Escherichia coli*", J. Virology 65:1584–1588.

Chen, X., et al. (1992) "Identification of a Unique Marek's Disease Virus Gene Which Encodes a 38–Kilodalton Phosphoprotein and Is Expressed in both Lytically Infected Cells and Latently Infected Lymphoblastoid Tumor Cells", J. Virology 66:85–94.

Gibbs, C., et al. (1984) "Extensive Homology Exists between Marek Disease Herpesvirus and its Vaccine Virus, Herpesvirus of Turkeys", Proc. Natl. Acad. Sci. USA 81:3365–3369.

Igarashi, T., et al. (1987) "Restriction Enzyme Map of Herpesvirus of Turkey DNA and Its Collinear Relationship with Marek's Disease Virus DNA", Virology 157:351–358.

Kaschka–Dierich, C., et al. (1979) "No Homology Detectable between Marek's Disease Virus (MDV) DNA and Herpesvirus of the Turkey (HVT) DNA", Med. Microbiol. Immunol. 165:223–239.

Kato, A., et al. (1989) "Homologies between Herpesvirus of Turkey and Marek's Disease Virus Type–1 DNAs within Two Co–linearly Arranged Open Reading Frames, One Encoding Glycoprotein A", Gene 84:399–405.

Lee, Y–S., et al. (1979) "Minor DNA Homology between Herpesvirus of Turkey and Marek's Disease Virus?", Virology 93:277–280.

Morgan, R., et al. (1992) "Protection of Chickens from Newcastle and Marek's Diseases with a Recombinant Herpesvirus of Turkeys Vaccine Expressing the Newcastle Disease Virus Fusion Protein", Avian Diseases 36:858–870.

Ross, L., et al. (1991) "DNA Sequence and Organization of Genes in a 5.5 kbp EcoRI Fragment Mapping in the Short Unique Segment of Marek's Disease Virus (Strain RB1B)", J. General Virology 72:949–954.

(List continued on next page.)

Primary Examiner—Mary E. Mosher
Attorney, Agent, or Firm—John P. White; Cooper & Dunham LLP

[57] ABSTRACT

The present invention relates to a recombinant herpesvirus of turkeys comprises foreign DNA inserted into a site in the herpesvirus of turkeys genome which is not essential for replication of the herpesvirus of turkeys. The invention further relates to homology vectors which produce recombinant herpesvirus of turkeys by inserting foreign DNA into herpesvirus of turkeys genome. Genetically-engineered virus S-FPV-062 is described in the Materials and Methods section which follows. One advantage of recombinant HVT as live vaccines is that they may be engineered to express only a limited number of antigens that are needed to confer protective immunity to the corresponding pathogens. Consequently, host animals vaccinated with the recombinant HVT can be distinguished from those which have been infected with the wild type virus by the absence of antigens that are normally present in the wild type virus.

7 Claims, 20 Drawing Sheets

OTHER PUBLICATIONS

Ross, L., et al. (1991) "Properties and Evolutionary Relationships of the Marek's Disease Virus Homologues of Protein Kinase, Glycoprotein D and Glycoprotein I of Herpes Simplex Virus", J. General Virology 72:939–947.

Weber, P., et al. (1987) "Rapid Identification of Nonessential Genes of Herpes Simplex Virus Type 1 by Tn5 Mutagenesis", Science 236:576–579.

Reilly, David J. and Silva, Robert F. (1993) "Cosmid library of the turkey herpesvirus genome constructed from nanogram quantities of viral DNA associated wiyj an excess of cellular DNA", J. Virological 41:323–332 (Exhibit 3).

Sondermeijer, Paul J.A. et al. (1993) "Avian herpesvirus as a live viral vector for the expression of heterologous antigens", Vaccine, vol. 11, Issue 3 (Exhibit 4).

Ross, L.J.N., et al. (1993) "Construction and properties of a turkey herpesvirus recombinant expressing the Marek's disease virus homologue of glycoprotein B of herpes simplex virus", 7 J.Virology 74, 371–377 (Exhibit 5).

Scott, Simon D., et al. (1993) "Identification and sequence analysis of the homologues of the herpes simplex virus type 1 glycoprotein H in Marek's disease virus and the herpesvirus of turkeys", J.Virology 74, 1185–1190 (Exhibit 6).

Marshall, D.R., et al. (1993) "Selection of Marek's Disease Virus Recombinants Expressing the *Escherichia coli* gpt Gene", Virology 195, 638–648 (Exhibit 7).

Zelnik, V., et al. (1993) "The complete sequence and gene organization of the short unique region of herpesvirus of turkeys", J. Virology 74, 2151–2162 (Exhibit 8).

Morgan, Robin W., et al. (1993) "Efficacy in chickens of a herpesvirus of Turkeys Recombinant Vaccine Containing the Fusion Gene of Newcastle Disease Virus: Onset of Protection and Effect of Maternal Antibodies", Avian Diseases 37:1032–1040 (Exhibit 9).

Petrovskis, Erik A., et al. (1986) "Deletions in Vaccine Strains of Pseudorabies Virus and Their Effect on Synthesis of Glycoprotein gp63", J. Virology pp. 1166–1169 vol. 60 No.3 (Exhibit 10).

Ben–Porat, T., et al. (1986) "Role of Glycoproteins of Pseudorabies Virus in Eliciting Neutralizing Antobodies", Virology 154,325–334 (Exhibit 11).

Price, Richard W., and Khan, Atia; (1981) "Resistance of Peripheral Autonomic Neurons to In Vivo Productive Infection by Herpes Simplex Virus Mutants Deficient in Thymidine Kinase Activity", Infection and Immunity, pp. 571–580, vol.34 No.2 (Exhibit 12).

Tenser, Richard B., et al. (1983) "The Role of Pseudorabies Virus Thymidine Kinase Expression in Trigeminal Ganglion Infection", J.Gen. Virol. 64, 1369–1373 (Exhibit 13).

Lomniczi, Bela, et al. (1984) "Deletions in the Genomes of Pseudorabies Virus Vaccine Strains and Existence of Flour Isomers of the Genomes", J.Virology pp. 970–979; vol.49 No.3 (Exhibit 14).

Thomsen, Darrell R., et al. (1987) "Pseudorabies virus as a live virus vector for expression of foreign genes", Gene 57, 261–265 (Exhibit 15).

Honess, R.W., (1984) "Herpes Simplex and 'The Herpes Complex': Diverse Observations and A Unifying Hypothesis", J._Gen.Virol. 65,2077–2107 (Exhibit 16).

Cook, Margery L. and Stevens, J.G., (1976) "Latent Herpetic Infections Following Experimental Viraemia", J.Gen. Virol. 31, 75–80 (Exhibit 17).

Thompson, R.L., et al. (1983) "Physical Location of a Herpes Simplex Virus Type–1 Gene Function(s) Specifically Associated with a 10 Million–Fold Increase in HSV Neurovirulence", Virology 131,180–192 (Exhibit 18).

Fukuchi, K., et al. (1985) "The Structure of Marek disease virus DNA: The presence of unique expansion in nonpathogenic viral DNA", Proc.Natl.Acad.Sci.USA vol. 82, pp. 751–754 (Exhibit 19).

Koomey, Michael J., et al. (1984) "Deletion of DNA Sequences in a Nononcogenic Variant of Herpesvirus saimiri", J.Virol. pp. 662–665, vol.50 No. 2 (Exhibit 20).

Spaete, Richard R. and Mocarski, Edward S., (1987) "Insertion and deletion mutagenesis of the human cytomegalovirus genome", Proc.Natl.Acad.Sci.USA vol.84, pp. 7213–7217 (Exhibit 21).

Shih, Richard R. And Mocarski, Edward S., (1987) "Insertion and deletion mutagenesis of the human cytomegalovirus genome", Proc. Natl. Acad. Sci. USA vol. 84, pp. 7213–7217 (Exhibit 22).

Edwards, Stirling J., (1988) "Expression of hepatitis B virus S gene by herpes simplex virus type 1 vectors carrying $\alpha$–and $\beta$–regulates gene chimeras", Proc. Natl. Acad. Sci. USA vol. 81, pp. 5867–5870 (Exhibit 23).

Roizman, Bernard, (1983) "Bioengineering of herpes simplex virus variants for potential use as live vaccines", Cold Spring Harbor Conference on New Approaches to Virla Vaccines, pp. 275–281 (Exhibit 24).

Moss, Bernard, (1991) "Vaccinia Virus: A Tool for Research and Vaccine Development", Science 252:1662–1667 (Exhibit 25).

Weir, Jerry P., and Narayanan, P.R., (1988) "The use of $\beta$–galactosidase as a marker gene to define the regulatory sequences of the herpes simplex virus type 1 glycoprotein C gene in recombinant herpesviruses", Nucleic Acids Research 16:10627–10282 (Exhibit 26).

Meignier, Bernard, (1991) "Genetically Engineered Attenuated Herpes Simplex Viruses Viruses", Reviews of Infectious Diseases 13(Suppl II):S895–S897 (Exhibit 27).

Zuckermann, F.A. et al., (1989) "Role of Pseudorabies Virus Glycoproteins in Immune Response", Vaccination and Control of Aujeszky's Disease pp. 107–117 (Exhibit 28).

Meisner, B. Reviews of Infectious Diseases, vol. 13 (suppl. 11), pp. S895–S897, 1991.

Riviere, M. et al. Journal of Virology, vol. 66, No. 6, pp. 3424–3434, Jun. 1992.

FIGURE 2A
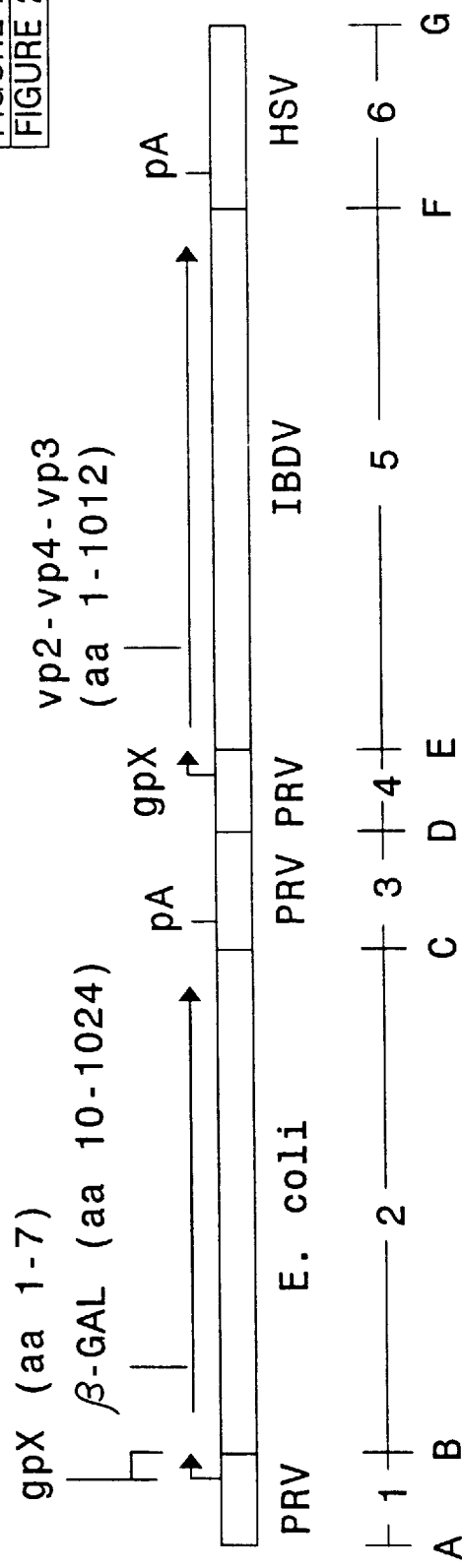
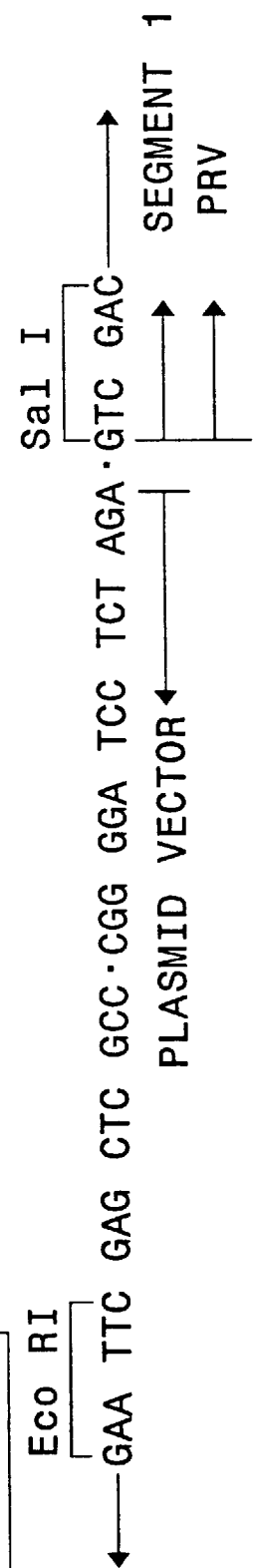

FIGURE 2C

JUNCTION D

[Kpn I]

GCG CCC ACG TGG CCT·GGT ACA ATT CGA GCT·CGC CCG GGG ATC CTC·TAG AGT CGA CTC

SEGMENT 3    SYNTHETIC DNA
PRV

[Nae I]

TAG·AGG ATC GAT CCT CTA·GAG TCG GCG GGA CGA·GCC CGC GAT

SEGMENT 4
PRV

JUNCTION E

[Alu I]    Pst I    [Bgl II]    [Sma I]

TCC ACA·GGA CCT GCA·GCG ACC CGC TTA ACA·GCG TCA ACA GCG TGC·CGC AGA TCG GGG

SEG. 4    HSV DNA    SEG. 5
PRV    IBDV

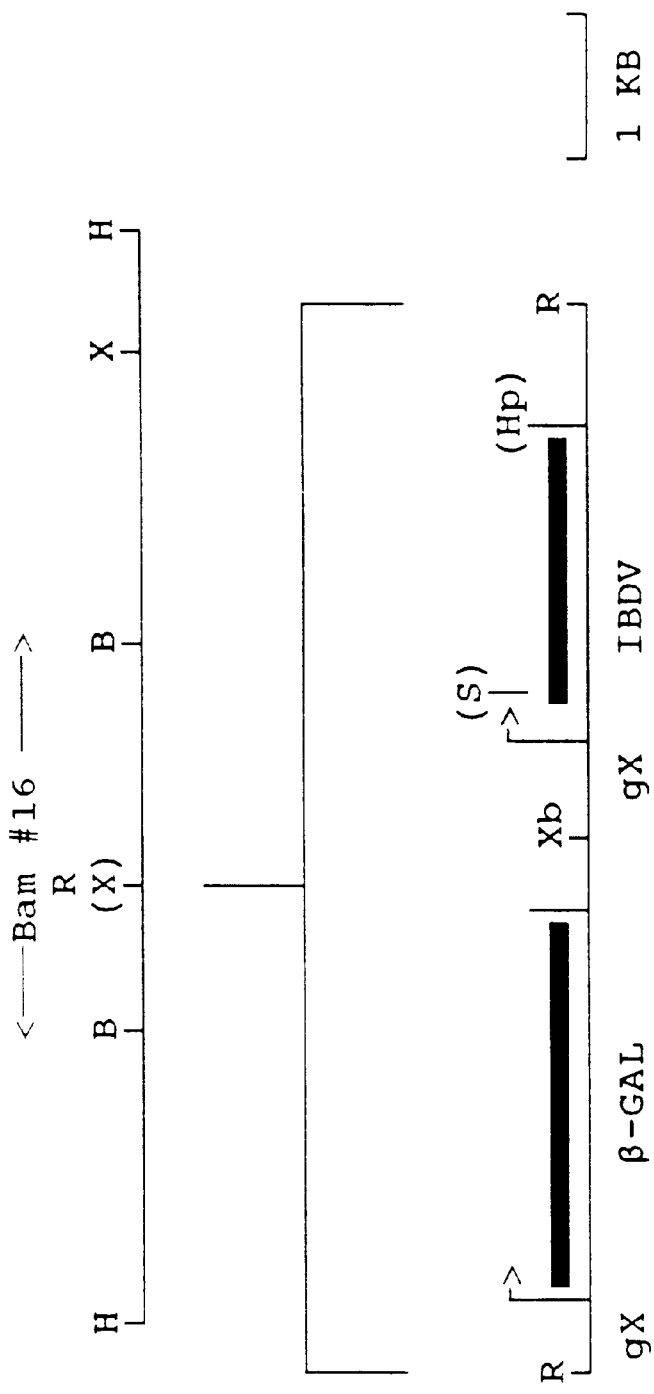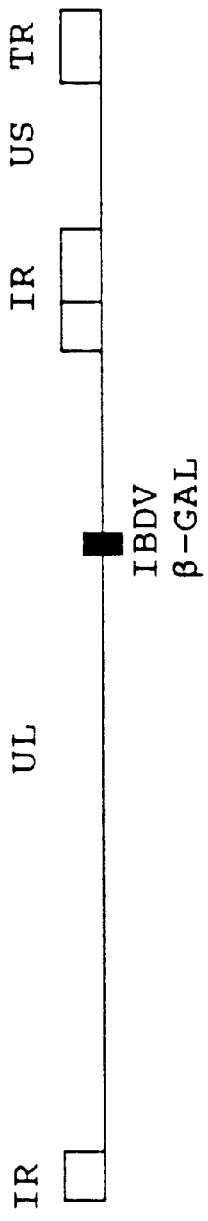
FIGURE 3A
FIGURE 3B

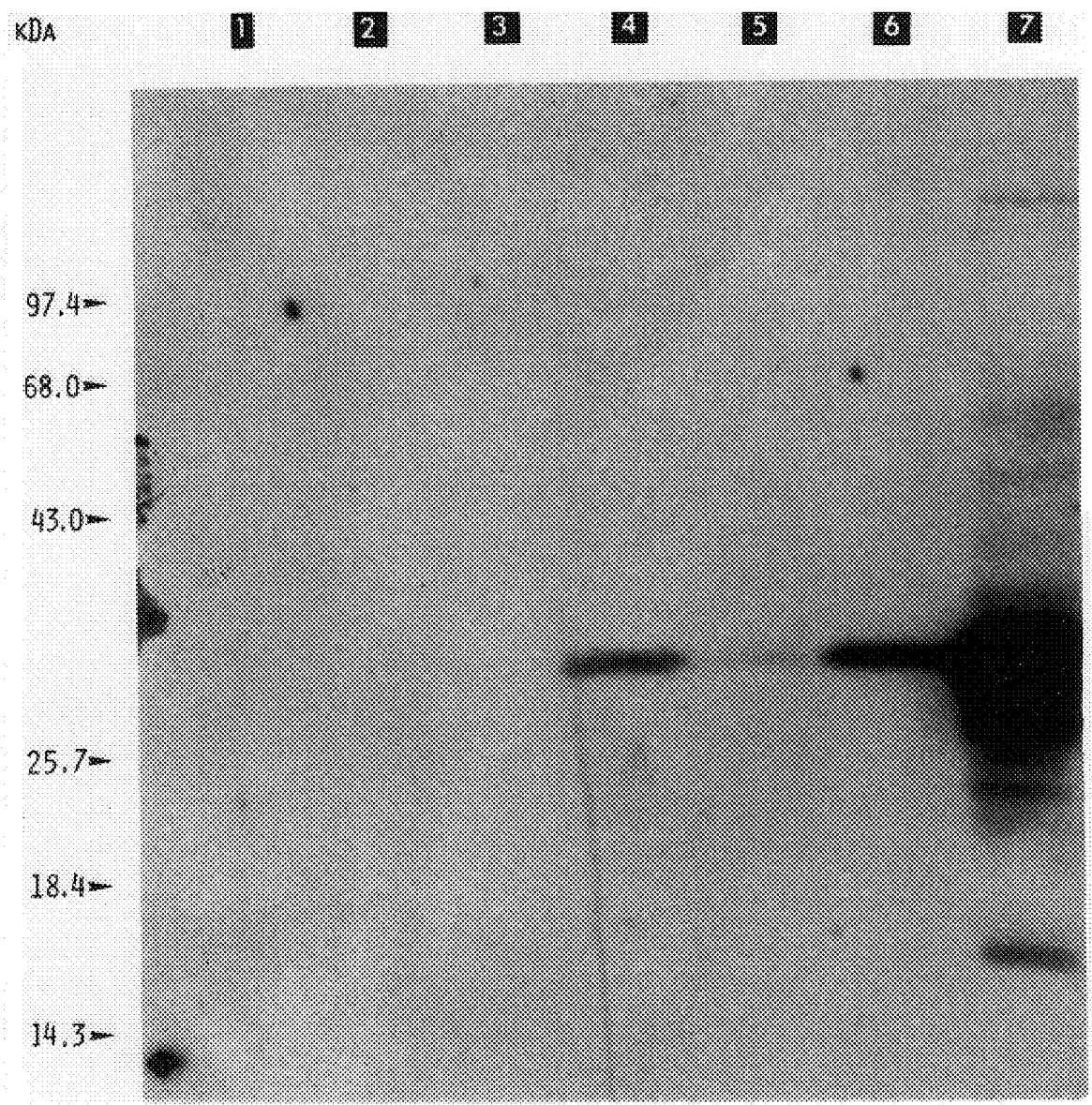

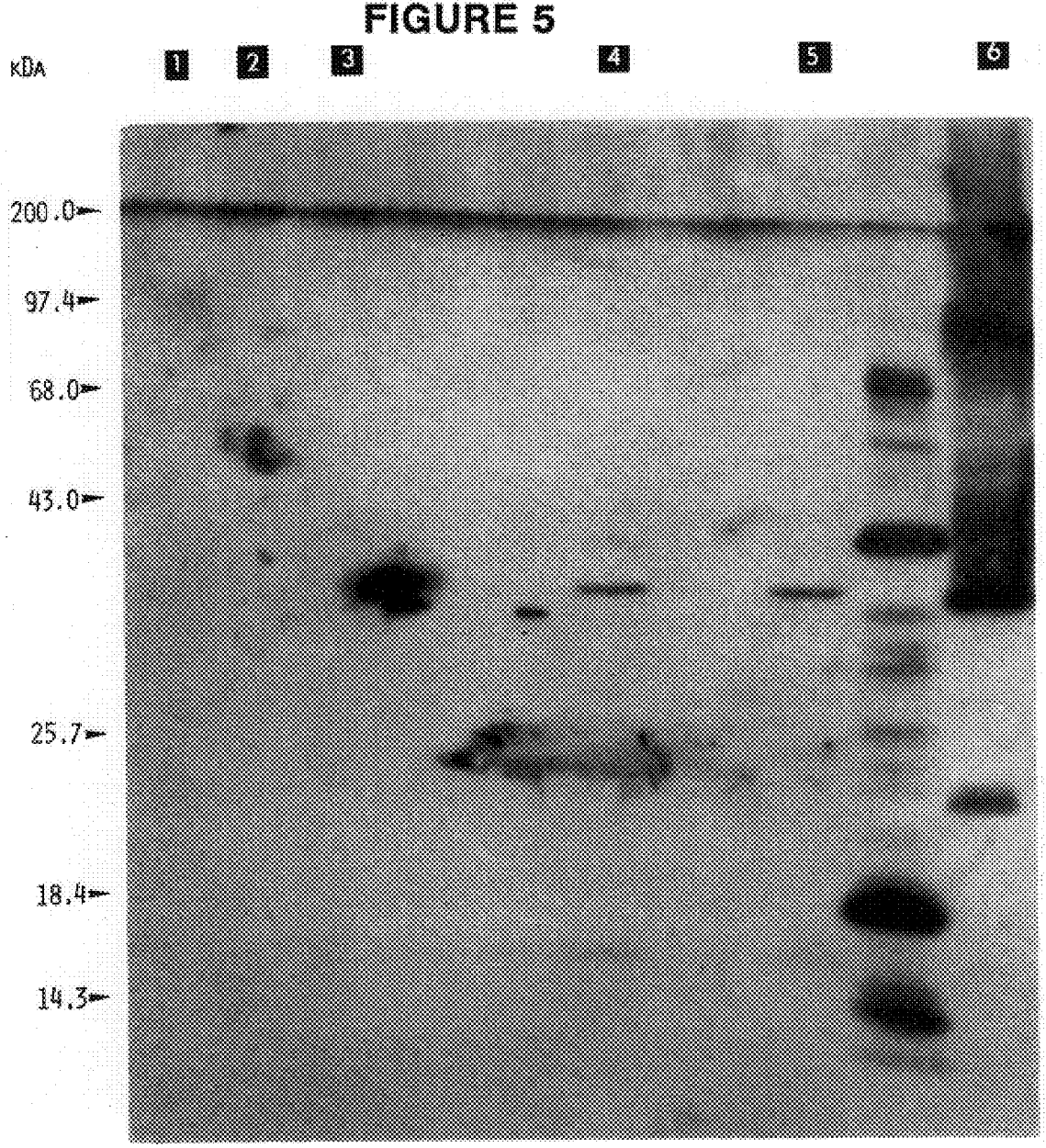

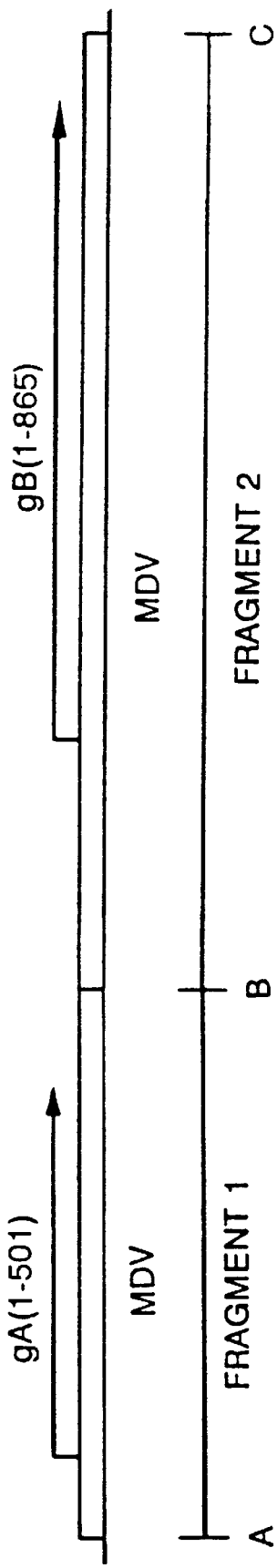

JUNC.A HindIII AAGCTTGGCCTCGTGTCGTTAATTAACCCAATTCGAGCTCGCCCAGCTTGGGCTGCAGGTCGGGAAC [SmaI]
FRAGMENT 1 / HSV-1 → ← LINKER → ← FRAG. 1 / HSV-1

JUNC.B TGTTTCAGTTAGCCTTAGCCC

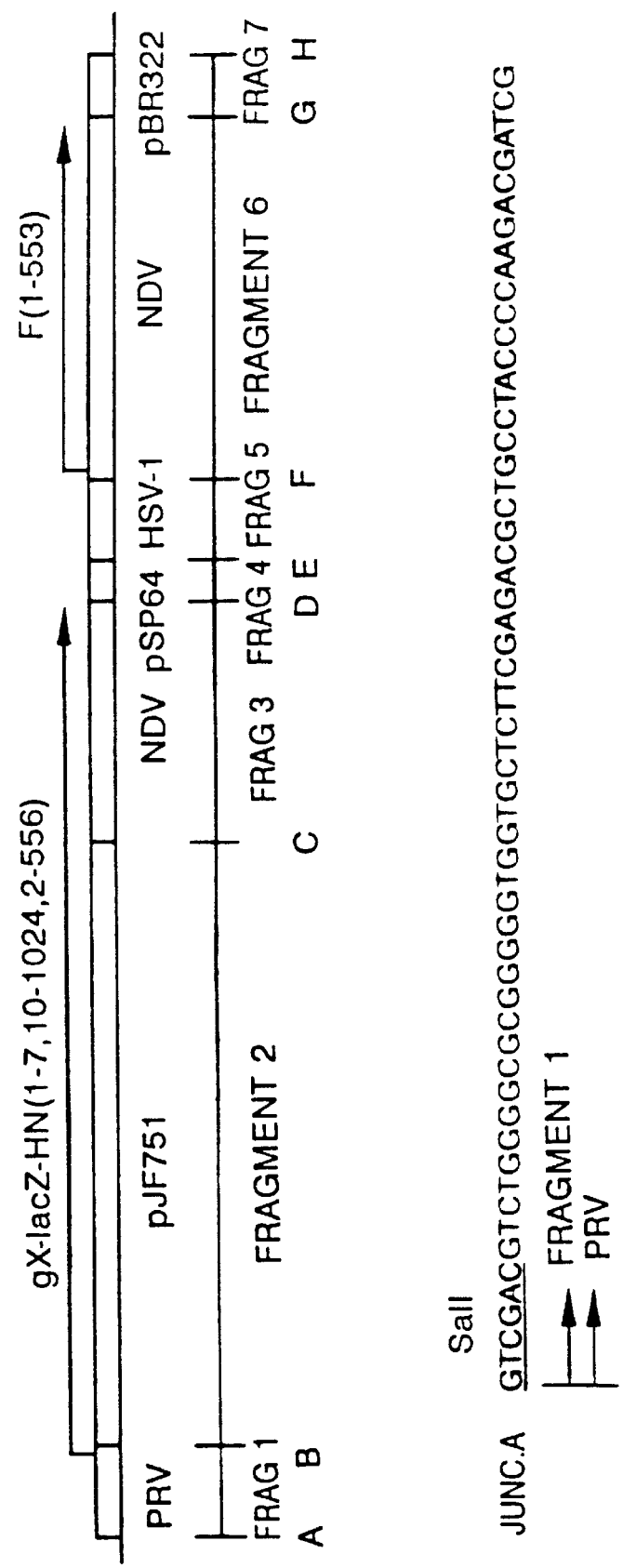

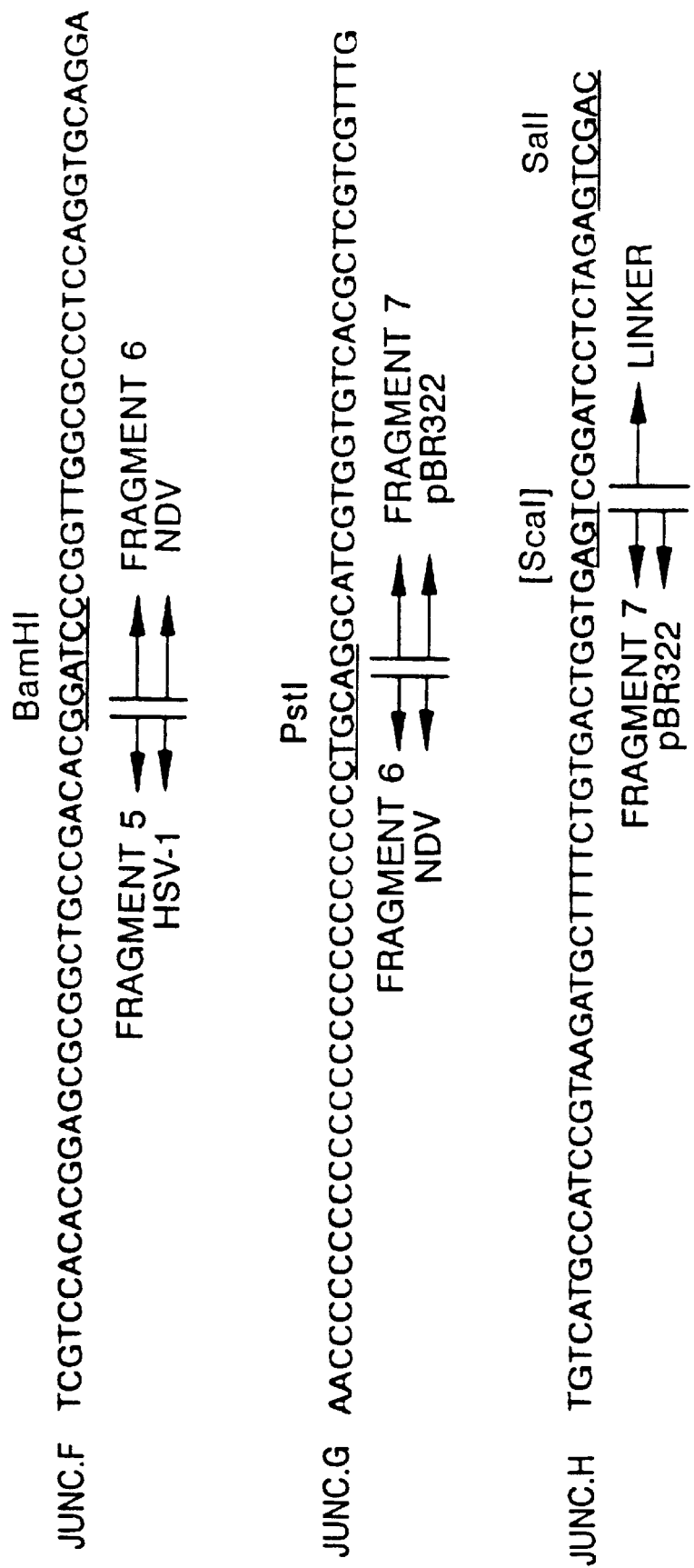

SEQUENCE LISTING (1) GENERAL INFORMATION:

(iii) NUMBER OF SEQUENCES: 47

(2) INFORMATION FOR SEQ ID NO:1:

(i) SEQUENCE CHARACTERISTICS:
    (A) LENGTH: 3350 base pairs
    (B) TYPE: nucleic acid
    (C) STRANDEDNESS: double
    (D) TOPOLOGY: linear (ii) MOLECULE TYPE: DNA (genomic)

(iii) HYPOTHETICAL: NO (iv) ANTI-SENSE: NO (ix) FEATURE:
    (A) NAME/KEY: CDS
    (B) LOCATION: 129..2522

(xi) SEQUENCE DESCRIPTION: SEQ ID NO:1:

```
GGATACGATC GGTCTGACCC GGGGGAGTCA CCCGGGGACA GCCGTCAAGG CCTTGTTCCA          60

GGATAGAACT CCTCCTTCTA CAACGCTATC ATTGATGGTC AGTAGAGATC AGACAAACGA         120

TCGCAGCG ATG ACA AAC CTG CAA GAT CAA ACC CAA CAG ATT GTT CCG TTC         170
         Met Thr Asn Leu Gln Asp Gln Thr Gln Gln Ile Val Pro Phe
           1               5                  10

ATA CGG AGC CTT CTG ATG CCA ACA ACC GGA CCG GCG TCC ATT CCG GAG          218
Ile Arg Ser Leu Leu Met Pro Thr Thr Gly Pro Ala Ser Ile Pro Glu
 15                  20                  25                  30

ACA CCC TGG AGA AGC ACA CTC TCA GGT CAG AGA CTG ACC TAC AAT TTG          266
Thr Pro Trp Arg Ser Thr Leu Ser Gly Gln Arg Leu Thr Tyr Asn Leu
                 35                  40                  45

ACT GTG GGG GAC ACA GGG TCA GGG CTA ATT GTC TTT TTC CCT GGA TTC          314
Thr Val Gly Asp Thr Gly Ser Gly Leu Ile Val Phe Phe Pro Gly Phe
             50                  55                  60

CCT GGC TCA ATT GTG GGT GCT CAC TAC ACA CTG CAG AGC AAT GGG AAC          362
Pro Gly Ser Ile Val Gly Ala His Tyr Thr Leu Gln Ser Asn Gly Asn
         65                  70                  75

TAC AAG TTC GAT CGG ATG CTC CTG ACT GCC CAG AAC CTA CCG GCC AGT          410
Tyr Lys Phe Asp Arg Met Leu Leu Thr Ala Gln Asn Leu Pro Ala Ser
     80                  85                  90

TAC AAC TAC TGC AGG CTA GTG AGT CGG AGT CTC ACA GTG AGG TCA AGC          458
Tyr Asn Tyr Cys Arg Leu Val Ser Arg Ser Leu Thr Val Arg Ser Ser
 95                 100                 105                 110

ACA CTT CCT GGT GGC GTT TAT GCA CTA AAC GGC ACC ATA AAC GCC GTG          506
Thr Leu Pro Gly Gly Val Tyr Ala Leu Asn Gly Thr Ile Asn Ala Val
                115                 120                 125

ACC TTC CAA GGA AGC CTG AGT GAA CTG ACA GAT GTT AGC TAC AAT GGG          554
Thr Phe Gln Gly Ser Leu Ser Glu Leu Thr Asp Val Ser Tyr Asn Gly
            130                 135                 140

TTG ATG TCT GCA ACA GCC AAC ATC AAC GAC AAA ATT GGG AAC GTC CTA          602
Leu Met Ser Ala Thr Ala Asn Ile Asn Asp Lys Ile Gly Asn Val Leu
        145                 150                 155

GTA GGG GAA GGG GTC ACC GTC CTC AGC TTA CCC ACA TCA TAT GAT CTT          650
Val Gly Glu Gly Val Thr Val Leu Ser Leu Pro Thr Ser Tyr Asp Leu
    160                 165                 170

GGG TAT GTG AGG CTT GGT GAC CCC ATT CCC GCA ATA GGG CTT GAC CCA          698
Gly Tyr Val Arg Leu Gly Asp Pro Ile Pro Ala Ile Gly Leu Asp Pro
175                 180                 185                 190
```

```
AAA ATG GTA GCC ACA TGT GAC AGC AGT GAC AGG CCC AGA GTC TAC ACC    746
Lys Met Val Ala Thr Cys Asp Ser Ser Asp Arg Pro Arg Val Tyr Thr
            195                 200                 205

ATA ACT GCA GCC GAT GAT TAC CAA TTC TCA TCA CAG TAC CAA CCA GGT    794
Ile Thr Ala Ala Asp Asp Tyr Gln Phe Ser Ser Gln Tyr Gln Pro Gly
        210                 215                 220

GGG GTA ACA ATC ACA CTG TTC TCA GCC AAC ATT GAT GCC ATC ACA AGC    842
Gly Val Thr Ile Thr Leu Phe Ser Ala Asn Ile Asp Ala Ile Thr Ser
                225                 230                 235

CTC AGC GTT GGG GGA GAG CTC GTG TTT CGA ACA AGC GTC CAC GGC CTT    890
Leu Ser Val Gly Gly Glu Leu Val Phe Arg Thr Ser Val His Gly Leu
    240                 245                 250

GTA CTG GGC GCC ACC ATC TAC CTC ATA GGC TTT GAT GGG ACA ACG GTA    938
Val Leu Gly Ala Thr Ile Tyr Leu Ile Gly Phe Asp Gly Thr Thr Val
255                 260                 265                 270

ATC ACC AGG GCT GTG GCC GCA AAC ACT GGG CTG ACG ACC GGC ACC GAC    986
Ile Thr Arg Ala Val Ala Ala Asn Thr Gly Leu Thr Thr Gly Thr Asp
                275                 280                 285

AAC CTT ATG CCA TTC AAT CTT GTG ATT CCA ACA AAC GAG ATA ACC CAG   1034
Asn Leu Met Pro Phe Asn Leu Val Ile Pro Thr Asn Glu Ile Thr Gln
        290                 295                 300

CCA ATC ACA TCC ATC AAA CTG GAG ATA GTG ACC TCC AAA AGT GGT GGT   1082
Pro Ile Thr Ser Ile Lys Leu Glu Ile Val Thr Ser Lys Ser Gly Gly
            305                 310                 315

CAG GCA GGG GAT CAG ATG TTA TGG TCG GCA AGA GGG AGC CTA GCA GTG   1130
Gln Ala Gly Asp Gln Met Leu Trp Ser Ala Arg Gly Ser Leu Ala Val
        320                 325                 330

ACG ATC CAT GGT GGC AAC TAT CCA GGG GCC CTC CGT CCC GTC ACG CTA   1178
Thr Ile His Gly Gly Asn Tyr Pro Gly Ala Leu Arg Pro Val Thr Leu
335                 340                 345                 350

GTG GCC TAC GAA AGA GTG GCA ACA GGA TCC GTC GTT ACG GTC GCT GGG   1226
Val Ala Tyr Glu Arg Val Ala Thr Gly Ser Val Val Thr Val Ala Gly
                355                 360                 365

GTG AGC AAC TTC GAG CTG ATC CCA AAT CCT GAA CTA GCA AAG AAC CTG   1274
Val Ser Asn Phe Glu Leu Ile Pro Asn Pro Glu Leu Ala Lys Asn Leu
        370                 375                 380

GTT ACA GAA TAC GGC CGA TTT GAC CCA GGA GCC ATG AAC TAC ACA AAA   1322
Val Thr Glu Tyr Gly Arg Phe Asp Pro Gly Ala Met Asn Tyr Thr Lys
            385                 390                 395

TTG ATA CTG AGT GAG AGG GAC CGT CTT GGC ATC AAG ACC GTC TGG CCA   1370
Leu Ile Leu Ser Glu Arg Asp Arg Leu Gly Ile Lys Thr Val Trp Pro
        400                 405                 410

ACA AGG GAG TAC ACT GAC TTT CGT GAA TAC TTC ATG GAG GTG GCC GAC   1418
Thr Arg Glu Tyr Thr Asp Phe Arg Glu Tyr Phe Met Glu Val Ala Asp
415                 420                 425                 430

CTC AAC TCT CCC CTG AAG ATT GCA GGA GCA TTC GGC TTC AAA GAC ATA   1466
Leu Asn Ser Pro Leu Lys Ile Ala Gly Ala Phe Gly Phe Lys Asp Ile
                435                 440                 445

ATC CGG GCC ATA AGG AGG ATA GCT GTG CCG GTG GTC TCC ACA TTG TTC   1514
Ile Arg Ala Ile Arg Arg Ile Ala Val Pro Val Val Ser Thr Leu Phe
        450                 455                 460

CCA CCT GCC GCT CCC CTA GCC CAT GCA ATT GGG GAA GGT GTA GAC TAC   1562
Pro Pro Ala Ala Pro Leu Ala His Ala Ile Gly Glu Gly Val Asp Tyr
            465                 470                 475

CTG CTG GGC GAT GAG GCA CAG GCT GCT TCA GGA ACT GCT CGA GCC GCG   1610
Leu Leu Gly Asp Glu Ala Gln Ala Ala Ser Gly Thr Ala Arg Ala Ala
        480                 485                 490

TCA GGA AAA GCA AGA GCT GCC TCA GGC CGC ATA AGG CAG CTG ACT CTC   1658
Ser Gly Lys Ala Arg Ala Ala Ser Gly Arg Ile Arg Gln Leu Thr Leu
495                 500                 505                 510
```

| | | |
|---|---|---|
| GCC GCC GAC AAG GGG TAC GAG GTA GTC GCG AAT CTA TTC CAG GTG CCC<br>Ala Ala Asp Lys Gly Tyr Glu Val Val Ala Asn Leu Phe Gln Val Pro<br>               515                    520                   525 | 1706 |

```
GCC GCC GAC AAG GGG TAC GAG GTA GTC GCG AAT CTA TTC CAG GTG CCC    1706
Ala Ala Asp Lys Gly Tyr Glu Val Val Ala Asn Leu Phe Gln Val Pro
            515                 520                 525

CAG AAT CCC GTA GTC GAC GGG ATT CTT GCT TCA CCT GGG GTA CTC CGC    1754
Gln Asn Pro Val Val Asp Gly Ile Leu Ala Ser Pro Gly Val Leu Arg
            530                 535                 540

GGT GCA CAC AAC CTC GAC TGC GTG TTA AGA GAG GGT GCC ACG CTA TTC    1802
Gly Ala His Asn Leu Asp Cys Val Leu Arg Glu Gly Ala Thr Leu Phe
            545                 550                 555

CCT GTG GTT ATT ACG ACA GTG GAA GAC GCC ATG ACA CCC AAA GCA TTG    1850
Pro Val Val Ile Thr Thr Val Glu Asp Ala Met Thr Pro Lys Ala Leu
            560                 565                 570

AAC AGC AAA ATG TTT GCT GTC ATT GAA GGC GTG CGA GAA GAC CTC CAA    1898
Asn Ser Lys Met Phe Ala Val Ile Glu Gly Val Arg Glu Asp Leu Gln
575                 580                 585                 590

CCT CCA TCT CAA AGA GGA TCC TTC ATA CGA ACT CTC TCT GGA CAC AGA    1946
Pro Pro Ser Gln Arg Gly Ser Phe Ile Arg Thr Leu Ser Gly His Arg
            595                 600                 605

GTC TAT GGA TAT GCT CCA GAT GGG GTA CTT CCA CTG GAG ACT GGG AGA    1994
Val Tyr Gly Tyr Ala Pro Asp Gly Val Leu Pro Leu Glu Thr Gly Arg
            610                 615                 620

GAC TAC ACC GTT GTC CCA ATA GAT GAT GTC TGG GAC GAC AGC ATT ATG    2042
Asp Tyr Thr Val Val Pro Ile Asp Asp Val Trp Asp Asp Ser Ile Met
            625                 630                 635

CTG TCC AAA GAT CCC ATA CCT CCT ATT GTG GGA AAC AGT GGA AAT CTA    2090
Leu Ser Lys Asp Pro Ile Pro Pro Ile Val Gly Asn Ser Gly Asn Leu
640                 645                 650

GCC ATA GCT TAC ATG GAT GTG TTT CGA CCC AAA GTC CCA ATC CAT GTG    2138
Ala Ile Ala Tyr Met Asp Val Phe Arg Pro Lys Val Pro Ile His Val
655                 660                 665                 670

GCT ATG ACG GGA GCC CTC AAT GCT TGT GGC GAG ATT GAG AAA GTA AGC    2186
Ala Met Thr Gly Ala Leu Asn Ala Cys Gly Glu Ile Glu Lys Val Ser
            675                 680                 685

TTT AGA AGC ACC AAG CTC GCC ACT GCA CAC CGA CTT GGC CTT AAG TTG    2234
Phe Arg Ser Thr Lys Leu Ala Thr Ala His Arg Leu Gly Leu Lys Leu
            690                 695                 700

GCT GGT CCC GGA GCA TTC GAT GTA AAC ACC GGG CCC AAC TGG GCA ACG    2282
Ala Gly Pro Gly Ala Phe Asp Val Asn Thr Gly Pro Asn Trp Ala Thr
            705                 710                 715

TTC ATC AAA CGT TTC CCT CAC AAT CCA CGC GAC TGG GAC AGG CTC CCC    2330
Phe Ile Lys Arg Phe Pro His Asn Pro Arg Asp Trp Asp Arg Leu Pro
            720                 725                 730

TAC CTC AAC CTA CCA TAC CTT CCA CCC AAT GCA GGA CGC CAG TAC CAC    2378
Tyr Leu Asn Leu Pro Tyr Leu Pro Pro Asn Ala Gly Arg Gln Tyr His
735                 740                 745                 750

CTT GCC ATG GCT GCA TCA GAG TTC AAG AGA CCC CGA ACT CGA GAG TGC    2426
Leu Ala Met Ala Ala Ser Glu Phe Lys Arg Pro Arg Thr Arg Glu Cys
            755                 760                 765

CGT CAG AGC AAT GGA AGC AGC AGC CAA CGT GGA CCC ACT ATT CCA ATC    2474
Arg Gln Ser Asn Gly Ser Ser Ser Gln Arg Gly Pro Thr Ile Pro Ile
            770                 775                 780

TGC ACT CAG TGT GTT CAT GTG GCT GGA AGA GAA TGG GAT TGT GAC TGACATG 2529
Cys Thr Gln Cys Val His Val Ala Gly Arg Glu Trp Asp Cys Asp
            785                 790                 795

AACTTCGCAC TCAGCGACCC GAACGCCCAT CGGATGCGAA ATTTTTTTGC AAACGACCAC   2589

AAGCAGGCAG CAAGTCGCAA AGGGCCAAGT ACGGGACAGC AGGCTACGGA GTGGAGGCTC   2649

GGGGCCCCCA CACCAGAGGA AGCACAGAGG GAAAAAGACA CACGGATCTC AAAGAAGATG   2709

GAGACCATGG GCATCTACTT TGCAACACCA GAATGGGTAG CACTCAATGG GCACCGAGGG   2769
```

-continued

```
CCAAGCCCCG GCCAGCTAAA GTACGGGCAG AACACACGAG AAATACGGAC CCAAACGAGG    2829

ACTATCTAGA CTACGTGCAT GCAGAGAAGA GCCGGTTGGC ATCAGAAGAA CAAATCCTAA    2889

GGGCAGCTAC GTCAGATCTA CGGGGCTCCA GGACAGGCAG AGCACCCCAA GCTTTCATAG    2949

ACGAAGTTGC CAAAGTCTAT GAAATCAACC ATGGACGTGG CCCAAACCAA GAACAGATGA    3009

AAGATCTGCT CTTGACTGCG ATGGAGATGA AGCATCGCAA TCCCAGGCGG GCTCTACCAA    3069

AGCCCAAGCC AAAACCCAAT GCTCCAACAC AGAGACCCCC TGGTCGGCTG GGGCTGGATC    3129

AGGACCGTCT CTGATGAGGA CCTTGAGTGA GGCTCCTGGG AGTCTCCCGA CAACACCCGC    3189

GCAGGTGTGG ACACAATTCG GCCTTACAAC ATCCCAAATT GGATCCGTTC GCGGGTCCCC    3249

AAAAAAAAAA AAAAAAAAAA AAAAAAAAAA AAAAAAAAAA AAAAAAAAAA AAAAAGTACC    3309

TTCTGAGGCG GAAAGAACCA GCCGGATCCC TCGAGGGATC C                        3350
```

(2) INFORMATION FOR SEQ ID NO:2:

(i) SEQUENCE CHARACTERISTICS:
        (A) LENGTH: 797 amino acids
        (B) TYPE: amino acid
        (D) TOPOLOGY: linear (ii) MOLECULE TYPE: protein (xi) SEQUENCE DESCRIPTION: SEQ ID NO:2:

```
Met Thr Asn Leu Gln Asp Gln Thr Gln Gln Ile Val Pro Phe Ile Arg
 1               5                  10                  15

Ser Leu Leu Met Pro Thr Thr Gly Pro Ala Ser Ile Pro Glu Thr Pro
                20                  25                  30

Trp Arg Ser Thr Leu Ser Gly Gln Arg Leu Thr Tyr Asn Leu Thr Val
            35                  40                  45

Gly Asp Thr Gly Ser Gly Leu Ile Val Phe Phe Pro Gly Phe Pro Gly
        50                  55                  60

Ser Ile Val Gly Ala His Tyr Thr Leu Gln Ser Asn Gly Asn Tyr Lys
65                  70                  75                  80

Phe Asp Arg Met Leu Leu Thr Ala Gln Asn Leu Pro Ala Ser Tyr Asn
                85                  90                  95

Tyr Cys Arg Leu Val Ser Arg Ser Leu Thr Val Arg Ser Ser Thr Leu
               100                 105                 110

Pro Gly Gly Val Tyr Ala Leu Asn Gly Thr Ile Asn Ala Val Thr Phe
            115                 120                 125

Gln Gly Ser Leu Ser Glu Leu Thr Asp Val Ser Tyr Asn Gly Leu Met
        130                 135                 140

Ser Ala Thr Ala Asn Ile Asn Asp Lys Ile Gly Asn Val Leu Val Gly
145                 150                 155                 160

Glu Gly Val Thr Val Leu Ser Leu Pro Thr Ser Tyr Asp Leu Gly Tyr
                165                 170                 175

Val Arg Leu Gly Asp Pro Ile Pro Ala Ile Gly Leu Asp Pro Lys Met
            180                 185                 190

Val Ala Thr Cys Asp Ser Ser Arg Pro Arg Val Tyr Thr Ile Thr
        195                 200                 205

Ala Ala Asp Asp Tyr Gln Phe Ser Ser Gln Tyr Gln Pro Gly Gly Val
       210                 215                 220

Thr Ile Thr Leu Phe Ser Ala Asn Ile Asp Ala Ile Thr Ser Leu Ser
225                 230                 235                 240

Val Gly Gly Glu Leu Val Phe Arg Thr Ser Val His Gly Leu Val Leu
                245                 250                 255
```

-continued

```
Gly Ala Thr Ile Tyr Leu Ile Gly Phe Asp Gly Thr Thr Val Ile Thr
            260                 265                 270

Arg Ala Val Ala Ala Asn Thr Gly Leu Thr Thr Gly Thr Asp Asn Leu
            275                 280                 285

Met Pro Phe Asn Leu Val Ile Pro Thr Asn Glu Ile Thr Gln Pro Ile
            290                 295                 300

Thr Ser Ile Lys Leu Glu Ile Val Thr Ser Lys Ser Gly Gly Gln Ala
305                 310                 315                 320

Gly Asp Gln Met Leu Trp Ser Ala Arg Gly Ser Leu Ala Val Thr Ile
            325                 330                 335

His Gly Gly Asn Tyr Pro Gly Ala Leu Arg Pro Val Thr Leu Val Ala
            340                 345                 350

Tyr Glu Arg Val Ala Thr Gly Ser Val Val Thr Val Ala Gly Val Ser
            355                 360                 365

Asn Phe Glu Leu Ile Pro Asn Pro Glu Leu Ala Lys Asn Leu Val Thr
            370                 375                 380

Glu Tyr Gly Arg Phe Asp Pro Gly Ala Met Asn Tyr Thr Lys Leu Ile
385                 390                 395                 400

Leu Ser Glu Arg Asp Arg Leu Gly Ile Lys Thr Val Trp Pro Thr Arg
            405                 410                 415

Glu Tyr Thr Asp Phe Arg Glu Tyr Phe Met Glu Val Ala Asp Leu Asn
            420                 425                 430

Ser Pro Leu Lys Ile Ala Gly Ala Phe Gly Phe Lys Asp Ile Ile Arg
            435                 440                 445

Ala Ile Arg Arg Ile Ala Val Pro Val Val Ser Thr Leu Phe Pro Pro
450                 455                 460

Ala Ala Pro Leu Ala His Ala Ile Gly Glu Gly Val Asp Tyr Leu Leu
465                 470                 475                 480

Gly Asp Glu Ala Gln Ala Ala Ser Gly Thr Ala Arg Ala Ala Ser Gly
            485                 490                 495

Lys Ala Arg Ala Ala Ser Gly Arg Ile Arg Gln Leu Thr Leu Ala Ala
                500                 505                 510

Asp Lys Gly Tyr Glu Val Val Ala Asn Leu Phe Gln Val Pro Gln Asn
            515                 520                 525

Pro Val Val Asp Gly Ile Leu Ala Ser Pro Gly Val Leu Arg Gly Ala
            530                 535                 540

His Asn Leu Asp Cys Val Leu Arg Glu Gly Ala Thr Leu Phe Pro Val
545                 550                 555                 560

Val Ile Thr Thr Val Glu Asp Ala Met Thr Pro Lys Ala Leu Asn Ser
            565                 570                 575

Lys Met Phe Ala Val Ile Glu Gly Val Arg Glu Asp Leu Gln Pro Pro
            580                 585                 590

Ser Gln Arg Gly Ser Phe Ile Arg Thr Leu Ser Gly His Arg Val Tyr
            595                 600                 605

Gly Tyr Ala Pro Asp Gly Val Leu Pro Leu Glu Thr Gly Arg Asp Tyr
            610                 615                 620

Thr Val Val Pro Ile Asp Asp Val Trp Asp Ser Ile Met Leu Ser
625                 630                 635                 640

Lys Asp Pro Ile Pro Pro Ile Val Gly Asn Ser Gly Asn Leu Ala Ile
            645                 650                 655

Ala Tyr Met Asp Val Phe Arg Pro Lys Val Pro Ile His Val Ala Met
            660                 665                 670

Thr Gly Ala Leu Asn Ala Cys Gly Glu Ile Glu Lys Val Ser Phe Arg
            675                 680                 685
```

```
Ser Thr Lys Leu Ala Thr Ala His Arg Leu Gly Leu Lys Leu Ala Gly
    690                 695                 700

Pro Gly Ala Phe Asp Val Asn Thr Gly Pro Asn Trp Ala Thr Phe Ile
705                 710                 715                 720

Lys Arg Phe Pro His Asn Pro Arg Asp Trp Asp Arg Leu Pro Tyr Leu
                725                 730                 735

Asn Leu Pro Tyr Leu Pro Pro Asn Ala Gly Arg Gln Tyr His Leu Ala
            740                 745                 750

Met Ala Ala Ser Glu Phe Lys Arg Pro Arg Thr Arg Glu Cys Arg Gln
        755                 760                 765

Ser Asn Gly Ser Ser Ser Gln Arg Gly Pro Thr Ile Pro Ile Cys Thr
    770                 775                 780

Gln Cys Val His Val Ala Gly Arg Glu Trp Asp Cys Asp
785                 790                 795

(2) INFORMATION FOR SEQ ID NO:3:

(i) SEQUENCE CHARACTERISTICS:
        (A) LENGTH: 5426 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION: 73..1182
        (D) OTHER INFORMATION: /product= "HVT UL42"

(ix) FEATURE:
        (A) NAME/KEY: CDS
        (B) LOCATION: 1306..2574
        (D) OTHER INFORMATION: /product= "HVT UL43"

(ix) FEATURE:
        (A) NAME/KEY: CDS
        (B) LOCATION: 2790..4259
        (D) OTHER INFORMATION: /product= "HVT gA"

(ix) FEATURE:
        (A) NAME/KEY: CDS
        (B) LOCATION: 4701..5339
        (D) OTHER INFORMATION: /product= "HVT UL45"

(xi) SEQUENCE DESCRIPTION: SEQ ID NO:3:

GGATCCGAGC TTCTACTATA CAACGCGGAC GATAATTTTG TCCACCCCAT CGGTGTTCGA         60

GAAAGGGTTT TT ATG ATG GCA GGA ATA ACT GTC GCA TGT GAC CAC ACT           108
              Met Met Ala Gly Ile Thr Val Ala Cys Asp His Thr
                1           5                  10

GCA GGA GAG GCT CAT ACA CCC GAG GAT ATG CAA AAG AAA TGG AGG ATT         156
Ala Gly Glu Ala His Thr Pro Glu Asp Met Gln Lys Lys Trp Arg Ile
         15                  20                  25

ATA TTG GCA GGG GAA AAA TTC ATG ACT ATA TCG GCA TCG TTG AAA TCG         204
Ile Leu Ala Gly Glu Lys Phe Met Thr Ile Ser Ala Ser Leu Lys Ser
     30                  35                  40

ATC GTC AGT TGT GTG AAA AAC CCC CTT CTC ACG TTT GGC GCA GAT GGG         252
Ile Val Ser Cys Val Lys Asn Pro Leu Leu Thr Phe Gly Ala Asp Gly
 45                  50                  55                  60

CTC ATT GTA CAA GGT ACT GTC TGC GGA CAG CGC ATT TTT GTT CCA ATC         300
Leu Ile Val Gln Gly Thr Val Cys Gly Gln Arg Ile Phe Val Pro Ile
             65                  70                  75
```

```
GAC CGT GAT TCC TTC AGC GAA TAT GAA TGG CAT GGG CCA ACT GCG ATG      348
Asp Arg Asp Ser Phe Ser Glu Tyr Glu Trp His Gly Pro Thr Ala Met
            80                  85                  90

TTT CTA GCA TTA ACT GAT TCC AGA CGC ACT CTT TTA GAT GCA TTC AAA      396
Phe Leu Ala Leu Thr Asp Ser Arg Arg Thr Leu Leu Asp Ala Phe Lys
            95                 100                 105

TGT GAA AAG AGA AGG GCA ATT GAC GTC TCC TTT ACC TTC GCG GGA GAG      444
Cys Glu Lys Arg Arg Ala Ile Asp Val Ser Phe Thr Phe Ala Gly Glu
        110                 115                 120

CCT CCA TGT AGG CAT TTA ATC CAA GCC GTC ACA TAC ATG ACC GAC GGT     492
Pro Pro Cys Arg His Leu Ile Gln Ala Val Thr Tyr Met Thr Asp Gly
125                 130                 135                 140

GGT TCA GTA TCG AAT ACA ATC ATT AAA TAT GAG CTC TGG AAT GCG TCT      540
Gly Ser Val Ser Asn Thr Ile Ile Lys Tyr Glu Leu Trp Asn Ala Ser
                145                 150                 155

ACA ATT TTC CCC CAA AAA ACT CCC GAT GTT ACC TTT TCT CTA AAC AAA      588
Thr Ile Phe Pro Gln Lys Thr Pro Asp Val Thr Phe Ser Leu Asn Lys
            160                 165                 170

CAA CAA TTG AAC AAA ATA TTG GCC GTC GCT TCA AAA CTG CAA CAC GAA      636
Gln Gln Leu Asn Lys Ile Leu Ala Val Ala Ser Lys Leu Gln His Glu
        175                 180                 185

GAA CTT GTA TTC TCT TTA AAA CCT GAA GGA GGG TTC TAC GTA GGA ACG      684
Glu Leu Val Phe Ser Leu Lys Pro Glu Gly Gly Phe Tyr Val Gly Thr
    190                 195                 200

GTT TGT ACT GTT ATA AGT TTC GAA GTA GAT GGG ACT GCC ATG ACT CAG      732
Val Cys Thr Val Ile Ser Phe Glu Val Asp Gly Thr Ala Met Thr Gln
205                 210                 215                 220

TAT CCT TAC AAC CCT CCA ACC TCG GCT ACC CTA GCT CTC GTA GTA GCA      780
Tyr Pro Tyr Asn Pro Pro Thr Ser Ala Thr Leu Ala Leu Val Val Ala
                225                 230                 235

TGC AGA AAG AAG AAG GCG AAT AAA AAC ACT ATT TTA ACG GCC TAT GGA      828
Cys Arg Lys Lys Lys Ala Asn Lys Asn Thr Ile Leu Thr Ala Tyr Gly
            240                 245                 250

AGT GGT AAA CCC TTT TGT GTT GCA TTG GAA GAT ACT AGT GCA TTT AGA      876
Ser Gly Lys Pro Phe Cys Val Ala Leu Glu Asp Thr Ser Ala Phe Arg
        255                 260                 265

AAT ATC GTC AAT AAA ATC AAG GCG GGT ACG TCG GGA GTT GAT CTG GGG      924
Asn Ile Val Asn Lys Ile Lys Ala Gly Thr Ser Gly Val Asp Leu Gly
    270                 275                 280

TTT TAT ACA ACT TGC GAT CCG CCG ATG CTA TGT ATT CGC CCA CAC GCA      972
Phe Tyr Thr Thr Cys Asp Pro Pro Met Leu Cys Ile Arg Pro His Ala
285                 290                 295                 300

TTT GGA AGT CCT ACC GCA TTC CTG TTT TGT AAC ACA GAC TGT ATG ACA     1020
Phe Gly Ser Pro Thr Ala Phe Leu Phe Cys Asn Thr Asp Cys Met Thr
                305                 310                 315

ATA TAT GAA CTG GAA GAA GTA AGC GCC GTT GAT GGT GCA ATC CGA GCA     1068
Ile Tyr Glu Leu Glu Glu Val Ser Ala Val Asp Gly Ala Ile Arg Ala
            320                 325                 330

AAA CGC ATC AAC GAA TAT TTC CCA ACA GTA TCG CAG GCT ACT TCC AAG     1116
Lys Arg Ile Asn Glu Tyr Phe Pro Thr Val Ser Gln Ala Thr Ser Lys
        335                 340                 345

AAG AGA AAA CAG TCG CCG CCC CCT ATC GAA AGA GAA AGG AAA ACC ACC     1164
Lys Arg Lys Gln Ser Pro Pro Pro Ile Glu Arg Glu Arg Lys Thr Thr
    350                 355                 360

AGA GCG GAT ACC CAA TAAAATGCCA GACAAACCCG GCATCCTGGT TAGAGGGCAG     1219
Arg Ala Asp Thr Gln
365                 370

GTGGGCTGGG CCAACCTTCA CGGGCGTCCG ACAGATCGGT GACACTCATA CGTTAACTAA   1279
```

```
ACGCCGGCAG CTTTGCAGAA GAAAAT ATG CCT TCC GGA GCC AGC TCG AGT CCT        1332
                             Met Pro Ser Gly Ala Ser Ser Ser Pro
                              1               5

CCA CCA GCT TAT ACA TCT GCA GCT CCG CTT GAG ACT TAT AAC AGC TGG         1380
Pro Pro Ala Tyr Thr Ser Ala Ala Pro Leu Glu Thr Tyr Asn Ser Trp
 10              15                  20                  25

CTA AGT GCC TTT TCA TGC GCA TAT CCC CAA TGC ACT GCG GGA AGA GGA         1428
Leu Ser Ala Phe Ser Cys Ala Tyr Pro Gln Cys Thr Ala Gly Arg Gly
                 30                  35                  40

CAT CGA CAA AAT GGC AAG AAG TGT ATA CGG TGT ATA GTG ATC AGT GTA         1476
His Arg Gln Asn Gly Lys Lys Cys Ile Arg Cys Ile Val Ile Ser Val
             45                  50                  55

TGT TCC TTA GTG TGC ATC GCT GCA CAT TTA GCT GTT ACC GTG TCG GGA         1524
Cys Ser Leu Val Cys Ile Ala Ala His Leu Ala Val Thr Val Ser Gly
         60                  65                  70

GTG GCA TTA ATT CCG CTT ATC GAT CAA AAC AGA GCT TAC GGA AAC TGT         1572
Val Ala Leu Ile Pro Leu Ile Asp Gln Asn Arg Ala Tyr Gly Asn Cys
     75                  80                  85

ACG GTA TGT GTA ATT GCC GGA TTC ATC GCT ACG TTT GCT GCA CGA CTT         1620
Thr Val Cys Val Ile Ala Gly Phe Ile Ala Thr Phe Ala Ala Arg Leu
 90                  95                 100                 105

ACG ATA AGA CTT TCG GAA ACG CTT ATG CTA GTG GGC AAG CCG GCG CAG         1668
Thr Ile Arg Leu Ser Glu Thr Leu Met Leu Val Gly Lys Pro Ala Gln
                110                 115                 120

TTT ATA TTT GCT ATA ATC GCT TCC GTT GCG GAA ACA CTG ATC AAT AAC         1716
Phe Ile Phe Ala Ile Ile Ala Ser Val Ala Glu Thr Leu Ile Asn Asn
            125                 130                 135

GAG GCG CTT GCC ATC AGT AAT ACT ACT TAC AAA ACT GCA TTG CGA ATA         1764
Glu Ala Leu Ala Ile Ser Asn Thr Thr Tyr Lys Thr Ala Leu Arg Ile
        140                 145                 150

ATC GAA GTA ACA TCT TTG GCG TGT TTT GTT ATG CTC GGG GCA ATA ATT         1812
Ile Glu Val Thr Ser Leu Ala Cys Phe Val Met Leu Gly Ala Ile Ile
155                 160                 165

ACA TCC CAC AAC TAT GTC TGC ATT TCA ACG GCA GGG GAC TTG ACT TGG         1860
Thr Ser His Asn Tyr Val Cys Ile Ser Thr Ala Gly Asp Leu Thr Trp
170                 175                 180                 185

AAG GGC GGG ATT TTT CAT GCT TAC CAC GGA ACA TTA CTC GGT ATA ACA         1908
Lys Gly Gly Ile Phe His Ala Tyr His Gly Thr Leu Leu Gly Ile Thr
                190                 195                 200

ATA CCA AAC ATA CAC CCA ATC CCT CTC GCG GGG TTT CTT GCA GTC TAT         1956
Ile Pro Asn Ile His Pro Ile Pro Leu Ala Gly Phe Leu Ala Val Tyr
            205                 210                 215

ACA ATA TTG GCT ATA AAT ATC GCT AGA GAT GCA AGC GCT ACA TTA TTA         2004
Thr Ile Leu Ala Ile Asn Ile Ala Arg Asp Ala Ser Ala Thr Leu Leu
        220                 225                 230

TCC ACT TGC TAT TAT CGC AAT TGC CGC GAG AGG ACT ATA CTT CGC CCT         2052
Ser Thr Cys Tyr Tyr Arg Asn Cys Arg Glu Arg Thr Ile Leu Arg Pro
235                 240                 245

TCT CGT CTC GGA CAT GGT TAC ACA ATC CCT TCT CCC GGT GCC GAT ATG         2100
Ser Arg Leu Gly His Gly Tyr Thr Ile Pro Ser Pro Gly Ala Asp Met
250                 255                 260                 265

CTT TAT GAA GAA GAC GTA TAT AGT TTT GAC GCA GCT AAA GGC CAT TAT         2148
Leu Tyr Glu Glu Asp Val Tyr Ser Phe Asp Ala Ala Lys Gly His Tyr
                270                 275                 280

TCG TCA ATA TTT CTA TGT TAT GCC ATG GGG CTT ACA ACA CCG CTG ATT         2196
Ser Ser Ile Phe Leu Cys Tyr Ala Met Gly Leu Thr Thr Pro Leu Ile
            285                 290                 295

ATT GCG CTC CAT AAA TAT ATG GCG GGC ATT AAA AAT TCG TCA GAT TGG         2244
Ile Ala Leu His Lys Tyr Met Ala Gly Ile Lys Asn Ser Ser Asp Trp
        300                 305                 310
```

-continued

| | | |
|---|---|---|
| ACT GCT ACA TTA CAA GGC ATG TAC GGG CTT GTC TTG GGA TCG CTA TCG<br>Thr Ala Thr Leu Gln Gly Met Tyr Gly Leu Val Leu Gly Ser Leu Ser<br>315                    320                   325 | 2292 |

```
ACT GCT ACA TTA CAA GGC ATG TAC GGG CTT GTC TTG GGA TCG CTA TCG      2292
Thr Ala Thr Leu Gln Gly Met Tyr Gly Leu Val Leu Gly Ser Leu Ser
315                 320                 325

TCA CTA TGT ATT CCA TCC AGC AAC AAC GAT GCC CTA ATT CGT CCC ATT      2340
Ser Leu Cys Ile Pro Ser Ser Asn Asn Asp Ala Leu Ile Arg Pro Ile
        330                 335                 340             345

CAA ATT TTG ATA TTG ATA ATC GGT GCA CTG GCC ATT GCA TTG GCT GGA      2388
Gln Ile Leu Ile Leu Ile Ile Gly Ala Leu Ala Ile Ala Leu Ala Gly
                350                 355                 360

TGT GGT CAA ATT ATA GGG CCT ACA TTA TTT GCC GCG AGT TCG GCT GCG      2436
Cys Gly Gln Ile Ile Gly Pro Thr Leu Phe Ala Ala Ser Ser Ala Ala
            365                 370                 375

ATG TCA TGT TTT ACA TGT ATC AAT ATT CGC GCT ACT AAT AAG GGT GTC      2484
Met Ser Cys Phe Thr Cys Ile Asn Ile Arg Ala Thr Asn Lys Gly Val
        380                 385                 390

AAC AAA TTG GCA GCA GCC AGT GTC GTG AAA TCT GTA CTG GGC TTC ATT      2532
Asn Lys Leu Ala Ala Ala Ser Val Val Lys Ser Val Leu Gly Phe Ile
395                 400                 405

ATT TCC GGG ATG CTT ACT TGC GTG CTA TTA CCA CTA TCG TGATAGATCG       2581
Ile Ser Gly Met Leu Thr Cys Val Leu Leu Pro Leu Ser
410                 415                 420

TCGGTCTGCG CATCGCCCAT GCTGGCGGAA CGCTCTTTCG AACCGTGAAT AAAACTTTGT    2641

ATCTACTAAA CAATAACTTT GTGTTTTATT GAGCGGTCGA AAACAATGAG GAGCTGCAAT    2701

TTAAAGCTAA CCGCATACGC CGGGCGGGTA AGACCATTT TATACCATAT TACGCATCTA     2761

TCGAAACTTG TTCGAGAACC GCAAGTAT ATG GTT TCC AAC ATG CGC GTT CTA       2813
                                Met Val Ser Asn Met Arg Val Leu
                                 1               5

CGC GTA CTG CGC CTG ACG GGA TGG GTG GGC ATA TTT CTA GTT CTG TCT      2861
Arg Val Leu Arg Leu Thr Gly Trp Val Gly Ile Phe Leu Val Leu Ser
     10                  15                  20

TTA CAG CAA ACC TCT TGT GCC GGA TTG CCC CAT AAC GTC GAT ACC CAT      2909
Leu Gln Gln Thr Ser Cys Ala Gly Leu Pro His Asn Val Asp Thr His
 25                  30                  35                  40

CAT ATC CTA ACT TTC AAC CCT TCT CCC ATT TCG GCC GAT GGC GTT CCT      2957
His Ile Leu Thr Phe Asn Pro Ser Pro Ile Ser Ala Asp Gly Val Pro
                 45                  50                  55

TTG TCA GAG GTG CCC AAT TCG CCT ACG ACC GAA TTA TCT ACA ACT GTC      3005
Leu Ser Glu Val Pro Asn Ser Pro Thr Thr Glu Leu Ser Thr Thr Val
             60                  65                  70

GCC ACC AAG ACA GCT GTA CCG ACG ACT GAA AGC ACT AGT TCC TCC GAA      3053
Ala Thr Lys Thr Ala Val Pro Thr Thr Glu Ser Thr Ser Ser Ser Glu
 75                  80                  85

GCG CAC CGC AAC TCT TCT CAC AAA ATA CCT GAT ATA ATC TGC GAC CGA      3101
Ala His Arg Asn Ser Ser His Lys Ile Pro Asp Ile Ile Cys Asp Arg
 90                  95                 100

GAA GAA GTA TTC GTA TTC CTT AAC AAT ACA GGA AGA ATT TTG TGT GAC      3149
Glu Glu Val Phe Val Phe Leu Asn Asn Thr Gly Arg Ile Leu Cys Asp
105                 110                 115                 120

CTT ATA GTC GAC CCC CCT TCA GAC GAT GAA TGG TCC AAC TTC GCT CTT      3197
Leu Ile Val Asp Pro Pro Ser Asp Asp Glu Trp Ser Asn Phe Ala Leu
                125                 130                 135

GAC GTC ACG TTC AAT CCA ATC GAA TAC CAC GCC AAC GAA AAG AAT GTA      3245
Asp Val Thr Phe Asn Pro Ile Glu Tyr His Ala Asn Glu Lys Asn Val
            140                 145                 150

GAG GTT GCC CGA GTG GCC GGT CTA TAC GGA GTA CCG GGG TCG GAT TAT      3293
Glu Val Ala Arg Val Ala Gly Leu Tyr Gly Val Pro Gly Ser Asp Tyr
155                 160                 165
```

-continued

| | |
|---|---|
| GCA TAC CCT AGG AAA TCG GAA TTA ATA TCC TCC ATT CGA CGG GAT CCC<br>Ala Tyr Pro Arg Lys Ser Glu Leu Ile Ser Ser Ile Arg Arg Asp Pro<br>170                    175                    180 | 3341 |
| CAG GGT TCT TTC TGG ACT AGT CCT ACA CCC CGT GGA AAT AAA TAT TTC<br>Gln Gly Ser Phe Trp Thr Ser Pro Thr Pro Arg Gly Asn Lys Tyr Phe<br>185                    190                    195                    200 | 3389 |
| ATA TGG ATT AAT AAA ACA ATG CAC ACC ATG GGC GTG GAA GTT AGA AAT<br>Ile Trp Ile Asn Lys Thr Met His Thr Met Gly Val Glu Val Arg Asn<br>                  205                    210                    215 | 3437 |
| GTC GAC TAC AAA GAC AAC GGC TAC TTT CAA GTG ATA CTG CGT GAT AGA<br>Val Asp Tyr Lys Asp Asn Gly Tyr Phe Gln Val Ile Leu Arg Asp Arg<br>          220                    225                    230 | 3485 |
| TTT AAT CGC CCA TTG GTA GAA AAA CAT ATT TAC ATG CGT GTG TGC CAA<br>Phe Asn Arg Pro Leu Val Glu Lys His Ile Tyr Met Arg Val Cys Gln<br>              235                    240                    245 | 3533 |
| CGA CCC GCA TCC GTG GAT GTA TTG GCC CCT CCA GTT CTC AGC GGA GAA<br>Arg Pro Ala Ser Val Asp Val Leu Ala Pro Pro Val Leu Ser Gly Glu<br>250                    255                    260 | 3581 |
| AAC TAC AAA GCA TCT TGC ATC GTT AGA CAT TTT TAT CCC CCG GGA TCT<br>Asn Tyr Lys Ala Ser Cys Ile Val Arg His Phe Tyr Pro Pro Gly Ser<br>265                    270                    275                    280 | 3629 |
| GTC TAC GTA TCT TGG AGA CGT AAC GGA AAC ATT GCC ACA CCC CGC AAG<br>Val Tyr Val Ser Trp Arg Arg Asn Gly Asn Ile Ala Thr Pro Arg Lys<br>                  285                    290                    295 | 3677 |
| GAC CGT GAC GGG AGT TTT TGG TGG TTC GAA TCT GGC CGC GGG GCC ACA<br>Asp Arg Asp Gly Ser Phe Trp Trp Phe Glu Ser Gly Arg Gly Ala Thr<br>          300                    305                    310 | 3725 |
| CTA GTA TCC ACA ATA ACC CTC GGA AAC TCT GGA CTC GAA TCT CCT CCA<br>Leu Val Ser Thr Ile Thr Leu Gly Asn Ser Gly Leu Glu Ser Pro Pro<br>              315                    320                    325 | 3773 |
| AAG GTT TCC TGC TTG GTA GCG TGG AGG CAA GGC GAT ATG ATA AGC ACA<br>Lys Val Ser Cys Leu Val Ala Trp Arg Gln Gly Asp Met Ile Ser Thr<br>330                    335                    340 | 3821 |
| TCG AAT GCT ACA GCT GTA CCG ACG GTA TAT TAT CAC CCC CGT ATC TCT<br> Ser Asn Ala Thr Ala Val Pro Thr Val Tyr Tyr His Pro Arg Ile Ser<br>345                    350                    355                    360 | 3869 |
| CTG GCA TTT AAA GAT GGG TAT GCA ATA TGT ACT ATA GAA TGT GTT CCC<br>Leu Ala Phe Lys Asp Gly Tyr Ala Ile Cys Thr Ile Glu Cys Val Pro<br>                  365                    370                    375 | 3917 |
| TCT GGG ATT ACT GTG AGG TGG TTA GTT CAT GAT GAA CCC CAG CCT AAC<br>Ser Gly Ile Thr Val Arg Trp Leu Val His Asp Glu Pro Gln Pro Asn<br>              380                    385                    390 | 3965 |
| ACA ACT TAT GAT ACT GTG GTT ACA GGT CTC TGC AGG ACC ATC GAT CGT<br>Thr Thr Tyr Asp Thr Val Val Thr Gly Leu Cys Arg Thr Ile Asp Arg<br>          395                    400                    405 | 4013 |
| TAT AGA AAT CTC GCC AGT CGG ATT CCA GTC CAG GAC AAC TGG GCG AAA<br>Tyr Arg Asn Leu Ala Ser Arg Ile Pro Val Gln Asp Asn Trp Ala Lys<br>          410                    415                    420 | 4061 |
| ACG AAG TAT ACG TGC AGA CTA ATT GGA TAT CCG TTC GAC GTG GAT AGA<br>Thr Lys Tyr Thr Cys Arg Leu Ile Gly Tyr Pro Phe Asp Val Asp Arg<br>425                    430                    435                    440 | 4109 |
| TTT CAA AAT TCC GAA TAT TAT GAT GCA ACG CCG TCG GCA AGA GGA ATG<br>Phe Gln Asn Ser Glu Tyr Tyr Asp Ala Thr Pro Ser Ala Arg Gly Met<br>                  445                    450                    455 | 4157 |
| CCG ATG ATT GTA ACA ATT ACG GCC GTT CTA GGA CTG GCC TTG TTT TTA<br>Pro Met Ile Val Thr Ile Thr Ala Val Leu Gly Leu Ala Leu Phe Leu<br>                  460                    465                    470 | 4205 |
| GGT ATT GGT ATC ATT ATC ACA GCC CTA TGC TTT TAC CTA CCG GGG CGG<br>Gly Ile Gly Ile Ile Ile Thr Ala Leu Cys Phe Tyr Leu Pro Gly Arg<br>475                    480                    485 | 4253 |

```
AAT TAAGATTAAC CATCGTATGT GATATAAAAA TTATTAAGTG TTATAACCGA         4306
Asn
    490

TCGCATTCTT CTGTTTCGAT TCACAATAAA TAAAATGGTA TTGTAATCAG CACCATCGCA  4366

TTGTTTCGTA GATGACTCAT GTTCAGTCCG CGTGATGTCA AAAATACGTA TTTTTGGTAT  4426

CACGCAGCGG CCAAAATGCC CATTATGTTA TTTTTACTCC AAACGCGGTA TTTAAAACAT  4486

CGGGACGTAC ATCATGTGGC GCACGTTAAT CGTATACGGT GCCGCTACAT TAAAAATCGC  4546

AAGTCTCCGA ATATCAAGCT CACGGCCAAA ACGTCGGTAA TAATCTTACG CATCGAATGT  4606

GATACGGATA CCGTACAATC GCTGAGTAGA TTTCCTATAT AGTTACTCAG TAGTGATACA  4666

CAATCACAAA ATCGCTGGGG TATATCATAT AAGA ATG ATG TCG CCC ACC CCT     4718
                                      Met Met Ser Pro Thr Pro
                                        1               5

GAA GAT GAT CGC GAT CTC GTT GTG GTT CGT GGA CGT CTC CGA ATG ATG    4766
Glu Asp Asp Arg Asp Leu Val Val Val Arg Gly Arg Leu Arg Met Met
            10                  15                  20

GAT AGC GGC ACG GAA ACA GAT AGA GAG CAA CGA CAT CCA CGT ACG ACT    4814
Asp Ser Gly Thr Glu Thr Asp Arg Glu Gln Arg His Pro Arg Thr Thr
        25                  30                  35

TGG CGA TCG ATC TGT TGT GGG TGT ACG ATA GGA ATG GTA TTT ACC ATA   4862
Trp Arg Ser Ile Cys Cys Gly Cys Thr Ile Gly Met Val Phe Thr Ile
    40                  45                  50

TTC GTT CTC GTA GCG GCA GTA TTG TTG GGA TCA CTA TTC ACT GTT TCA    4910
Phe Val Leu Val Ala Ala Val Leu Leu Gly Ser Leu Phe Thr Val Ser
55              60                  65                  70

TAC ATG GCC ATG GAA TCG GGA ACA TGT CCC GAT GAA TGG ATT GGT TTG    4958
Tyr Met Ala Met Glu Ser Gly Thr Cys Pro Asp Glu Trp Ile Gly Leu
            75                  80                  85

GGT TAT AGT TGC ATG CGC GTG GCC GGG AAA AAT GCA ACT GAT CTT GAG    5006
Gly Tyr Ser Cys Met Arg Val Ala Gly Lys Asn Ala Thr Asp Leu Glu
        90                  95                  100

GCG TTG GAT ACA TGT GCT CGG CAT AAC AGC AAA CTT ATT GAC TTC GCA    5054
Ala Leu Asp Thr Cys Ala Arg His Asn Ser Lys Leu Ile Asp Phe Ala
    105                 110                 115

AAC GCC AAA GTT CTG GTT GAA GCT ATC GCC CCA TTC GGT GTG CCA AAT    5102
Asn Ala Lys Val Leu Val Glu Ala Ile Ala Pro Phe Gly Val Pro Asn
120                 125                 130

GCA GCA TAT GGG GAA GTC TTC CGG TTA AGG GAC AGC AAA ACC ACG TGT    5150
Ala Ala Tyr Gly Glu Val Phe Arg Leu Arg Asp Ser Lys Thr Thr Cys
135             140                 145                 150

ATA CGA CCT ACC ATG GGA GGA CCC GTG TCG GCA GAC TGT CCT GTA ACA    5198
Ile Arg Pro Thr Met Gly Gly Pro Val Ser Ala Asp Cys Pro Val Thr
            155                 160                 165

TGT ACC GTT ATA TGT CAG CGA CCC AGG CCT CTA AGT ACC ATG TCT TCC    5246
Cys Thr Val Ile Cys Gln Arg Pro Arg Pro Leu Ser Thr Met Ser Ser
        170                 175                 180

ATC ATT AGA GAT GCC CGC GTG TAT CTT CAT TTA GAA CGA CGC GAT TAT    5294
Ile Ile Arg Asp Ala Arg Val Tyr Leu His Leu Glu Arg Arg Asp Tyr
    185                 190                 195

TAT GAA GTC TAC GCC TCT GTC CTC TCT AAT GCG ATG AGT AAA TAAAAACGCA 5346
Tyr Glu Val Tyr Ala Ser Val Leu Ser Asn Ala Met Ser Lys
200                 205                 210

CCTCTAACGG TTACTGTGTT TATTATCCAA TCACACCATA GACATTATTA CAATAATATG  5406

GATCTTTATT TCATATAATG                                              5426

(2) INFORMATION FOR SEQ ID NO:4:

(i) SEQUENCE CHARACTERISTICS:
```

(A) LENGTH: 369 amino acids
(B) TYPE: amino acid
(D) TOPOLOGY: linear (ii) MOLECULE TYPE: protein (xi) SEQUENCE DESCRIPTION: SEQ ID NO:4:

```
Met Met Ala Gly Ile Thr Val Ala Cys Asp His Thr Ala Gly Glu Ala
 1               5                  10                  15

His Thr Pro Glu Asp Met Gln Lys Lys Trp Arg Ile Ile Leu Ala Gly
            20                  25                  30

Glu Lys Phe Met Thr Ile Ser Ala Ser Leu Lys Ser Ile Val Ser Cys
        35                  40                  45

Val Lys Asn Pro Leu Leu Thr Phe Gly Ala Asp Gly Leu Ile Val Gln
 50                  55                  60

Gly Thr Val Cys Gly Gln Arg Ile Phe Val Pro Ile Asp Arg Asp Ser
 65                  70                  75                  80

Phe Ser Glu Tyr Glu Trp His Gly Pro Thr Ala Met Phe Leu Ala Leu
                85                  90                  95

Thr Asp Ser Arg Arg Thr Leu Leu Asp Ala Phe Lys Cys Glu Lys Arg
            100                 105                 110

Arg Ala Ile Asp Val Ser Phe Thr Phe Ala Gly Glu Pro Pro Cys Arg
        115                 120                 125

His Leu Ile Gln Ala Val Thr Tyr Met Thr Asp Gly Gly Ser Val Ser
130                 135                 140

Asn Thr Ile Ile Lys Tyr Glu Leu Trp Asn Ala Ser Thr Ile Phe Pro
145                 150                 155                 160

Gln Lys Thr Pro Asp Val Thr Phe Ser Leu Asn Lys Gln Gln Leu Asn
                165                 170                 175

Lys Ile Leu Ala Val Ala Ser Lys Leu Gln His Glu Glu Leu Val Phe
            180                 185                 190

Ser Leu Lys Pro Glu Gly Gly Phe Tyr Val Gly Thr Val Cys Thr Val
        195                 200                 205

Ile Ser Phe Glu Val Asp Gly Thr Ala Met Thr Gln Tyr Pro Tyr Asn
210                 215                 220

Pro Pro Thr Ser Ala Thr Leu Ala Leu Val Ala Cys Arg Lys Lys
225                 230                 235                 240

Lys Ala Asn Lys Asn Thr Ile Leu Thr Ala Tyr Gly Ser Gly Lys Pro
                245                 250                 255

Phe Cys Val Ala Leu Glu Asp Thr Ser Ala Phe Arg Asn Ile Val Asn
            260                 265                 270

Lys Ile Lys Ala Gly Thr Ser Gly Val Asp Leu Gly Phe Tyr Thr Thr
        275                 280                 285

Cys Asp Pro Pro Met Leu Cys Ile Arg Pro His Ala Phe Gly Ser Pro
290                 295                 300

Thr Ala Phe Leu Phe Cys Asn Thr Asp Cys Met Thr Ile Tyr Glu Leu
305                 310                 315                 320

Glu Glu Val Ser Ala Val Asp Gly Ala Ile Arg Ala Lys Arg Ile Asn
                325                 330                 335

Glu Tyr Phe Pro Thr Val Ser Gln Ala Thr Ser Lys Lys Arg Lys Gln
            340                 345                 350

Ser Pro Pro Pro Ile Glu Arg Glu Arg Lys Thr Thr Arg Ala Asp Thr
        355                 360                 365

Gln
```

(2) INFORMATION FOR SEQ ID NO:5:

(i) SEQUENCE CHARACTERISTICS:
        (A) LENGTH: 422 amino acids
        (B) TYPE: amino acid
        (D) TOPOLOGY: linear (ii) MOLECULE TYPE: protein (xi) SEQUENCE DESCRIPTION: SEQ ID NO:5:

```
Met Pro Ser Gly Ala Ser Ser Pro Pro Ala Tyr Thr Ser Ala
 1               5                  10                  15

Ala Pro Leu Glu Thr Tyr Asn Ser Trp Leu Ser Ala Phe Ser Cys Ala
                 20                  25                  30

Tyr Pro Gln Cys Thr Ala Gly Arg Gly His Arg Gln Asn Gly Lys Lys
             35                  40                  45

Cys Ile Arg Cys Ile Val Ile Ser Val Cys Ser Leu Val Cys Ile Ala
 50                  55                  60

Ala His Leu Ala Val Thr Val Ser Gly Val Ala Leu Ile Pro Leu Ile
 65                  70                  75                  80

Asp Gln Asn Arg Ala Tyr Gly Asn Cys Thr Val Cys Val Ile Ala Gly
                 85                  90                  95

Phe Ile Ala Thr Phe Ala Ala Arg Leu Thr Ile Arg Leu Ser Glu Thr
                100                 105                 110

Leu Met Leu Val Gly Lys Pro Ala Gln Phe Ile Phe Ala Ile Ile Ala
        115                 120                 125

Ser Val Ala Glu Thr Leu Ile Asn Asn Glu Ala Leu Ala Ile Ser Asn
        130                 135                 140

Thr Thr Tyr Lys Thr Ala Leu Arg Ile Ile Glu Val Thr Ser Leu Ala
145                 150                 155                 160

Cys Phe Val Met Leu Gly Ala Ile Ile Thr Ser His Asn Tyr Val Cys
                165                 170                 175

Ile Ser Thr Ala Gly Asp Leu Thr Trp Lys Gly Ile Phe His Ala
                180                 185                 190

Tyr His Gly Thr Leu Leu Gly Ile Thr Ile Pro Asn Ile His Pro Ile
        195                 200                 205

Pro Leu Ala Gly Phe Leu Ala Val Tyr Thr Ile Leu Ala Ile Asn Ile
        210                 215                 220

Ala Arg Asp Ala Ser Ala Thr Leu Leu Ser Thr Cys Tyr Tyr Arg Asn
225                 230                 235                 240

Cys Arg Glu Arg Thr Ile Leu Arg Pro Ser Arg Leu Gly His Gly Tyr
                245                 250                 255

Thr Ile Pro Ser Pro Gly Ala Asp Met Leu Tyr Glu Glu Asp Val Tyr
                260                 265                 270

Ser Phe Asp Ala Ala Lys Gly His Tyr Ser Ser Ile Phe Leu Cys Tyr
        275                 280                 285

Ala Met Gly Leu Thr Thr Pro Leu Ile Ile Ala Leu His Lys Tyr Met
        290                 295                 300

Ala Gly Ile Lys Asn Ser Ser Asp Trp Thr Ala Thr Leu Gln Gly Met
305                 310                 315                 320

Tyr Gly Leu Val Leu Gly Ser Leu Ser Ser Leu Cys Ile Pro Ser Ser
                325                 330                 335

Asn Asn Asp Ala Leu Ile Arg Pro Ile Gln Ile Leu Ile Leu Ile Ile
                340                 345                 350

Gly Ala Leu Ala Ile Ala Leu Ala Gly Cys Gly Gln Ile Ile Gly Pro
                355                 360                 365
```

```
Thr Leu Phe Ala Ala Ser Ser Ala Ala Met Ser Cys Phe Thr Cys Ile
    370                 375                 380

Asn Ile Arg Ala Thr Asn Lys Gly Val Asn Lys Leu Ala Ala Ala Ser
385                 390                 395                 400

Val Val Lys Ser Val Leu Gly Phe Ile Ile Ser Gly Met Leu Thr Cys
                405                 410                 415

Val Leu Leu Pro Leu Ser
            420

(2) INFORMATION FOR SEQ ID NO:6:

(i) SEQUENCE CHARACTERISTICS:
        (A) LENGTH: 489 amino acids
        (B) TYPE: amino acid
        (D) TOPOLOGY: linear (ii) MOLECULE TYPE: protein (xi) SEQUENCE DESCRIPTION: SEQ ID NO:6:

Met Val Ser Asn Met Arg Val Leu Arg Val Leu Arg Leu Thr Gly Trp
1               5                   10                  15

Val Gly Ile Phe Leu Val Leu Ser Leu Gln Gln Thr Ser Cys Ala Gly
                20                  25                  30

Leu Pro His Asn Val Asp Thr His His Ile Leu Thr Phe Asn Pro Ser
            35                  40                  45

Pro Ile Ser Ala Asp Gly Val Pro Leu Ser Glu Val Pro Asn Ser Pro
        50                  55                  60

Thr Thr Glu Leu Ser Thr Thr Val Ala Thr Lys Thr Ala Val Pro Thr
65                  70                  75                  80

Thr Glu Ser Thr Ser Ser Glu Ala His Arg Asn Ser Ser His Lys
                85                  90                  95

Ile Pro Asp Ile Ile Cys Asp Arg Glu Glu Val Phe Val Phe Leu Asn
            100                 105                 110

Asn Thr Gly Arg Ile Leu Cys Asp Leu Ile Val Asp Pro Pro Ser Asp
        115                 120                 125

Asp Glu Trp Ser Asn Phe Ala Leu Asp Val Thr Phe Asn Pro Ile Glu
    130                 135                 140

Tyr His Ala Asn Glu Lys Asn Val Glu Val Ala Arg Val Ala Gly Leu
145                 150                 155                 160

Tyr Gly Val Pro Gly Ser Asp Tyr Ala Tyr Pro Arg Lys Ser Glu Leu
                165                 170                 175

Ile Ser Ser Ile Arg Arg Asp Pro Gln Gly Ser Phe Trp Thr Ser Pro
                180                 185                 190

Thr Pro Arg Gly Asn Lys Tyr Phe Ile Trp Ile Asn Lys Thr Met His
            195                 200                 205

Thr Met Gly Val Glu Val Arg Asn Val Asp Tyr Lys Asp Asn Gly Tyr
    210                 215                 220

Phe Gln Val Ile Leu Arg Asp Arg Phe Asn Arg Pro Leu Val Glu Lys
225                 230                 235                 240

His Ile Tyr Met Arg Val Cys Gln Arg Pro Ala Ser Val Asp Val Leu
                245                 250                 255

Ala Pro Pro Val Leu Ser Gly Glu Asn Tyr Lys Ala Ser Cys Ile Val
            260                 265                 270

Arg His Phe Tyr Pro Pro Gly Ser Val Tyr Val Ser Trp Arg Arg Asn
    275                 280                 285

Gly Asn Ile Ala Thr Pro Arg Lys Asp Arg Asp Gly Ser Phe Trp Trp
290                 295                 300
```

```
Phe Glu Ser Gly Arg Gly Ala Thr Leu Val Ser Thr Ile Thr Leu Gly
305                 310                 315                 320

Asn Ser Gly Leu Glu Ser Pro Pro Lys Val Ser Cys Leu Val Ala Trp
            325                 330                 335

Arg Gln Gly Asp Met Ile Ser Thr Ser Asn Ala Thr Ala Val Pro Thr
            340                 345                 350

Val Tyr Tyr His Pro Arg Ile Ser Leu Ala Phe Lys Asp Gly Tyr Ala
            355                 360                 365

Ile Cys Thr Ile Glu Cys Val Pro Ser Gly Ile Thr Val Arg Trp Leu
370                 375                 380

Val His Asp Glu Pro Gln Pro Asn Thr Thr Tyr Asp Thr Val Val Thr
385                 390                 395                 400

Gly Leu Cys Arg Thr Ile Asp Arg Tyr Arg Asn Leu Ala Ser Arg Ile
                405                 410                 415

Pro Val Gln Asp Asn Trp Ala Lys Thr Lys Tyr Thr Cys Arg Leu Ile
            420                 425                 430

Gly Tyr Pro Phe Asp Val Asp Arg Phe Gln Asn Ser Glu Tyr Tyr Asp
            435                 440                 445

Ala Thr Pro Ser Ala Arg Gly Met Pro Met Ile Val Thr Ile Thr Ala
  450                 455                 460

Val Leu Gly Leu Ala Leu Phe Leu Gly Ile Gly Ile Ile Ile Thr Ala
465                 470                 475                 480

Leu Cys Phe Tyr Leu Pro Gly Arg Asn
                485

(2) INFORMATION FOR SEQ ID NO:7:

(i) SEQUENCE CHARACTERISTICS:
        (A) LENGTH: 212 amino acids
        (B) TYPE: amino acid
        (D) TOPOLOGY: linear (ii) MOLECULE TYPE: protein (xi) SEQUENCE DESCRIPTION: SEQ ID NO:7:

Met Met Ser Pro Thr Pro Glu Asp Asp Arg Asp Leu Val Val Val Arg
 1               5                  10                  15

Gly Arg Leu Arg Met Met Asp Ser Gly Thr Glu Thr Asp Arg Glu Gln
            20                  25                  30

Arg His Pro Arg Thr Thr Trp Arg Ser Ile Cys Cys Gly Cys Thr Ile
        35                  40                  45

Gly Met Val Phe Thr Ile Phe Val Leu Val Ala Ala Val Leu Leu Gly
    50                  55                  60

Ser Leu Phe Thr Val Ser Tyr Met Ala Met Glu Ser Gly Thr Cys Pro
65                  70                  75                  80

Asp Glu Trp Ile Gly Leu Gly Tyr Ser Cys Met Arg Val Ala Gly Lys
                85                  90                  95

Asn Ala Thr Asp Leu Glu Ala Leu Asp Thr Cys Ala Arg His Asn Ser
            100                 105                 110

Lys Leu Ile Asp Phe Ala Asn Ala Lys Val Leu Val Glu Ala Ile Ala
        115                 120                 125

Pro Phe Gly Val Pro Asn Ala Ala Tyr Gly Glu Val Phe Arg Leu Arg
    130                 135                 140

Asp Ser Lys Thr Thr Cys Ile Arg Pro Thr Met Gly Gly Pro Val Ser
145                 150                 155                 160
```

```
Ala Asp Cys Pro Val Thr Cys Thr Val Ile Cys Gln Arg Pro Arg Pro
            165                 170                 175

Leu Ser Thr Met Ser Ser Ile Ile Arg Asp Ala Arg Val Tyr Leu His
            180                 185                 190

Leu Glu Arg Arg Asp Tyr Tyr Glu Val Tyr Ala Ser Val Leu Ser Asn
            195                 200                 205

Ala Met Ser Lys
    210
```

(2) INFORMATION FOR SEQ ID NO:8:

(i) SEQUENCE CHARACTERISTICS:
        (A) LENGTH: 1506 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION: 1..1506

(xi) SEQUENCE DESCRIPTION: SEQ ID NO:8:

```
ATG CTC ACG CCG CGT GTG TTA CGA GCT TTG GGG TGG ACT GGA CTC TTT    48
Met Leu Thr Pro Arg Val Leu Arg Ala Leu Gly Trp Thr Gly Leu Phe
 1               5                  10                  15

TTT TTG CTT TTA TCT CCG AGC AAC GTC CTA GGA GCC AGC CTT AGC CGG    96
Phe Leu Leu Leu Ser Pro Ser Asn Val Leu Gly Ala Ser Leu Ser Arg
             20                  25                  30

GAT CTC GAA ACA CCC CCA TTT CTA TCC TTT GAT CCA TCC AAC ATT TCA   144
Asp Leu Glu Thr Pro Pro Phe Leu Ser Phe Asp Pro Ser Asn Ile Ser
         35                  40                  45

ATT AAC GGC GCG CCT TTA ACT GAG GTA CCT CAT GCA CCT TCC ACA GAA   192
Ile Asn Gly Ala Pro Leu Thr Glu Val Pro His Ala Pro Ser Thr Glu
 50                  55                  60

AGT GTG TCA ACA AAT TCG GAA AGT ACC AAT GAA CAT ACC ATA ACA GAA   240
Ser Val Ser Thr Asn Ser Glu Ser Thr Asn Glu His Thr Ile Thr Glu
 65                  70                  75                  80

ACG ACG GGC AAG AAC GCA TAC ATC CAC AAC AAT GCG TCT ACG GAC AAG   288
Thr Thr Gly Lys Asn Ala Tyr Ile His Asn Asn Ala Ser Thr Asp Lys
                 85                  90                  95

CAA AAT GCG AAC GAC ACT CAT AAA ACG CCC AAT ATA CTC TGC GAT ACG   336
Gln Asn Ala Asn Asp Thr His Lys Thr Pro Asn Ile Leu Cys Asp Thr
            100                 105                 110

GAA GAA GTT TTT GTT TTC CTT AAC GAA ACG GGA AGA TTT GTT TGT ACT   384
Glu Glu Val Phe Val Phe Leu Asn Glu Thr Gly Arg Phe Val Cys Thr
        115                 120                 125

CTC AAA GTC GAC CCC CCC TCG GAT AGT GAA TGG TCC AAC TTT GTT CTA   432
Leu Lys Val Asp Pro Pro Ser Asp Ser Glu Trp Ser Asn Phe Val Leu
    130                 135                 140

GAT CTG ATC TTT AAC CCA ATT GAA TAC CAC GCC AAC GAA AAG AAT GTG   480
Asp Leu Ile Phe Asn Pro Ile Glu Tyr His Ala Asn Glu Lys Asn Val
145                 150                 155                 160

GAA GCG GCG CGT ATC GCT GGT CTC TAT GGA GTC CCC GGA TCA GAC TAT   528
Glu Ala Ala Arg Ile Ala Gly Leu Tyr Gly Val Pro Gly Ser Asp Tyr
                165                 170                 175

GCA TAC CCA CGT CAA TCT GAA TTA ATT TCT TCG ATT CGA CGA GAT CCC   576
Ala Tyr Pro Arg Gln Ser Glu Leu Ile Ser Ser Ile Arg Arg Asp Pro
            180                 185                 190
```

```
CAG GGC ACA TTT TGG ACG AGC CCA TCA CCT CAT GGA AAC AAG TAC TTC        624
Gln Gly Thr Phe Trp Thr Ser Pro Ser Pro His Gly Asn Lys Tyr Phe
        195                 200                 205

ATA TGG ATA AAC AAA ACA ACC AAT ACG ATG GGC GTG GAA ATT AGA AAT        672
Ile Trp Ile Asn Lys Thr Thr Asn Thr Met Gly Val Glu Ile Arg Asn
210                 215                 220

GTA GAT TAT GCT GAT AAT GGC TAC ATG CAA GTC ATT ATG CGT GAC CAT        720
Val Asp Tyr Ala Asp Asn Gly Tyr Met Gln Val Ile Met Arg Asp His
225                 230                 235                 240

TTT AAT CGG CCT TTA ATA GAT AAA CAT ATT TAC ATA CGT GTG TGT CAA        768
Phe Asn Arg Pro Leu Ile Asp Lys His Ile Tyr Ile Arg Val Cys Gln
                245                 250                 255

CGA CCT GCA TCA GTG GAT GTA CTG GCC CCT CCA GTC CTC AGC GGA GAA        816
Arg Pro Ala Ser Val Asp Val Leu Ala Pro Pro Val Leu Ser Gly Glu
            260                 265                 270

AAT TAC AAG GCA TCT TGT ATC GTT AGA CAC TTT TAT CCC CCT GGA TCT        864
Asn Tyr Lys Ala Ser Cys Ile Val Arg His Phe Tyr Pro Pro Gly Ser
        275                 280                 285

GTC TAT GTA TCT TGG AGA CAG AAT GGA AAC ATT GCA ACT CCT CGG AAA        912
Val Tyr Val Ser Trp Arg Gln Asn Gly Asn Ile Ala Thr Pro Arg Lys
290                 295                 300

GAT CGC GAT GGA AGT TTT TGG TGG TTC GAA TCT GGT AGA GGA GCT ACG        960
Asp Arg Asp Gly Ser Phe Trp Trp Phe Glu Ser Gly Arg Gly Ala Thr
305                 310                 315                 320

TTG GTT TCT ACA ATA ACA TTG GGA AAT TCA GGA ATT GAT TTC CCC CCC       1008
Leu Val Ser Thr Ile Thr Leu Gly Asn Ser Gly Ile Asp Phe Pro Pro
                325                 330                 335

AAA ATA TCT TGT CTG GTT GCC TGG AAG CAG GGT GAT ATG ATC AGC ACG       1056
Lys Ile Ser Cys Leu Val Ala Trp Lys Gln Gly Asp Met Ile Ser Thr
            340                 345                 350

ACG AAT GCC ACA GCT ATC CCG ACG GTA TAT CAT CAT CCC CGT TTA TCC       1104
Thr Asn Ala Thr Ala Ile Pro Thr Val Tyr His His Pro Arg Leu Ser
        355                 360                 365

CTG GCT TTT AAA GAT GGG TAT GCA ATA TGT ACT ATA GAA TGT GTC CCC       1152
Leu Ala Phe Lys Asp Gly Tyr Ala Ile Cys Thr Ile Glu Cys Val Pro
370                 375                 380

TCT GAG ATT ACT GTA CGG TGG TTA GTA CAT GAT GAA GCG CAG CCT AAC       1200
 Ser Glu Ile Thr Val Arg Trp Leu Val His Asp Glu Ala Gln Pro Asn
385                 390                 395                 400

ACA ACT TAT AAT ACT GTG GTT ACA GGT CTC TGC CGG ACC ATC GAT CGC       1248
Thr Thr Tyr Asn Thr Val Val Thr Gly Leu Cys Arg Thr Ile Asp Arg
                405                 410                 415

CAT AGA AAT CTC CTC AGC CGC ATT CCA GTA TGG GAC AAT TGG ACG AAA       1296
His Arg Asn Leu Leu Ser Arg Ile Pro Val Trp Asp Asn Trp Thr Lys
            420                 425                 430

ACA AAA TAT ACG TGC AGA CTC ATA GGC TAC CCC TTC GAT GAA GAT AAA       1344
Thr Lys Tyr Thr Cys Arg Leu Ile Gly Tyr Pro Phe Asp Glu Asp Lys
        435                 440                 445

TTT CAA GAT TCG GAA TAT TAC GAT GCA ACT CCA TCT GCA AGA GGA ACA       1392
Phe Gln Asp Ser Glu Tyr Tyr Asp Ala Thr Pro Ser Ala Arg Gly Thr
450                 455                 460

CCC ATG GTT ATT ACG GTT ACG GCA GTT TTG GGA TTG GCT GTA ATT TTA       1440
Pro Met Val Ile Thr Val Thr Ala Val Leu Gly Leu Ala Val Ile Leu
465                 470                 475                 480

GGG ATG GGG ATA ATC ATG ACT GCC CTA TGT TTA TAC AAC TCC ACA CGA       1488
Gly Met Gly Ile Ile Met Thr Ala Leu Cys Leu Tyr Asn Ser Thr Arg
                485                 490                 495

AAA AAT ATT CGA TTA TAA                                               1506
Lys Asn Ile Arg Leu
            500
```

(2) INFORMATION FOR SEQ ID NO:9:

(i) SEQUENCE CHARACTERISTICS:
        (A) LENGTH: 501 amino acids
        (B) TYPE: amino acid
        (D) TOPOLOGY: linear (ii) MOLECULE TYPE: protein (xi) SEQUENCE DESCRIPTION: SEQ ID NO:9:

```
Met Leu Thr Pro Arg Val Leu Arg Ala Leu Gly Trp Thr Gly Leu Phe
 1               5                  10                  15

Phe Leu Leu Leu Ser Pro Ser Asn Val Leu Gly Ala Ser Leu Ser Arg
            20                  25                  30

Asp Leu Glu Thr Pro Pro Phe Leu Ser Phe Asp Pro Ser Asn Ile Ser
        35                  40                  45

Ile Asn Gly Ala Pro Leu Thr Glu Val Pro His Ala Pro Ser Thr Glu
    50                  55                  60

Ser Val Ser Thr Asn Ser Glu Ser Thr Asn Glu His Thr Ile Thr Glu
65                  70                  75                  80

Thr Thr Gly Lys Asn Ala Tyr Ile His Asn Asn Ala Ser Thr Asp Lys
                85                  90                  95

Gln Asn Ala Asn Asp Thr His Lys Thr Pro Asn Ile Leu Cys Asp Thr
            100                 105                 110

Glu Glu Val Phe Val Phe Leu Asn Glu Thr Gly Arg Phe Val Cys Thr
        115                 120                 125

Leu Lys Val Asp Pro Pro Ser Asp Ser Glu Trp Ser Asn Phe Val Leu
    130                 135                 140

Asp Leu Ile Phe Asn Pro Ile Glu Tyr His Ala Asn Glu Lys Asn Val
145                 150                 155                 160

Glu Ala Ala Arg Ile Ala Gly Leu Tyr Gly Val Pro Gly Ser Asp Tyr
                165                 170                 175

Ala Tyr Pro Arg Gln Ser Glu Leu Ile Ser Ser Ile Arg Arg Asp Pro
            180                 185                 190

Gln Gly Thr Phe Trp Thr Ser Pro Ser Pro His Gly Asn Lys Tyr Phe
        195                 200                 205

Ile Trp Ile Asn Lys Thr Thr Asn Thr Met Gly Val Glu Ile Arg Asn
    210                 215                 220

Val Asp Tyr Ala Asp Asn Gly Tyr Met Gln Val Ile Met Arg Asp His
225                 230                 235                 240

Phe Asn Arg Pro Leu Ile Asp Lys His Ile Tyr Ile Arg Val Cys Gln
                245                 250                 255

Arg Pro Ala Ser Val Asp Val Leu Ala Pro Pro Val Leu Ser Gly Glu
            260                 265                 270

Asn Tyr Lys Ala Ser Cys Ile Val Arg His Phe Tyr Pro Pro Gly Ser
        275                 280                 285

Val Tyr Val Ser Trp Arg Gln Asn Gly Asn Ile Ala Thr Pro Arg Lys
    290                 295                 300

Asp Arg Asp Gly Ser Phe Trp Trp Phe Glu Ser Gly Arg Gly Ala Thr
305                 310                 315                 320

Leu Val Ser Thr Ile Thr Leu Gly Asn Ser Gly Ile Asp Phe Pro Pro
                325                 330                 335

Lys Ile Ser Cys Leu Val Ala Trp Lys Gln Gly Asp Met Ile Ser Thr
            340                 345                 350
```

```
Thr Asn Ala Thr Ala Ile Pro Thr Val Tyr His His Pro Arg Leu Ser
            355                 360                 365
Leu Ala Phe Lys Asp Gly Tyr Ala Ile Cys Thr Ile Glu Cys Val Pro
            370                 375                 380
Ser Glu Ile Thr Val Arg Trp Leu Val His Asp Glu Ala Gln Pro Asn
385                 390                 395                 400
Thr Thr Tyr Asn Thr Val Val Thr Gly Leu Cys Arg Thr Ile Asp Arg
                405                 410                 415
His Arg Asn Leu Leu Ser Arg Ile Pro Val Trp Asp Asn Trp Thr Lys
            420                 425                 430
Thr Lys Tyr Thr Cys Arg Leu Ile Gly Tyr Pro Phe Asp Glu Asp Lys
            435                 440                 445
Phe Gln Asp Ser Glu Tyr Tyr Asp Ala Thr Pro Ser Ala Arg Gly Thr
            450                 455                 460
Pro Met Val Ile Thr Val Thr Ala Val Leu Gly Leu Ala Val Ile Leu
465                 470                 475                 480
Gly Met Gly Ile Ile Met Thr Ala Leu Cys Leu Tyr Asn Ser Thr Arg
                485                 490                 495
Lys Asn Ile Arg Leu
            500
```

(2) INFORMATION FOR SEQ ID NO:10:

(i) SEQUENCE CHARACTERISTICS:
        (A) LENGTH: 1734 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION: 1..1734

(xi) SEQUENCE DESCRIPTION: SEQ ID NO:10:

```
ATG GAC CGC GCC GTT AGC CAA GTT GCG TTA GAG AAT GAT GAA AGA GAG    48
Met Asp Arg Ala Val Ser Gln Val Ala Leu Glu Asn Asp Glu Arg Glu
 1               5                  10                  15

GCA AAA AAT ACA TGG CGC TTG ATA TTC GGA ATT GCA ATC TTA TTC TTA    96
Ala Lys Asn Thr Trp Arg Leu Ile Phe Arg Ile Ala Ile Leu Phe Leu
                20                  25                  30

ACA GTA GTG ACC TTG GCT ATA TCT GTA GCC TCC CTT TTA TAT AGC ATG   144
Thr Val Val Thr Leu Ala Ile Ser Val Ala Ser Leu Leu Tyr Ser Met
             35                  40                  45

GGG GCT AGC ACA CCT AGC GAT CTT GTA GGC ATA CCG ACT AGG ATT TCC   192
Gly Ala Ser Thr Pro Ser Asp Leu Val Gly Ile Pro Thr Arg Ile Ser
    50                  55                  60

AGG GCA GAA GAA AAG ATT ACA TCT ACA CTT GGT TCC AAT CAA GAT GTA   240
Arg Ala Glu Glu Lys Ile Thr Ser Thr Leu Gly Ser Asn Gln Asp Val
65                  70                  75                  80

GTA GAT AGG ATA TAT AAG CAA GTG GCC CTT GAG TCT CCA TTG GCA TTG   288
Val Asp Arg Ile Tyr Lys Gln Val Ala Leu Glu Ser Pro Leu Ala Leu
                85                  90                  95

TTA AAT ACT GAG ACC ACA ATT ATG AAC GCA ATA ACA TCT CTC TCT TAT   336
Leu Asn Thr Glu Thr Thr Ile Met Asn Ala Ile Thr Ser Leu Ser Tyr
                100                 105                 110
```

| | |
|---|---|
| CAG ATT AAT GGA GCT GCA AAC AAC AGC GGG TGG GGG GCA CCT ATT CAT<br>Gln Ile Asn Gly Ala Ala Asn Asn Ser Gly Trp Gly Ala Pro Ile His<br>               115                       120                       125 | 384 |
| GAC CCA GAT TAT ATA GGG GGG ATA GGC AAA GAA CTC ATT GTA GAT GAT<br>Asp Pro Asp Tyr Ile Gly Gly Ile Gly Lys Glu Leu Ile Val Asp Asp<br>130                       135                       140 | 432 |
| GCT AGT GAT GTC ACA TCA TTC TAT CCC TCT GCA TTT CAA GAA CAT CTG<br>Ala Ser Asp Val Thr Ser Phe Tyr Pro Ser Ala Phe Gln Glu His Leu<br>145                       150                       155                       160 | 480 |
| AAT TTT ATC CCG GCG CCT ACT ACA GGA TCA GGT TGC ACT CGA ATA CCC<br>Asn Phe Ile Pro Ala Pro Thr Thr Gly Ser Gly Cys Thr Arg Ile Pro<br>               165                       170                       175 | 528 |
| TCA TTT GAC ATG AGT GCT ACC CAT TAC TGC TAC ACC CAT AAT GTA ATA<br>Ser Phe Asp Met Ser Ala Thr His Tyr Cys Tyr Thr His Asn Val Ile<br>                   180                       185                       190 | 576 |
| TTG TCT GGA TGC AGA GAT CAC TCA CAC TCA CAT CAG TAT TTA GCA CTT<br>Leu Ser Gly Cys Arg Asp His Ser His Ser His Gln Tyr Leu Ala Leu<br>         195                       200                       205 | 624 |
| GGT GTG CTC CGG ACA TCT GCA ACA GGG AGG GTA TTC TTT TCT ACT CTG<br>Gly Val Leu Arg Thr Ser Ala Thr Gly Arg Val Phe Phe Ser Thr Leu<br>         210                       215                       220 | 672 |
| CGT TCC ATC AAC CTG GAC GAC ACC CAA AAT CGG AAG TCT TGC AGT GTG<br>Arg Ser Ile Asn Leu Asp Asp Thr Gln Asn Arg Lys Ser Cys Ser Val<br>225                       230                       235                       240 | 720 |
| AGT GCA ACT CCC CTG GGT TGT GAT ATG CTG TGC TCG AAA GCC ACG GAG<br>Ser Ala Thr Pro Leu Gly Cys Asp Met Leu Cys Ser Lys Ala Thr Glu<br>                   245                       250                       255 | 768 |
| ACA GAG GAA GAA GAT TAT AAC TCA GCT GTC CCT ACG CGG ATG GTA CAT<br>Thr Glu Glu Glu Asp Tyr Asn Ser Ala Val Pro Thr Arg Met Val His<br>               260                       265                       270 | 816 |
| GGG AGG TTA GGG TTC GAC GGC CAA TAT CAC GAA AAG GAC CTA GAT GTC<br>Gly Arg Leu Gly Phe Asp Gly Gln Tyr His Glu Lys Asp Leu Asp Val<br>         275                       280                       285 | 864 |
|  ACA ACA TTA TTC GGG GAC TGG GTG GCC AAC TAC CCA GGA GTA GGG GGT<br> Thr Thr Leu Phe Gly Asp Trp Val Ala Asn Tyr Pro Gly Val Gly Gly<br>          290                       295                       300 | 912 |
| GGA TCT TTT ATT GAC AGC CGC GTG TGG TTC TCA GTC TAC GGA GGG TTA<br>Gly Ser Phe Ile Asp Ser Arg Val Trp Phe Ser Val Tyr Gly Gly Leu<br>305                       310                       315                       320 | 960 |
| AAA CCC AAT ACA CCC AGT GAC ACT GTA CAG GAA GGG AAA TAT GTG ATA<br>Lys Pro Asn Thr Pro Ser Asp Thr Val Gln Glu Gly Lys Tyr Val Ile<br>                   325                       330                       335 | 1008 |
| TAC AAG CGA TAC AAT GAC ACA TGC CCA GAT GAG CAA GAC TAC CAG ATT<br>Tyr Lys Arg Tyr Asn Asp Thr Cys Pro Asp Glu Gln Asp Tyr Gln Ile<br>               340                       345                       350 | 1056 |
| CGA ATG GCC AAG TCT TCG TAT AAG CCT GGA CGG TTT GGT GGG AAA CGC<br>Arg Met Ala Lys Ser Ser Tyr Lys Pro Gly Arg Phe Gly Gly Lys Arg<br>         355                       360                       365 | 1104 |
| ATA CAG CAG GCT ATC TTA TCT ATC AAA GTG TCA ACA TCC TTA GGC GAA<br>Ile Gln Gln Ala Ile Leu Ser Ile Lys Val Ser Thr Ser Leu Gly Glu<br>         370                       375                       380 | 1152 |
| GAC CCG GTA CTG ACT GTA CCG CCC AAC ACA GTC ACA CTC ATG GGG GCC<br>Asp Pro Val Leu Thr Val Pro Pro Asn Thr Val Thr Leu Met Gly Ala<br>385                       390                       395                       400 | 1200 |
| GAA GGC AGA ATT CTC ACA GTA GGG ACA TCC CAT TTC TTG TAT CAG CGA<br>Glu Gly Arg Ile Leu Thr Val Gly Thr Ser His Phe Leu Tyr Gln Arg<br>                   405                       410                       415 | 1248 |
| GGG TCA TCA TAC TTC TCT CCC GCG TTA TTA TAT CCT ATG ACA GTC AGC<br>Gly Ser Ser Tyr Phe Ser Pro Ala Leu Leu Tyr Pro Met Thr Val Ser<br>         420                       425                       430 | 1296 |

```
AAC AAA ACA GCC ACT CTT CAT AGT CCT TAT ACA TTC AAT GCC TTC ACT    1344
Asn Lys Thr Ala Thr Leu His Ser Pro Tyr Thr Phe Asn Ala Phe Thr
        435                 440                 445

CGG CCA GGT AGT ATC CCT TGC CAG GCT TCA GCA AGA TGC CCC AAC TCA    1392
Arg Pro Gly Ser Ile Pro Cys Gln Ala Ser Ala Arg Cys Pro Asn Ser
    450                 455                 460

TGT GTT ACT GGA GTC TAT ACA GAT CCA TAT CCC CTA ATC TTC TAT AGA    1440
Cys Val Thr Gly Val Tyr Thr Asp Pro Tyr Pro Leu Ile Phe Tyr Arg
465                 470                 475                 480

AAC CAC ACC TTG CGA GGG GTA TTC GGG ACA ATG CTT GAT GGT GAA CAA    1488
Asn His Thr Leu Arg Gly Val Phe Gly Thr Met Leu Asp Gly Glu Gln
                485                 490                 495

GCA AGA CTT AAC CCT GCG TCT GCA GTA TTC GAT AGC ACA TCC CGC AGT    1536
Ala Arg Leu Asn Pro Ala Ser Ala Val Phe Asp Ser Thr Ser Arg Ser
            500                 505                 510

CGC ATA ACT CGA GTG AGT TCA AGC AGC ATC AAA GCA GCA TAC ACA ACA    1584
Arg Ile Thr Arg Val Ser Ser Ser Ser Ile Lys Ala Ala Tyr Thr Thr
        515                 520                 525

TCA ACT TGT TTT AAA GTG GTC AAG ACC AAT AAG ACC TAT TGT CTC AGC    1632
Ser Thr Cys Phe Lys Val Val Lys Thr Asn Lys Thr Tyr Cys Leu Ser
    530                 535                 540

ATT GCT GAA ATA TCT AAT ACT CTC TTC GGA GAA TTC AGA ATC GTC CCG    1680
Ile Ala Glu Ile Ser Asn Thr Leu Phe Gly Glu Phe Arg Ile Val Pro
545                 550                 555                 560

TTA CTA GTT GAG ATC CTC AAA GAT GAC GGG GTT AGA GAA GCC AGG TCT    1728
Leu Leu Val Glu Ile Leu Lys Asp Asp Gly Val Arg Glu Ala Arg Ser
                565                 570                 575

GGC TAG                                                            1734
Gly (2) INFORMATION FOR SEQ ID NO:11:

(i) SEQUENCE CHARACTERISTICS:
        (A) LENGTH: 577 amino acids
        (B) TYPE: amino acid
        (D) TOPOLOGY: linear (ii) MOLECULE TYPE: protein (xi) SEQUENCE DESCRIPTION: SEQ ID NO:11:

Met Asp Arg Ala Val Ser Gln Val Ala Leu Glu Asn Asp Glu Arg Glu
1               5                   10                  15

Ala Lys Asn Thr Trp Arg Leu Ile Phe Arg Ile Ala Ile Leu Phe Leu
            20                  25                  30

Thr Val Val Thr Leu Ala Ile Ser Val Ala Ser Leu Leu Tyr Ser Met
        35                  40                  45

Gly Ala Ser Thr Pro Ser Asp Leu Val Gly Ile Pro Thr Arg Ile Ser
    50                  55                  60

Arg Ala Glu Glu Lys Ile Thr Ser Thr Leu Gly Ser Asn Gln Asp Val
65                  70                  75                  80

Val Asp Arg Ile Tyr Lys Gln Val Ala Leu Glu Ser Pro Leu Ala Leu
                85                  90                  95

Leu Asn Thr Glu Thr Thr Ile Met Asn Ala Ile Thr Ser Leu Ser Tyr
            100                 105                 110

Gln Ile Asn Gly Ala Ala Asn Asn Ser Gly Trp Gly Ala Pro Ile His
        115                 120                 125

Asp Pro Asp Tyr Ile Gly Gly Ile Gly Lys Glu Leu Ile Val Asp Asp
    130                 135                 140

Ala Ser Asp Val Thr Ser Phe Tyr Pro Ser Ala Phe Gln Glu His Leu
145                 150                 155                 160
```

-continued

```
Asn Phe Ile Pro Ala Pro Thr Thr Gly Ser Gly Cys Thr Arg Ile Pro
                165                 170                 175

Ser Phe Asp Met Ser Ala Thr His Tyr Cys Tyr Thr His Asn Val Ile
            180                 185                 190

Leu Ser Gly Cys Arg Asp His Ser His Ser His Gln Tyr Leu Ala Leu
        195                 200                 205

Gly Val Leu Arg Thr Ser Ala Thr Gly Arg Val Phe Phe Ser Thr Leu
    210                 215                 220

Arg Ser Ile Asn Leu Asp Asp Thr Gln Asn Arg Lys Ser Cys Ser Val
225                 230                 235                 240

Ser Ala Thr Pro Leu Gly Cys Asp Met Leu Cys Ser Lys Ala Thr Glu
                245                 250                 255

Thr Glu Glu Glu Asp Tyr Asn Ser Ala Val Pro Thr Arg Met Val His
                260                 265                 270

Gly Arg Leu Gly Phe Asp Gly Gln Tyr His Glu Lys Asp Leu Asp Val
            275                 280                 285

Thr Thr Leu Phe Gly Asp Trp Val Ala Asn Tyr Pro Gly Val Gly Gly
        290                 295                 300

Gly Ser Phe Ile Asp Ser Arg Val Trp Phe Ser Val Tyr Gly Gly Leu
305                 310                 315                 320

Lys Pro Asn Thr Pro Ser Asp Thr Val Gln Glu Gly Lys Tyr Val Ile
                325                 330                 335

Tyr Lys Arg Tyr Asn Asp Thr Cys Pro Asp Glu Gln Asp Tyr Gln Ile
            340                 345                 350

Arg Met Ala Lys Ser Ser Tyr Lys Pro Gly Arg Phe Gly Gly Lys Arg
        355                 360                 365

Ile Gln Gln Ala Ile Leu Ser Ile Lys Val Ser Thr Ser Leu Gly Glu
    370                 375                 380

Asp Pro Val Leu Thr Val Pro Asn Thr Val Thr Leu Met Gly Ala
385                 390                 395                 400

Glu Gly Arg Ile Leu Thr Val Gly Thr Ser His Phe Leu Tyr Gln Arg
                405                 410                 415

Gly Ser Ser Tyr Phe Ser Pro Ala Leu Leu Tyr Pro Met Thr Val Ser
            420                 425                 430

Asn Lys Thr Ala Thr Leu His Ser Pro Tyr Thr Phe Asn Ala Phe Thr
        435                 440                 445

Arg Pro Gly Ser Ile Pro Cys Gln Ala Ser Ala Arg Cys Pro Asn Ser
    450                 455                 460

Cys Val Thr Gly Val Tyr Thr Asp Pro Tyr Pro Leu Ile Phe Tyr Arg
465                 470                 475                 480

Asn His Thr Leu Arg Gly Val Phe Gly Thr Met Leu Asp Gly Glu Gln
                485                 490                 495

Ala Arg Leu Asn Pro Ala Ser Ala Val Phe Asp Ser Thr Ser Arg Ser
            500                 505                 510

Arg Ile Thr Arg Val Ser Ser Ser Ile Lys Ala Ala Tyr Thr Thr
        515                 520                 525

Ser Thr Cys Phe Lys Val Val Lys Thr Asn Lys Thr Tyr Cys Leu Ser
    530                 535                 540

Ile Ala Glu Ile Ser Asn Thr Leu Phe Gly Glu Phe Arg Ile Val Pro
545                 550                 555                 560

Leu Leu Val Glu Ile Leu Lys Asp Asp Gly Val Arg Glu Ala Arg Ser
                565                 570                 575

Gly
```

(2) INFORMATION FOR SEQ ID NO:12:

(i) SEQUENCE CHARACTERISTICS:
        (A) LENGTH: 1662 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION: 1..1662

(xi) SEQUENCE DESCRIPTION: SEQ ID NO:12:

```
ATG GGC TCC AGA CCT TCT ACC AAG AAC CCA GCA CCT ATG ATG CTG ACT        48
Met Gly Ser Arg Pro Ser Thr Lys Asn Pro Ala Pro Met Met Leu Thr
 1               5                  10                  15

ATC CGG GTC GCG CTG GTA CTG AGT TGC ATC TGT CCG GCA AAC TCC ATT        96
Ile Arg Val Ala Leu Val Leu Ser Cys Ile Cys Pro Ala Asn Ser Ile
             20                  25                  30

GAT GGC AGG CCT CTT GCA GCT GCA GGA ATT GTG GTT ACA GGA GAC AAA       144
Asp Gly Arg Pro Leu Ala Ala Ala Gly Ile Val Val Thr Gly Asp Lys
         35                  40                  45

GCA GTC AAC ATA TAC ACC TCA TCC CAG ACA GGA TCA ATC ATA GTT AAG       192
Ala Val Asn Ile Tyr Thr Ser Ser Gln Thr Gly Ser Ile Ile Val Lys
     50                  55                  60

CTC CTC CCG AAT CTG CCA AAG GAT AAG GAG GCA TGT GCG AAA GCC CCC       240
Leu Leu Pro Asn Leu Pro Lys Asp Lys Glu Ala Cys Ala Lys Ala Pro
 65                  70                  75                  80

TTG GAT GCA TAC AAC AGG ACA TTG ACC ACT TTG CTC ACC CCC CTT GGT       288
Leu Asp Ala Tyr Asn Arg Thr Leu Thr Thr Leu Leu Thr Pro Leu Gly
                 85                  90                  95

GAC TCT ATC CGT AGG ATA CAA GAG TCT GTG ACT ACA TCT GGA GGG GGG       336
Asp Ser Ile Arg Arg Ile Gln Glu Ser Val Thr Thr Ser Gly Gly Gly
            100                 105                 110

AGA CAG GGG CGC CTT ATA GGC GCC ATT ATT GGC GGT GTG GCT CTT GGG       384
Arg Gln Gly Arg Leu Ile Gly Ala Ile Ile Gly Gly Val Ala Leu Gly
        115                 120                 125

GTT GCA ACT GCC GCA CAA ATA ACA GCG GCC GCA GCT CTG ATA CAA GCC       432
Val Ala Thr Ala Ala Gln Ile Thr Ala Ala Ala Ala Leu Ile Gln Ala
    130                 135                 140

AAA CAA AAT GCT GCC AAC ATC CTC CGA CTT AAA GAG AGC ATT GCC GCA       480
Lys Gln Asn Ala Ala Asn Ile Leu Arg Leu Lys Glu Ser Ile Ala Ala
145                 150                 155                 160

ACC AAT GAG GCT GTG CAT GAG GTC ACT GAC GGA TTA TCG CAA CTA GCA       528
Thr Asn Glu Ala Val His Glu Val Thr Asp Gly Leu Ser Gln Leu Ala
                165                 170                 175

GTG GCA GTT GGG AAG ATG CAG CAG TTC GTT AAT GAC CAA TTT AAT AAA       576
Val Ala Val Gly Lys Met Gln Gln Phe Val Asn Asp Gln Phe Asn Lys
            180                 185                 190

ACA GCT CAG GAA TTA GAC TGC ATC AAA ATT GCA CAG CAA GTT GGT GTA       624
Thr Ala Gln Glu Leu Asp Cys Ile Lys Ile Ala Gln Gln Val Gly Val
        195                 200                 205

GAG CTC AAC CTG TAC CTA ACC GAA TCG ACT ACA GTA TTC GGA CCA CAA       672
Glu Leu Asn Leu Tyr Leu Thr Glu Ser Thr Thr Val Phe Gly Pro Gln
    210                 215                 220
```

```
ATC ACT TCA CCT GCC TTA AAC AAG CTG ACT ATT CAG GCA CTT TAC AAT      720
Ile Thr Ser Pro Ala Leu Asn Lys Leu Thr Ile Gln Ala Leu Tyr Asn
225             230                 235                 240

CTA GCT GGT GGG AAT ATG GAT TAC TTA TTG ACT AAG TTA GGT ATA GGG      768
Leu Ala Gly Gly Asn Met Asp Tyr Leu Leu Thr Lys Leu Gly Ile Gly
                245                 250                 255

AAC AAT CAA CTC AGC TCA TTA ATC GGT AGC GGC TTA ATC ACC GGT AAC      816
Asn Asn Gln Leu Ser Ser Leu Ile Gly Ser Gly Leu Ile Thr Gly Asn
            260                 265                 270

CCT ATT CTA TAC GAC TCA CAG ACT CAA CTC TTG GGT ATA CAG GTA ACT      864
Pro Ile Leu Tyr Asp Ser Gln Thr Gln Leu Leu Gly Ile Gln Val Thr
        275                 280                 285

CTA CCT TCA GTC GGG AAC CTA AAT AAT ATG CGT GCC ACC TAC TTG GAA      912
Leu Pro Ser Val Gly Asn Leu Asn Asn Met Arg Ala Thr Tyr Leu Glu
    290                 295                 300

ACC TTA TCC GTA AGC ACA ACC AGG GGA TTT GCC TCG GCA CTT GTC CCA      960
Thr Leu Ser Val Ser Thr Thr Arg Gly Phe Ala Ser Ala Leu Val Pro
305                 310                 315                 320

AAA GTG GTG ACA CGG GTC GGT TCT GTG ATA GAA GAA CTT GAC ACC TCA     1008
Lys Val Val Thr Arg Val Gly Ser Val Ile Glu Glu Leu Asp Thr Ser
                325                 330                 335

TAC TGT ATA GAA ACT GAC TTA GAT TTA TAT TGT ACA AGA ATA GTA ACG     1056
Tyr Cys Ile Glu Thr Asp Leu Asp Leu Tyr Cys Thr Arg Ile Val Thr
                340                 345                 350

TTC CCT ATG TCC CCT GGT ATT TAC TCC TGC TTG AGC GGC AAT ACA TCG     1104
Phe Pro Met Ser Pro Gly Ile Tyr Ser Cys Leu Ser Gly Asn Thr Ser
            355                 360                 365

GCC TGT ATG TAC TCA AAG ACC GAA GGC GCA CTT ACT ACA CCA TAT ATG     1152
Ala Cys Met Tyr Ser Lys Thr Glu Gly Ala Leu Thr Thr Pro Tyr Met
        370                 375                 380

ACT ATC AAA GGC TCA GTC ATC GCT AAC TGC AAG ATG ACA ACA TGT AGA     1200
Thr Ile Lys Gly Ser Val Ile Ala Asn Cys Lys Met Thr Thr Cys Arg
385                 390                 395                 400

TGT GTA AAC CCC CCG GGT ATC ATA TCG CAA AAC TAT GGA GAA GCC GTG     1248
Cys Val Asn Pro Pro Gly Ile Ile Ser Gln Asn Tyr Gly Glu Ala Val
                405                 410                 415

TCT CTA ATA GAT AAA CAA TCA TGC AAT GTT TTA TCC TTA GGC GGG ATA     1296
Ser Leu Ile Asp Lys Gln Ser Cys Asn Val Leu Ser Leu Gly Gly Ile
                420                 425                 430

ACT TTA AGG CTC AGT GGG GAA TTC GAT GTA ACT TAT CAG AAG AAT ATC     1344
Thr Leu Arg Leu Ser Gly Glu Phe Asp Val Thr Tyr Gln Lys Asn Ile
            435                 440                 445

TCA ATA CAA GAT TCT CAA GTA ATA ATA ACA GGC AAT CTT GAT ATC TCA     1392
Ser Ile Gln Asp Ser Gln Val Ile Ile Thr Gly Asn Leu Asp Ile Ser
        450                 455                 460

ACT GAG CTT GGG AAT GTC AAC AAC TCG ATC AGT AAT GCC TTG AAT AAG     1440
Thr Glu Leu Gly Asn Val Asn Asn Ser Ile Ser Asn Ala Leu Asn Lys
465                 470                 475                 480

TTA GAG GAA AGC AAC AGA AAA CTA GAC AAA GTC AAT GTC AAA CTG ACC     1488
Leu Glu Glu Ser Asn Arg Lys Leu Asp Lys Val Asn Val Lys Leu Thr
                485                 490                 495

AGC ACA TCT GCT CTC ATT ACC TAT ATC GTT TTG ACT ATC ATA TCT CTT     1536
Ser Thr Ser Ala Leu Ile Thr Tyr Ile Val Leu Thr Ile Ile Ser Leu
                500                 505                 510

GTT TTT GGT ATA CTT AGC CTG ATT CTA GCA TGC TAC CTA ATG TAC AAG     1584
Val Phe Gly Ile Leu Ser Leu Ile Leu Ala Cys Tyr Leu Met Tyr Lys
            515                 520                 525

CAA AAG GCG CAA CAA AAG ACC TTA TTA TGG CTT GGG AAT AAT ACC CTA     1632
Gln Lys Ala Gln Gln Lys Thr Leu Leu Trp Leu Gly Asn Asn Thr Leu
        530                 535                 540
```

```
GAT CAG ATG AGA GCC ACT ACA AAA ATG TGA                                    1662
Asp Gln Met Arg Ala Thr Thr Lys Met
545                 550
```

(2) INFORMATION FOR SEQ ID NO:13:

(i) SEQUENCE CHARACTERISTICS:
        (A) LENGTH: 553 amino acids
        (B) TYPE: amino acid
        (D) TOPOLOGY: linear (ii) MOLECULE TYPE: protein (xi) SEQUENCE DESCRIPTION: SEQ ID NO:13:

```
Met Gly Ser Arg Pro Ser Thr Lys Asn Pro Ala Pro Met Met Leu Thr
1               5                   10                  15

Ile Arg Val Ala Leu Val Leu Ser Cys Ile Cys Pro Ala Asn Ser Ile
                20                  25                  30

Asp Gly Arg Pro Leu Ala Ala Gly Ile Val Val Thr Gly Asp Lys
            35                  40                  45

Ala Val Asn Ile Tyr Thr Ser Ser Gln Thr Gly Ser Ile Ile Val Lys
    50                  55                  60

Leu Leu Pro Asn Leu Pro Lys Asp Lys Glu Ala Cys Ala Lys Ala Pro
65                  70                  75                  80

Leu Asp Ala Tyr Asn Arg Thr Leu Thr Leu Leu Thr Pro Leu Gly
                85                  90                  95

Asp Ser Ile Arg Arg Ile Gln Glu Ser Val Thr Thr Ser Gly Gly Gly
                100                 105                 110

Arg Gln Gly Arg Leu Ile Gly Ala Ile Ile Gly Gly Val Ala Leu Gly
            115                 120                 125

Val Ala Thr Ala Ala Gln Ile Thr Ala Ala Ala Ala Leu Ile Gln Ala
    130                 135                 140

Lys Gln Asn Ala Ala Asn Ile Leu Arg Leu Lys Glu Ser Ile Ala Ala
145                 150                 155                 160

Thr Asn Glu Ala Val His Glu Val Thr Asp Gly Leu Ser Gln Leu Ala
                165                 170                 175

Val Ala Val Gly Lys Met Gln Gln Phe Val Asn Asp Gln Phe Asn Lys
            180                 185                 190

Thr Ala Gln Glu Leu Asp Cys Ile Lys Ile Ala Gln Gln Val Gly Val
    195                 200                 205

Glu Leu Asn Leu Tyr Leu Thr Glu Ser Thr Thr Val Phe Gly Pro Gln
210                 215                 220

Ile Thr Ser Pro Ala Leu Asn Lys Leu Thr Ile Gln Ala Leu Tyr Asn
225                 230                 235                 240

Leu Ala Gly Gly Asn Met Asp Tyr Leu Leu Thr Lys Leu Gly Ile Gly
                245                 250                 255

Asn Asn Gln Leu Ser Ser Leu Ile Gly Ser Gly Leu Ile Thr Gly Asn
            260                 265                 270

Pro Ile Leu Tyr Asp Ser Gln Thr Gln Leu Leu Gly Ile Gln Val Thr
    275                 280                 285

Leu Pro Ser Val Gly Asn Leu Asn Asn Met Arg Ala Thr Tyr Leu Glu
290                 295                 300

Thr Leu Ser Val Ser Thr Thr Arg Gly Phe Ala Ser Ala Leu Val Pro
305                 310                 315                 320

Lys Val Val Thr Arg Val Gly Ser Val Ile Glu Glu Leu Asp Thr Ser
                325                 330                 335
```

```
Tyr Cys Ile Glu Thr Asp Leu Asp Leu Tyr Cys Thr Arg Ile Val Thr
            340                 345                 350

Phe Pro Met Ser Pro Gly Ile Tyr Ser Cys Leu Ser Gly Asn Thr Ser
            355                 360                 365

Ala Cys Met Tyr Ser Lys Thr Glu Gly Ala Leu Thr Thr Pro Tyr Met
            370                 375                 380

Thr Ile Lys Gly Ser Val Ile Ala Asn Cys Lys Met Thr Thr Cys Arg
385                 390                 395                 400

Cys Val Asn Pro Pro Gly Ile Ile Ser Gln Asn Tyr Gly Glu Ala Val
            405                 410                 415

Ser Leu Ile Asp Lys Gln Ser Cys Asn Val Leu Ser Leu Gly Gly Ile
            420                 425                 430

Thr Leu Arg Leu Ser Gly Glu Phe Asp Val Thr Tyr Gln Lys Asn Ile
            435                 440                 445

Ser Ile Gln Asp Ser Gln Val Ile Ile Thr Gly Asn Leu Asp Ile Ser
            450                 455                 460

Thr Glu Leu Gly Asn Val Asn Asn Ser Ile Ser Asn Ala Leu Asn Lys
465                 470                 475                 480

Leu Glu Glu Ser Asn Arg Lys Leu Asp Lys Val Asn Val Lys Leu Thr
            485                 490                 495

Ser Thr Ser Ala Leu Ile Thr Tyr Ile Val Leu Thr Ile Ile Ser Leu
            500                 505                 510

Val Phe Gly Ile Leu Ser Leu Ile Leu Ala Cys Tyr Leu Met Tyr Lys
            515                 520                 525

Gln Lys Ala Gln Gln Lys Thr Leu Leu Trp Leu Gly Asn Asn Thr Leu
            530                 535                 540

Asp Gln Met Arg Ala Thr Thr Lys Met
545                 550
```

(2) INFORMATION FOR SEQ ID NO:14:

(i) SEQUENCE CHARACTERISTICS:
        (A) LENGTH: 3489 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION: 1..3489

(xi) SEQUENCE DESCRIPTION: SEQ ID NO:14:

```
ATG TTG GTA ACA CCT CTT TTA CTA GTG ACT CTT TTG TGT GTA CTA TGT      48
Met Leu Val Thr Pro Leu Leu Leu Val Thr Leu Leu Cys Val Leu Cys
1               5                   10                  15

AGT GCT GCT TTG TAT GAC AGT AGT TCT TAC GTT TAC TAC CAA AGT          96
Ser Ala Ala Leu Tyr Asp Ser Ser Ser Tyr Val Tyr Tyr Gln Ser
                20                  25                  30

GCC TTT AGA CCA CCT AAT GGT TGG CAT TTA CAC GGG GGT GCT TAT GCG     144
Ala Phe Arg Pro Pro Asn Gly Trp His Leu His Gly Gly Ala Tyr Ala
            35                  40                  45

GTA GTT AAT ATT TCT AGC GAA TCT AAT AAT GCA GGC TCT TCA CCT GGG     192
Val Val Asn Ile Ser Ser Glu Ser Asn Asn Ala Gly Ser Ser Pro Gly
        50                  55                  60
```

```
TGT ATT GTT GGT ACT ATT CAT GGT GGT CGT GTT GTT AAT GCT TCT TCT        240
Cys Ile Val Gly Thr Ile His Gly Gly Arg Val Val Asn Ala Ser Ser
 65              70                  75                  80

ATA GCT ATG ACG GCA CCG TCA TCA GGT ATG GCT TGG TCT AGC AGT CAG        288
Ile Ala Met Thr Ala Pro Ser Ser Gly Met Ala Trp Ser Ser Ser Gln
             85                  90                  95

TTT TGT ACT GCA CAC TGT AAC TTT TCA GAT ACT ACA GTG TTT GTT ACA        336
Phe Cys Thr Ala His Cys Asn Phe Ser Asp Thr Thr Val Phe Val Thr
                100                 105                 110

CAT TGT TAT AAA TAT GAT GGG TGT CCT ATA ACT GGC ATG CTT CAA AAG        384
His Cys Tyr Lys Tyr Asp Gly Cys Pro Ile Thr Gly Met Leu Gln Lys
            115                 120                 125

AAT TTT TTA CGT GTT TCT GCT ATG AAA AAT GGC CAG CTT TTC TAT AAT        432
Asn Phe Leu Arg Val Ser Ala Met Lys Asn Gly Gln Leu Phe Tyr Asn
        130                 135                 140

TTA ACA GTT AGT GTA GCT AAG TAC CCT ACT TTT AAA TCA TTT CAG TGT        480
Leu Thr Val Ser Val Ala Lys Tyr Pro Thr Phe Lys Ser Phe Gln Cys
145                 150                 155                 160

GTT AAT AAT TTA ACA TCC GTA TAT TTA AAT GGT GAT CTT GTT TAC ACC        528
Val Asn Asn Leu Thr Ser Val Tyr Leu Asn Gly Asp Leu Val Tyr Thr
                165                 170                 175

TCT AAT GAG ACC ACA GAT GTT ACA TCT GCA GGT GTT TAT TTT AAA GCT        576
Ser Asn Glu Thr Thr Asp Val Thr Ser Ala Gly Val Tyr Phe Lys Ala
                180                 185                 190

GGT GGA CCT ATA ACT TAT AAA GTT ATG AGA AAA GTT AAA GCC CTG GCT        624
Gly Gly Pro Ile Thr Tyr Lys Val Met Arg Lys Val Lys Ala Leu Ala
            195                 200                 205

TAT TTT GTT AAT GGT ACT GCA CAA GAT GTT ATT TTG TGT GAT GGA TCA        672
Tyr Phe Val Asn Gly Thr Ala Gln Asp Val Ile Leu Cys Asp Gly Ser
        210                 215                 220

CCT AGA GGC TTG TTA GCA TGC CAG TAT AAT ACT GGC AAT TTT TCA GAT        720
Pro Arg Gly Leu Leu Ala Cys Gln Tyr Asn Thr Gly Asn Phe Ser Asp
225                 230                 235                 240

GGC TTT TAT CCT TTT ATT AAT AGT AGT TTA GTT AAG CAG AAG TTT ATT        768
Gly Phe Tyr Pro Phe Ile Asn Ser Ser Leu Val Lys Gln Lys Phe Ile
                245                 250                 255

GTC TAT CGT GAA AAT AGT GTT AAT ACT ACT TTT ACG TTA CAC AAT TTC    816
Val Tyr Arg Glu Asn Ser Val Asn Thr Thr Phe Thr Leu His Asn Phe
                260                 265                 270

ACT TTT CAT AAT GAG ACT GGC GCC AAC CCT AAT CCT AGT GGT GTT CAG        864
Thr Phe His Asn Glu Thr Gly Ala Asn Pro Asn Pro Ser Gly Val Gln
            275                 280                 285

AAT ATT CTA ACT TAC CAA ACA CAA ACA GCT CAG AGT GGT TAT TAT AAT        912
Asn Ile Leu Thr Tyr Gln Thr Gln Thr Ala Gln Ser Gly Tyr Tyr Asn
        290                 295                 300

TTT AAT TTT TCC TTT CTG AGT AGT TTT GTT TAT AAG GAG TCT AAT TTT        960
Phe Asn Phe Ser Phe Leu Ser Ser Phe Val Tyr Lys Glu Ser Asn Phe
305                 310                 315                 320

ATG TAT GGA TCT TAT CAC CCA AGT TGT AAT TTT AGA CTA GAA ACT ATT       1008
Met Tyr Gly Ser Tyr His Pro Ser Cys Asn Phe Arg Leu Glu Thr Ile
                325                 330                 335

AAT AAT GGC TTG TGG TTT AAT TCA CTT TCA GTT TCA ATT GCT TAC GGT       1056
Asn Asn Gly Leu Trp Phe Asn Ser Leu Ser Val Ser Ile Ala Tyr Gly
            340                 345                 350

CCT CTT CAA GGT GGT TGC AAG CAA TCT GTC TTT AGT GGT AGA GCA ACT       1104
Pro Leu Gln Gly Gly Cys Lys Gln Ser Val Phe Ser Gly Arg Ala Thr
        355                 360                 365

TGT TGT TAT GCT TAT TCA TAT GGA GGT CCT TCG CTG TGT AAA GGT GTT       1152
Cys Cys Tyr Ala Tyr Ser Tyr Gly Gly Pro Ser Leu Cys Lys Gly Val
370                 375                 380
```

-continued

| | |
|---|---|
| TAT TCA GGT GAG TTA GAT CTT AAT TTT GAA TGT GGA CTG TTA GTT TAT<br>Tyr Ser Gly Glu Leu Asp Leu Asn Phe Glu Cys Gly Leu Leu Val Tyr<br>385                                     390                          395                          400 | 1200 |
| GTT ACT AAG AGC GGT GGC TCT CGT ATA CAA ACA GCC ACT GAA CCG CCA<br>Val Thr Lys Ser Gly Gly Ser Arg Ile Gln Thr Ala Thr Glu Pro Pro<br>                                405                          410                               415 | 1248 |
| GTT ATA ACT CGA CAC AAT TAT AAT AAT ATT ACT TTA AAT ACT TGT GTT<br>Val Ile Thr Arg His Asn Tyr Asn Asn Ile Thr Leu Asn Thr Cys Val<br>                     420                               425                          430 | 1296 |
| GAT TAT AAT ATA TAT GGC AGA ACT GGC CAA GGT TTT ATT ACT AAT GTA<br>Asp Tyr Asn Ile Tyr Gly Arg Thr Gly Gln Gly Phe Ile Thr Asn Val<br>                   435                          440                              445 | 1344 |
| ACC GAC TCA GCT GTT AGT TAT AAT TAT CTA GCA GAC GCA GGT TTG GCT<br>Thr Asp Ser Ala Val Ser Tyr Asn Tyr Leu Ala Asp Ala Gly Leu Ala<br>450                                     455                          460 | 1392 |
| ATT TTA GAT ACA TCT GGT TCC ATA GAC ATC TTT GTT GTA CAA GGT GAA<br>Ile Leu Asp Thr Ser Gly Ser Ile Asp Ile Phe Val Val Gln Gly Glu<br>465                                   470                          475                          480 | 1440 |
| TAT GGT CTT ACT TAT TAT AAG GTT AAC CCT TGC GAA GAT GTC AAC CAG<br>Tyr Gly Leu Thr Tyr Tyr Lys Val Asn Pro Cys Glu Asp Val Asn Gln<br>                              485                          490                            495 | 1488 |
| CAG TTT GTA GTT TCT GGT GGT AAA TTA GTA GGT ATT CTT ACT TCA CGT<br>Gln Phe Val Val Ser Gly Gly Lys Leu Val Gly Ile Leu Thr Ser Arg<br>             500                                   505                              510 | 1536 |
| AAT GAG ACT GGT TCT CAG CTT CTT GAG AAC CAG TTT TAC ATT AAA ATC<br>Asn Glu Thr Gly Ser Gln Leu Leu Glu Asn Gln Phe Tyr Ile Lys Ile<br>                   515                          520                          525 | 1584 |
| ACT AAT GGA ACA CGT CGT TTT AGA CGT TCT ATT ACT GAA AAT GTT GCA<br>Thr Asn Gly Thr Arg Arg Phe Arg Arg Ser Ile Thr Glu Asn Val Ala<br>530                                     535                          540 | 1632 |
| AAT TGC CCT TAT GTT AGT TAT GGT AAG TTT TGT ATA AAA CCT GAT GGT<br>Asn Cys Pro Tyr Val Ser Tyr Gly Lys Phe Cys Ile Lys Pro Asp Gly<br>545                                   550                          555                          560 | 1680 |
| TCA ATT GCC ACA ATA GTA CCA AAA CAA TTG GAA CAG TTT GTG GCA CCT<br>Ser Ile Ala Thr Ile Val Pro Lys Gln Leu Glu Gln Phe Val Ala Pro<br>                            565                          570                          575 | 1728 |
| TTA CTT AAT GTT ACT GAA AAT GTG CTC ATA CCT AAC AGT TTT AAT TTA<br>Leu Leu Asn Val Thr Glu Asn Val Leu Ile Pro Asn Ser Phe Asn Leu<br>                     580                             585                          590 | 1776 |
| ACT GTT ACA GAT GAG TAC ATA CAA ACG CGT ATG GAT AAG GTC CAA ATT<br>Thr Val Thr Asp Glu Tyr Ile Gln Thr Arg Met Asp Lys Val Gln Ile<br>                  595                          600                          605 | 1824 |
| AAT TGT CTG CAG TAT GTT TGT GGC AAT TCT CTG GAT TGT AGA GAT TTG<br>Asn Cys Leu Gln Tyr Val Cys Gly Asn Ser Leu Asp Cys Arg Asp Leu<br>610                                   615                          620 | 1872 |
| TTT CAA CAA TAT GGG CCT GTT TGT GAC AAC ATA TTG TCT GTA GTA AAT<br>Phe Gln Gln Tyr Gly Pro Val Cys Asp Asn Ile Leu Ser Val Val Asn<br>625                                   630                          635                          640 | 1920 |
| AGT ATT GGT CAA AAA GAA GAT ATG GAA CTT TTG AAT TTC TAT TCT TCT<br>Ser Ile Gly Gln Lys Glu Asp Met Glu Leu Leu Asn Phe Tyr Ser Ser<br>                   645                          650                          655 | 1968 |
| ACT AAA CCG GCT GGT TTT AAT ACA CCA TTT CTT AGT AAT GTT AGC ACT<br>Thr Lys Pro Ala Gly Phe Asn Thr Pro Phe Leu Ser Asn Val Ser Thr<br>                                660                          665                          670 | 2016 |
| GGT GAG TTT AAT ATT TCT CTT CTG TTA ACA ACT CCT AGT AGT CCT AGA<br>Gly Glu Phe Asn Ile Ser Leu Leu Leu Thr Thr Pro Ser Ser Pro Arg<br>             675                                 680                              685 | 2064 |
| AGG CGT TCT TTT ATT GAA GAC CTT CTA TTT ACA AGC GTT GAA TCT GTT<br>Arg Arg Ser Phe Ile Glu Asp Leu Leu Phe Thr Ser Val Glu Ser Val<br>                   690                          695                          700 | 2112 |

```
GGA TTA CCA ACA GAT GAC GCA TAC AAA AAT TGC ACT GCA GGA CCT TTA      2160
Gly Leu Pro Thr Asp Asp Ala Tyr Lys Asn Cys Thr Ala Gly Pro Leu
705                 710                 715                 720

GGT TTT CTT AAG GAC CTT GCG TGT GCT CGT GAA TAT AAT GGT TTG CTT      2208
Gly Phe Leu Lys Asp Leu Ala Cys Ala Arg Glu Tyr Asn Gly Leu Leu
                725                 730                 735

GTG TTG CCT CCC ATT ATA ACA GCA GAA ATG CAA ACT TTG TAT ACT AGT      2256
Val Leu Pro Pro Ile Ile Thr Ala Glu Met Gln Thr Leu Tyr Thr Ser
            740                 745                 750

TCT CTA GTA GCT TCT ATG GCT TTT GGT GGT ATT ACT GCA GCT GGT GCT      2304
Ser Leu Val Ala Ser Met Ala Phe Gly Gly Ile Thr Ala Ala Gly Ala
                755                 760                 765

ATA CCT TTT GCC ACA CAA CTG CAG GCT AGA ATT AAT CAC TTG GGT ATT      2352
Ile Pro Phe Ala Thr Gln Leu Gln Ala Arg Ile Asn His Leu Gly Ile
        770                 775                 780

ACC CAG TCA CTT TTG TTG AAG AAT CAA GAA AAA ATT GCT GCT TCC TTT      2400
Thr Gln Ser Leu Leu Leu Lys Asn Gln Glu Lys Ile Ala Ala Ser Phe
785                 790                 795                 800

AAT AAG GCC ATT GGT CGT ATG CAG GAA GGT TTT AGA AGT ACA TCT CTA      2448
Asn Lys Ala Ile Gly Arg Met Gln Glu Gly Phe Arg Ser Thr Ser Leu
                805                 810                 815

GCA TTA CAA CAA ATT CAA GAT GTT GTT AAT AAG CAG AGT GCT ATT CTT      2496
Ala Leu Gln Gln Ile Gln Asp Val Val Asn Lys Gln Ser Ala Ile Leu
            820                 825                 830

ACT GAG ACT ATG GCA TCA CTT AAT AAA AAT TTT GGT GCT ATT TCT TCT      2544
Thr Glu Thr Met Ala Ser Leu Asn Lys Asn Phe Gly Ala Ile Ser Ser
                835                 840                 845

GTG ATT CAA GAA ATC TAC CAG CAA CTT GAC GCC ATA CAA GCA AAT GCT  2592
Val Ile Gln Glu Ile Tyr Gln Gln Leu Asp Ala Ile Gln Ala Asn Ala
        850                 855                 860

CAA GTG GAT CGT CTT ATA ACT GGT AGA TTG TCA TCA CTT TCT GTT TTA      2640
Gln Val Asp Arg Leu Ile Thr Gly Arg Leu Ser Ser Leu Ser Val Leu
865                 870                 875                 880

GCA TCT GCT AAG CAG GCG GAG CAT ATT AGA GTG TCA CAA CAG CGT GAG      2688
Ala Ser Ala Lys Gln Ala Glu His Ile Arg Val Ser Gln Gln Arg Glu
                885                 890                 895

TTA GCT ACT CAG AAA ATT AAT GAG TGT GTT AAG TCA CAG TCT ATT AGG      2736
Leu Ala Thr Gln Lys Ile Asn Glu Cys Val Lys Ser Gln Ser Ile Arg
            900                 905                 910

TAC TCC TTT TGT GGT AAT GGA CGA CAT GTT CTA ACC ATA CCG CAA AAT      2784
Tyr Ser Phe Cys Gly Asn Gly Arg His Val Leu Thr Ile Pro Gln Asn
                915                 920                 925

GCA CCT AAT GGT ATA GTG TTT ATA CAC TTT TCT TAT ACT CCA GAT AGT      2832
Ala Pro Asn Gly Ile Val Phe Ile His Phe Ser Tyr Thr Pro Asp Ser
        930                 935                 940

TTT GTT AAT GTT ACT GCA ATA GTG GGT TTT TGT GTA AAG CCA GCT AAT      2880
Phe Val Asn Val Thr Ala Ile Val Gly Phe Cys Val Lys Pro Ala Asn
945                 950                 955                 960

GCT AGT CAG TAT GCA ATA GTA CCC GCT AAT GGT AGG GGT ATT TTT ATA      2928
 Ala Ser Gln Tyr Ala Ile Val Pro Ala Asn Gly Arg Gly Ile Phe Ile
                965                 970                 975

CAA GTT AAT GGT AGT TAC TAC ATC ACA GCA CGA GAT ATG TAT ATG CCA      2976
Gln Val Asn Gly Ser Tyr Tyr Ile Thr Ala Arg Asp Met Tyr Met Pro
            980                 985                 990

AGA GCT ATT ACT GCA GGA GAT ATA GTT ACG CTT ACT TCT TGT CAA GCA      3024
Arg Ala Ile Thr Ala Gly Asp Ile Val Thr Leu Thr Ser Cys Gln Ala
                995                 1000                1005

AAT TAT GTA AGT GTA AAT AAG ACC GTC ATT ACT ACA TTC GTA GAC AAT      3072
Asn Tyr Val Ser Val Asn Lys Thr Val Ile Thr Thr Phe Val Asp Asn
        1010                1015                1020
```

```
GAT GAT TTT GAT TTT AAT GAC GAA TTG TCA AAA TGG TGG AAT GAC ACT    3120
Asp Asp Phe Asp Phe Asn Asp Glu Leu Ser Lys Trp Trp Asn Asp Thr
1025                1030                1035                1040

AAG CAT GAG CTA CCA GAC TTT GAC AAA TTC AAT TAC ACA GTA CCT ATA    3168
Lys His Glu Leu Pro Asp Phe Asp Lys Phe Asn Tyr Thr Val Pro Ile
                1045                1050                1055

CTT GAC ATT GAT AGT GAA ATT GAT CGT ATT CAA GGC GTT ATA CAG GGT    3216
Leu Asp Ile Asp Ser Glu Ile Asp Arg Ile Gln Gly Val Ile Gln Gly
            1060                1065                1070

CTT AAT GAC TCT TTA ATA GAC CTT GAA AAA CTT TCA ATA CTC AAA ACT    3264
Leu Asn Asp Ser Leu Ile Asp Leu Glu Lys Leu Ser Ile Leu Lys Thr
        1075                1080                1085

TAT ATT AAG TGG CCT TGG TAT GTG TGG TTA GCC ATA GCT TTT GCC ACT    3312
Tyr Ile Lys Trp Pro Trp Tyr Val Trp Leu Ala Ile Ala Phe Ala Thr
    1090                1095                1100

ATT ATC TTC ATC TTA ATA CTA GGA TGG GTT TTC TTC ATG ACT GGA TGT    3360
Ile Ile Phe Ile Leu Ile Leu Gly Trp Val Phe Phe Met Thr Gly Cys
1105                1110                1115                1120

TGT GGT TGT TGT TGT GGA TGC TTT GGC ATT ATG CCT CTA ATG AGT AAG    3408
Cys Gly Cys Cys Cys Gly Cys Phe Gly Ile Met Pro Leu Met Ser Lys
                1125                1130                1135

TGT GGT AAG AAA TCT TCT TAT TAC ACG ACT TTT GAT AAC GAT GTG GTA    3456
Cys Gly Lys Lys Ser Ser Tyr Tyr Thr Thr Phe Asp Asn Asp Val Val
            1140                1145                1150

ACT GAA CAA AAC AGA CCT AAA AAG TCT GTT TAA                        3489
Thr Glu Gln Asn Arg Pro Lys Lys Ser Val
        1155                1160

(2) INFORMATION FOR SEQ ID NO:15:

(i) SEQUENCE CHARACTERISTICS:
        (A) LENGTH: 1162 amino acids
        (B) TYPE: amino acid
        (D) TOPOLOGY: linear (ii) MOLECULE TYPE: protein (xi) SEQUENCE DESCRIPTION: SEQ ID NO:15:

Met Leu Val Thr Pro Leu Leu Val Thr Leu Leu Cys Val Leu Cys
 1               5                  10                  15

Ser Ala Ala Leu Tyr Asp Ser Ser Tyr Val Tyr Tyr Gln Ser
            20                  25                  30

Ala Phe Arg Pro Pro Asn Gly Trp His Leu His Gly Gly Ala Tyr Ala
            35                  40                  45

Val Val Asn Ile Ser Ser Glu Ser Asn Asn Ala Gly Ser Ser Pro Gly
        50                  55                  60

Cys Ile Val Gly Thr Ile His Gly Gly Arg Val Val Asn Ala Ser Ser
 65                 70                  75                  80

Ile Ala Met Thr Ala Pro Ser Ser Gly Met Ala Trp Ser Ser Ser Gln
                85                  90                  95

Phe Cys Thr Ala His Cys Asn Phe Ser Asp Thr Thr Val Phe Val Thr
            100                 105                 110

His Cys Tyr Lys Tyr Asp Gly Cys Pro Ile Thr Gly Met Leu Gln Lys
            115                 120                 125

Asn Phe Leu Arg Val Ser Ala Met Lys Asn Gly Gln Leu Phe Tyr Asn
        130                 135                 140

Leu Thr Val Ser Val Ala Lys Tyr Pro Thr Phe Lys Ser Phe Gln Cys
145                 150                 155                 160

Val Asn Asn Leu Thr Ser Val Tyr Leu Asn Gly Asp Leu Val Tyr Thr
                165                 170                 175
```

-continued

```
Ser Asn Glu Thr Thr Asp Val Thr Ser Ala Gly Val Tyr Phe Lys Ala
            180                 185                 190

Gly Gly Pro Ile Thr Tyr Lys Val Met Arg Lys Val Lys Ala Leu Ala
            195                 200                 205

Tyr Phe Val Asn Gly Thr Ala Gln Asp Val Ile Leu Cys Asp Gly Ser
            210                 215                 220

Pro Arg Gly Leu Leu Ala Cys Gln Tyr Asn Thr Gly Asn Phe Ser Asp
225                 230                 235                 240

Gly Phe Tyr Pro Phe Ile Asn Ser Ser Leu Val Lys Gln Lys Phe Ile
                245                 250                 255

Val Tyr Arg Glu Asn Ser Val Asn Thr Thr Phe Thr Leu His Asn Phe
            260                 265                 270

Thr Phe His Asn Glu Thr Gly Ala Asn Pro Asn Pro Ser Gly Val Gln
            275                 280                 285

Asn Ile Leu Thr Tyr Gln Thr Gln Thr Ala Gln Ser Gly Tyr Tyr Asn
            290                 295                 300

Phe Asn Phe Ser Phe Leu Ser Ser Phe Val Tyr Lys Glu Ser Asn Phe
305                 310                 315                 320

Met Tyr Gly Ser Tyr His Pro Ser Cys Asn Phe Arg Leu Glu Thr Ile
                325                 330                 335

Asn Asn Gly Leu Trp Phe Asn Ser Leu Ser Val Ser Ile Ala Tyr Gly
            340                 345                 350

Pro Leu Gln Gly Gly Cys Lys Gln Ser Val Phe Ser Gly Arg Ala Thr
            355                 360                 365

Cys Cys Tyr Ala Tyr Ser Tyr Gly Gly Pro Ser Leu Cys Lys Gly Val
            370                 375                 380

Tyr Ser Gly Glu Leu Asp Leu Asn Phe Glu Cys Gly Leu Leu Val Tyr
385                 390                 395                 400

Val Thr Lys Ser Gly Gly Ser Arg Ile Gln Thr Ala Thr Glu Pro Pro
            405                 410                 415

Val Ile Thr Arg His Asn Tyr Asn Asn Ile Thr Leu Asn Thr Cys Val
            420                 425                 430

Asp Tyr Asn Ile Tyr Gly Arg Thr Gly Gln Gly Phe Ile Thr Asn Val
            435                 440                 445

Thr Asp Ser Ala Val Ser Tyr Asn Tyr Leu Ala Asp Ala Gly Leu Ala
            450                 455                 460

Ile Leu Asp Thr Ser Gly Ser Ile Asp Ile Phe Val Val Gln Gly Glu
465                 470                 475                 480

Tyr Gly Leu Thr Tyr Tyr Lys Val Asn Pro Cys Glu Asp Val Asn Gln
                485                 490                 495

Gln Phe Val Val Ser Gly Gly Lys Leu Val Gly Ile Leu Thr Ser Arg
            500                 505                 510

Asn Glu Thr Gly Ser Gln Leu Leu Glu Asn Gln Phe Tyr Ile Lys Ile
            515                 520                 525

Thr Asn Gly Thr Arg Arg Phe Arg Arg Ser Ile Thr Glu Asn Val Ala
            530                 535                 540

Asn Cys Pro Tyr Val Ser Tyr Gly Lys Phe Cys Ile Lys Pro Asp Gly
545                 550                 555                 560

Ser Ile Ala Thr Ile Val Pro Lys Gln Leu Glu Gln Phe Val Ala Pro
                565                 570                 575

Leu Leu Asn Val Thr Glu Asn Val Leu Ile Pro Asn Ser Phe Asn Leu
            580                 585                 590
```

-continued

```
Thr Val Thr Asp Glu Tyr Ile Gln Thr Arg Met Asp Lys Val Gln Ile
        595                 600                 605

Asn Cys Leu Gln Tyr Val Cys Gly Asn Ser Leu Asp Cys Arg Asp Leu
        610                 615                 620

Phe Gln Gln Tyr Gly Pro Val Cys Asp Asn Ile Leu Ser Val Val Asn
625                 630                 635                 640

Ser Ile Gly Gln Lys Glu Asp Met Glu Leu Leu Asn Phe Tyr Ser Ser
            645                 650                 655

Thr Lys Pro Ala Gly Phe Asn Thr Pro Phe Leu Ser Asn Val Ser Thr
            660                 665                 670

Gly Glu Phe Asn Ile Ser Leu Leu Leu Thr Pro Ser Ser Pro Arg
            675                 680                 685

Arg Arg Ser Phe Ile Glu Asp Leu Leu Phe Thr Ser Val Glu Ser Val
        690                 695                 700

Gly Leu Pro Thr Asp Asp Ala Tyr Lys Asn Cys Thr Ala Gly Pro Leu
705                 710                 715                 720

Gly Phe Leu Lys Asp Leu Ala Cys Ala Arg Glu Tyr Asn Gly Leu Leu
                725                 730                 735

Val Leu Pro Pro Ile Ile Thr Ala Glu Met Gln Thr Leu Tyr Thr Ser
                740                 745                 750

Ser Leu Val Ala Ser Met Ala Phe Gly Gly Ile Thr Ala Ala Gly Ala
            755                 760                 765

Ile Pro Phe Ala Thr Gln Leu Gln Ala Arg Ile Asn His Leu Gly Ile
        770                 775                 780

Thr Gln Ser Leu Leu Leu Lys Asn Gln Glu Lys Ile Ala Ala Ser Phe
785                 790                 795                 800

Asn Lys Ala Ile Gly Arg Met Gln Glu Gly Phe Arg Ser Thr Ser Leu
                805                 810                 815

Ala Leu Gln Gln Ile Gln Asp Val Val Asn Lys Gln Ser Ala Ile Leu
            820                 825                 830

Thr Glu Thr Met Ala Ser Leu Asn Lys Asn Phe Gly Ala Ile Ser Ser
        835                 840                 845

Val Ile Gln Glu Ile Tyr Gln Gln Leu Asp Ala Ile Gln Ala Asn Ala
        850                 855                 860

Gln Val Asp Arg Leu Ile Thr Gly Arg Leu Ser Ser Leu Ser Val Leu
865                 870                 875                 880

Ala Ser Ala Lys Gln Ala Glu His Ile Arg Val Ser Gln Gln Arg Glu
                885                 890                 895

Leu Ala Thr Gln Lys Ile Asn Glu Cys Val Lys Ser Gln Ser Ile Arg
            900                 905                 910

Tyr Ser Phe Cys Gly Asn Gly Arg His Val Leu Thr Ile Pro Gln Asn
        915                 920                 925

Ala Pro Asn Gly Ile Val Phe Ile His Phe Ser Tyr Thr Pro Asp Ser
930                 935                 940

Phe Val Asn Val Thr Ala Ile Val Gly Phe Cys Val Lys Pro Ala Asn
945                 950                 955                 960

Ala Ser Gln Tyr Ala Ile Val Pro Ala Asn Gly Arg Gly Ile Phe Ile
                965                 970                 975

Gln Val Asn Gly Ser Tyr Tyr Ile Thr Ala Arg Asp Met Tyr Met Pro
            980                 985                 990

Arg Ala Ile Thr Ala Gly Asp Ile Val Thr Leu Thr Ser Cys Gln Ala
        995                 1000                1005

Asn Tyr Val Ser Val Asn Lys Thr Val Ile Thr Thr Phe Val Asp Asn
        1010                1015                1020
```

```
Asp Asp Phe Asp Phe Asn Asp Glu Leu Ser Lys Trp Trp Asn Asp Thr
1025                1030                1035                1040

Lys His Glu Leu Pro Asp Phe Asp Lys Phe Asn Tyr Thr Val Pro Ile
                1045                1050                1055

Leu Asp Ile Asp Ser Glu Ile Asp Arg Ile Gln Gly Val Ile Gln Gly
                1060                1065                1070

Leu Asn Asp Ser Leu Ile Asp Leu Glu Lys Leu Ser Ile Leu Lys Thr
                1075                1080                1085

Tyr Ile Lys Trp Pro Trp Tyr Val Trp Leu Ala Ile Ala Phe Ala Thr
                1090                1095                1100

Ile Ile Phe Ile Leu Ile Leu Gly Trp Val Phe Phe Met Thr Gly Cys
                1105                1110                1115                1120

Cys Gly Cys Cys Cys Gly Cys Phe Gly Ile Met Pro Leu Met Ser Lys
                1125                1130                1135

Cys Gly Lys Ser Ser Tyr Tyr Thr Thr Phe Asp Asn Asp Val Val
                1140                1145                1150

Thr Glu Gln Asn Arg Pro Lys Lys Ser Val
                1155                1160

(2) INFORMATION FOR SEQ ID NO:16:

(i) SEQUENCE CHARACTERISTICS:
        (A) LENGTH: 1846 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION: 1..1846

(xi) SEQUENCE DESCRIPTION: SEQ ID NO:16:

ATG TTG GTG AAG TCA CTG TTT CTA GTG ACC ATT TTG TTT GCA CTA TGT        48
Met Leu Val Lys Ser Leu Phe Leu Val Thr Ile Leu Phe Ala Leu Cys
 1               5                  10                  15

AGT GCT AAT TTA TAT GAC AAC GAA TCT TTT GTG TAT TAC TAC CAG AGT        96
Ser Ala Asn Leu Tyr Asp Asn Glu Ser Phe Val Tyr Tyr Tyr Gln Ser
            20                  25                  30

GCT TTT AGG CCA GGA CAT GGT TGG CAT TTA CAT GGA GGT GCT TAT GCA       144
Ala Phe Arg Pro Gly His Gly Trp His Leu His Gly Gly Ala Tyr Ala
        35                  40                  45

GTA GTT AAT GTG TCT AGT GAA AAT AAT AAT GCA GGT ACT GCC CCA AGT       192
Val Val Asn Val Ser Ser Glu Asn Asn Asn Ala Gly Thr Ala Pro Ser
    50                  55                  60

TGC ACT GCT GGT GCT ATT GGC TAC AGT AAG AAT TTC AGT GCG GCC TCA       240
Cys Thr Ala Gly Ala Ile Gly Tyr Ser Lys Asn Phe Ser Ala Ala Ser
65                  70                  75                  80

GTA GCC ATG ACT GCA CCA CTA AGT GGT ATG TCA TGG TCT GCC TCA TCT       288
Val Ala Met Thr Ala Pro Leu Ser Gly Met Ser Trp Ser Ala Ser Ser
                85                  90                  95

TTT TGT ACA GCT CAC TGT AAT TTT ACT TCT TAT ATA GTG TTT GTT ACA       336
Phe Cys Thr Ala His Cys Asn Phe Thr Ser Tyr Ile Val Phe Val Thr
            100                 105                 110

CAT TGT TTT AAG AGC GGA TCT AAT AGT TGT CCT TTG ACA GGT CTT ATT       384
His Cys Phe Lys Ser Gly Ser Asn Ser Cys Pro Leu Thr Gly Leu Ile
        115                 120                 125
```

```
CCA AGC GGT TAT ATT CGT ATT GCT GCT ATG AAA CAT GGA AGT CGT ACG        432
Pro Ser Gly Tyr Ile Arg Ile Ala Ala Met Lys His Gly Ser Arg Thr
130                 135                 140

CCT GGT CAC TTA TTT TAT AAC TTA ACA GTT TCT GTG ACT AAA TAT CCT        480
Pro Gly His Leu Phe Tyr Asn Leu Thr Val Ser Val Thr Lys Tyr Pro
145                 150                 155                 160

AAG TTT AGA TCG CTA CAA TGT GTT AAT AAT CAT ACT TCT GTA TAT TTA        528
Lys Phe Arg Ser Leu Gln Cys Val Asn Asn His Thr Ser Val Tyr Leu
                165                 170                 175

AAT GGT GAC CTT GTT TTC ACA TCT AAC TAT ACT GAA GAT GTT GTA GCT        576
Asn Gly Asp Leu Val Phe Thr Ser Asn Tyr Thr Glu Asp Val Val Ala
                180                 185                 190

GCA GGT GTC CAT TTT AAA AGT GGT GGA CCT ATA ACT TAT AAA GTT ATG        624
Ala Gly Val His Phe Lys Ser Gly Gly Pro Ile Thr Tyr Lys Val Met
            195                 200                 205

AGA GAG GTT AAA GCC TTG GCT TAT TTT GTC AAT GGT ACT GCA CAT GAT        672
Arg Glu Val Lys Ala Leu Ala Tyr Phe Val Asn Gly Thr Ala His Asp
210                 215                 220

GTC ATT CTA TGT GAT GAC ACA CCT AGA GGT TTG TTA GCA TGC CAA TAT        720
Val Ile Leu Cys Asp Asp Thr Pro Arg Gly Leu Leu Ala Cys Gln Tyr
225                 230                 235                 240

AAT ACT GGC AAT TTT TCA GAT GGC TTC TAT CCT TTT ACT AAT ACT AGT        768
Asn Thr Gly Asn Phe Ser Asp Gly Phe Tyr Pro Phe Thr Asn Thr Ser
                245                 250                 255

ATT GTT AAG GAT AAG TTT ATT GTT TAT CGT GAA AGT AGT GTC AAT ACT        816
Ile Val Lys Asp Lys Phe Ile Val Tyr Arg Glu Ser Ser Val Asn Thr
                260                 265                 270

ACT TTG ACA TTA ACT AAT TTC ACG TTT AGT AAT GAA AGT GGT GCC CCT        864
Thr Leu Thr Leu Thr Asn Phe Thr Phe Ser Asn Glu Ser Gly Ala Pro
            275                 280                 285

CCT AAT ACA GGT GGT GTT GAC AGT TTT ATT TTA TAC CAG ACA CAA ACA        912
Pro Asn Thr Gly Gly Val Asp Ser Phe Ile Leu Tyr Gln Thr Gln Thr
290                 295                 300

GCT CAG AGT GGT TAT TAT AAT TTT AAT TTT TCA TTT CTG AGT AGT TTT        960
Ala Gln Ser Gly Tyr Tyr Asn Phe Asn Phe Ser Phe Leu Ser Ser Phe
305                 310                 315                 320

GTT TAT AGG GAA AGT AAT TAT ATG TAT GGA TCT TAC CAT CCG GCT TGT       1008
Val Tyr Arg Glu Ser Asn Tyr Met Tyr Gly Ser Tyr His Pro Ala Cys
                325                 330                 335

AGT TTT AGA CCT GAA ACC CTT AAT GGT TTG TGG TCT AAT TCC CTT TCT       1056
Ser Phe Arg Pro Glu Thr Leu Asn Gly Leu Trp Ser Asn Ser Leu Ser
                340                 345                 350

GTT TCA TTA ATA TAC GGT CCC ATT CAA GGT GGT TGT AAG CAA TCT GTA       1104
Val Ser Leu Ile Tyr Gly Pro Ile Gln Gly Gly Cys Lys Gln Ser Val
            355                 360                 365

TTT AAT GGT AAA GCA ACT TGT TGT TAT GCT TAT TCA TAC GGA GGA CCT       1152
Phe Asn Gly Lys Ala Thr Cys Cys Tyr Ala Tyr Ser Tyr Gly Gly Pro
370                 375                 380

CGT GCT TGT AAA GGT GTC TAT AGA GGT GAG CTA ACA CAG CAT TTT GAA       1200
Arg Ala Cys Lys Gly Val Tyr Arg Gly Glu Leu Thr Gln His Phe Glu
385                 390                 395                 400

TGT GGT TTG TTA GTT TAT GTT ACT AAG AGC GAT GGC TCC CGT ATA CAA       1248
Cys Gly Leu Leu Val Tyr Val Thr Lys Ser Asp Gly Ser Arg Ile Gln
                405                 410                 415

ACT GCA ACA CAA CCA CCT GTA TTA ACC CAA AAT TTT TAT AAT AAC ATC       1296
Thr Ala Thr Gln Pro Pro Val Leu Thr Gln Asn Phe Tyr Asn Asn Ile
                420                 425                 430

ACT TTA GGT AAG TGT GTT GAT TAT AAT GTT TAT GGT AGA ACT GGA CAA       1344
Thr Leu Gly Lys Cys Val Asp Tyr Asn Val Tyr Gly Arg Thr Gly Gln
            435                 440                 445
```

```
GGT TTT ATT ACT AAT GTA ACT GAT TTA GCT ACT TCC CAT AAT TAC TTA      1392
Gly Phe Ile Thr Asn Val Thr Asp Leu Ala Thr Ser His Asn Tyr Leu
    450                 455                 460

GCG GAG GGA GGA TTA GCT ATT TTA GAT ACA TCT GGT GCC ATA GAC ATC      1440
Ala Glu Gly Gly Leu Ala Ile Leu Asp Thr Ser Gly Ala Ile Asp Ile
465                 470                 475                 480

TTC GTT GTA CAA GGT GAA TAT GGC CCT AAC TAC TAT AAG GTT AAT CTA      1488
Phe Val Val Gln Gly Glu Tyr Gly Pro Asn Tyr Tyr Lys Val Asn Leu
                    485                 490                 495

TGT GAA GAT GTT AAC CAA CAG TTT GTA GTT TCT GGT GGT AAA TTA GTA      1536
Cys Glu Asp Val Asn Gln Gln Phe Val Val Ser Gly Gly Lys Leu Val
            500                 505                 510

GGT ATT CTC ACT TCA CGT AAT GAA ACT GGT TCT CAG CCT CTT GAA AAC     1584
Gly Ile Leu Thr Ser Arg Asn Glu Thr Gly Ser Gln Pro Leu Glu Asn
        515                 520                 525

CAG TTT TAC ATT AAG ATC ACT AAT GGA ACA CAT CGT TCT AGA CGT TCT      1632
Gln Phe Tyr Ile Lys Ile Thr Asn Gly Thr His Arg Ser Arg Arg Ser
    530                 535                 540

GTT AAT GAA AAT GTT ACG AAT TGC CCT TAT GTT AGT TAT GGC AAG TTT      1680
Val Asn Glu Asn Val Thr Asn Cys Pro Tyr Val Ser Tyr Gly Lys Phe
545                 550                 555                 560

TGT ATA AAA CCT GAT GGT TCA GTT TCT CCT ATA GTA CCA AAA GAA CTT      1728
Cys Ile Lys Pro Asp Gly Ser Val Ser Pro Ile Val Pro Lys Glu Leu
                565                 570                 575

GAA CAG TTT GTG GCA CCT TTA CTT AAT GTT ACT GAA AAT GTG CTC ATA      1776
Glu Gln Phe Val Ala Pro Leu Leu Asn Val Thr Glu Asn Val Leu Ile
            580                 585                 590

CCT AAC AGT TTT AAC TTA ACT GTT ACA GAT GAG TAC ATA CAA ACG CGT      1824
Pro Asn Ser Phe Asn Leu Thr Val Thr Asp Glu Tyr Ile Gln Thr Arg
        595                 600                 605

ATG GAT AAG GTC CAA ATT AGG A                                        1846
Met Asp Lys Val Gln Ile Arg
    610                 615

(2) INFORMATION FOR SEQ ID NO:17:

(i) SEQUENCE CHARACTERISTICS:
        (A) LENGTH: 615 amino acids
        (B) TYPE: amino acid
        (D) TOPOLOGY: linear (ii) MOLECULE TYPE: protein (xi) SEQUENCE DESCRIPTION: SEQ ID NO:17:

Met Leu Val Lys Ser Leu Phe Leu Val Thr Ile Leu Phe Ala Leu Cys
1               5                   10                  15

Ser Ala Asn Leu Tyr Asp Asn Glu Ser Phe Val Tyr Tyr Gln Ser
            20                  25                  30

Ala Phe Arg Pro Gly His Gly Trp His Leu His Gly Ala Tyr Ala
        35                  40                  45

Val Val Asn Val Ser Ser Glu Asn Asn Ala Gly Thr Ala Pro Ser
    50                  55                  60

Cys Thr Ala Gly Ala Ile Gly Tyr Ser Lys Asn Phe Ser Ala Ser
65                  70                  75                  80

Val Ala Met Thr Ala Pro Leu Ser Gly Met Ser Trp Ser Ala Ser
            85                  90                  95

Phe Cys Thr Ala His Cys Asn Phe Thr Ser Tyr Ile Val Phe Val Thr
            100                 105                 110

His Cys Phe Lys Ser Gly Ser Asn Ser Cys Pro Leu Thr Gly Leu Ile
        115                 120                 125
```

-continued

```
Pro Ser Gly Tyr Ile Arg Ile Ala Ala Met Lys His Gly Ser Arg Thr
    130                 135                 140
Pro Gly His Leu Phe Tyr Asn Leu Thr Val Ser Val Thr Lys Tyr Pro
145                 150                 155                 160
Lys Phe Arg Ser Leu Gln Cys Val Asn Asn His Thr Ser Val Tyr Leu
                165                 170                 175
Asn Gly Asp Leu Val Phe Thr Ser Asn Tyr Thr Glu Asp Val Val Ala
            180                 185                 190
Ala Gly Val His Phe Lys Ser Gly Gly Pro Ile Thr Tyr Lys Val Met
        195                 200                 205
Arg Glu Val Lys Ala Leu Ala Tyr Phe Val Asn Gly Thr Ala His Asp
    210                 215                 220
Val Ile Leu Cys Asp Asp Thr Pro Arg Gly Leu Leu Ala Cys Gln Tyr
225                 230                 235                 240
Asn Thr Gly Asn Phe Ser Asp Gly Phe Tyr Pro Phe Thr Asn Thr Ser
                245                 250                 255
Ile Val Lys Asp Lys Phe Ile Val Tyr Arg Glu Ser Ser Val Asn Thr
            260                 265                 270
Thr Leu Thr Leu Thr Asn Phe Thr Phe Ser Asn Glu Ser Gly Ala Pro
        275                 280                 285
Pro Asn Thr Gly Gly Val Asp Ser Phe Ile Leu Tyr Gln Thr Gln Thr
    290                 295                 300
Ala Gln Ser Gly Tyr Tyr Asn Phe Asn Phe Ser Phe Leu Ser Ser Phe
305                 310                 315                 320
Val Tyr Arg Glu Ser Asn Tyr Met Tyr Gly Ser Tyr His Pro Ala Cys
                325                 330                 335
Ser Phe Arg Pro Glu Thr Leu Asn Gly Leu Trp Ser Asn Ser Leu Ser
            340                 345                 350
Val Ser Leu Ile Tyr Gly Pro Ile Gln Gly Gly Cys Lys Gln Ser Val
        355                 360                 365
Phe Asn Gly Lys Ala Thr Cys Cys Tyr Ala Tyr Ser Tyr Gly Gly Pro
370                 375                 380
Arg Ala Cys Lys Gly Val Tyr Arg Gly Glu Leu Thr Gln His Phe Glu
385                 390                 395                 400
Cys Gly Leu Leu Val Tyr Val Thr Lys Ser Asp Gly Ser Arg Ile Gln
                405                 410                 415
Thr Ala Thr Gln Pro Pro Val Leu Thr Gln Asn Phe Tyr Asn Asn Ile
            420                 425                 430
Thr Leu Gly Lys Cys Val Asp Tyr Asn Val Tyr Gly Arg Thr Gly Gln
        435                 440                 445
Gly Phe Ile Thr Asn Val Thr Asp Leu Ala Thr Ser His Asn Tyr Leu
    450                 455                 460
Ala Glu Gly Gly Leu Ala Ile Leu Asp Thr Ser Gly Ala Ile Asp Ile
465                 470                 475                 480
Phe Val Val Gln Gly Glu Tyr Gly Pro Asn Tyr Tyr Lys Val Asn Leu
                485                 490                 495
Cys Glu Asp Val Asn Gln Phe Val Val Ser Gly Gly Lys Leu Val
            500                 505                 510
Gly Ile Leu Thr Ser Arg Asn Glu Thr Gly Ser Gln Pro Leu Glu Asn
        515                 520                 525
Gln Phe Tyr Ile Lys Ile Thr Asn Gly Thr His Arg Ser Arg Arg Ser
    530                 535                 540
```

Val Asn Glu Asn Val Thr Asn Cys Pro Tyr Val Ser Tyr Gly Lys Phe
545                 550                 555                 560

Cys Ile Lys Pro Asp Gly Ser Val Ser Pro Ile Val Pro Lys Glu Leu
            565                 570                 575

Glu Gln Phe Val Ala Pro Leu Leu Asn Val Thr Glu Asn Val Leu Ile
            580                 585                 590

Pro Asn Ser Phe Asn Leu Thr Val Thr Asp Glu Tyr Ile Gln Thr Arg
        595                 600                 605

Met Asp Lys Val Gln Ile Arg
    610             615

(2) INFORMATION FOR SEQ ID NO:18:

(i) SEQUENCE CHARACTERISTICS:
        (A) LENGTH: 2116 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:18:

```
TATAATTATC TAGCAGACGC AGGTATGGCT ATTTTAGATA CATCTGGTTC CATAGACATC      60
TTTGTTGCAC AAGGTGAATA TGGCCTTACT TATTATAAGG CTAACCCTTG CGAAGACGTC     120
AACCAGCAGT TTGTAGTTTC TGGTGGTAAA TTAGTAGGTA TTCTTACTTC ACGTAATGAG     180
ACTGGTTCTC AGCTTCTTGA GAACCAGTTT TACATTAAAA TCACTAATGG AACACGTCGT     240
TCTAGACGTT CTATTACTGC AAATGTHACA AATYGCCCTT ATGTTAGCTA TGGCAAGTTT     300
TGTCTAAAAC CTGATGGYTC AGYTTCTGYT ATAGCACCAC NNNNNNNNNN NNNNNNNNNN     360
NNNNNNNNNN NNNNNNNNNN NNNNNNNNNN NNNNNNNNNN NNNNNNNNNN NNNNNNNNNN     420
NNNNNNNNNN NNNNNNNNNN NNNNNNNNNN NNNNNNNNNN NNNNNNNNNN NNNNNNNNNT     480
GTTTGTGGCA ATTCTCTGGA TTGTAGAAAG TTGYTTCAAC AATATGGGCC TGTTTGBGAC     540
AACATATTGT CTGTGGTAAA TAGTGTTGGT CAAAAAGAAG ATATGGAACT TCUAAATCTC     600
TATTCTTCTA CTAAACCATC TGGCTTTAAT ACACCAGTTT TTAGTAATCT YAGCACTGGC     660
GATTTYAATA TTTCTCTTYT GGTTGACACC TCCAGTAGTA CTACTGGGCG CTCTTTTATT     720
GAAGATCTTT TATTTACAAG TGTTGAATCT GTTGGATTAC AACAGATGA AGCTTATAAA      780
AAGTGCACTG CAGGACCTTT AGGCTTCCTT AAGGACCTBG CGTGTGCTCG TGAATATAAT     840
GGCTTGCTTG YNNNNNNCCC TATTATAACA GCAGAAATGC AAACCTTGTA TACTAGTTCT     900
TTAGTAGCTT CTATGGCTTT TGGTGGGATT ACTGCAGCTG GTGCTATACC TTTTGCCACA     960
CAACTGCAGG CTAGAATTAA TCACTTGGGT ATTACCCAGT CACTTTTGCA GAAAAATCAA    1020
GAAAAAATTG CTGCCTCCTT TAATAAGGCC ATTGGCCATA TGCAGGAAGG TTTTAGAAGT    1080
ACATCTCTAG CATTACAACA AGTYCAMGAT GTTGTTAATA AGCAGAGTGC TATTCTTACT    1140
GAGACTATGG CATCACTTAA TAAAAATTTK GGTGCTATTT CTTCTGTGAT TCAAGATATC    1200
TACCAGCAAC TTGACGCCAT ACAAGCAAAT GCTCAAGTGG ATCGTCTTAT AACTGGTAGA    1260
TTGTCATCAC TTTCTGTTTT AGCATCTGCT AAGCAGGCGG AGTATATTAG AGTGTCACAA    1320
CAGCGTGAGT TAGCTACTCA GAAAATTAAT GAGTGTGTTA AATCACAGTC TATTAGGTAC    1380
TCCTTTTGTG GTAATGGACG ACACGTTCTA ACTATACCGC AAAATGCACC TAATGGTATA    1440
```

```
GTGTTTATAC ACTTTACTTA TACTCCAGAG AGTTTTGKTA ATGTTACTGC AATAGTGGGT    1500

TTTTGTAARG CCGCTAATGC TAGTCAGTAT GCAATAGTGC CTGCTAATGG CAGAGGTATT    1560

TCTATACAAG TTAATGGTAG TCACTACATC ACTGCACGAG ATATGTATAT GCCAAGAGAT    1620

ATTACTGCAG GAGATATAGT TACGCTTACT TCTTGTCAAG CAAATTATGT AAGTGTAMMT    1680

AAGACCGTCA TTACYACATT HGTAGACAAT GATGATTTTG ATTTTGATGA CGAATTGTCA    1740

AAATGGTGGA ATGATACTAA GCATGAGCTA CCAGACTTTG ACGAATTCAA TTACACAGTA    1800

CCTATACTTG ACATTGGTAG TGAAATTGAT CGTATTCAAG GCGTTATACA GGGCCTTAAT    1860

GACTCTCTAA TAGACCTTGA AACACTATCA ATACTCAAAA CTTATATTAA GTGGCCTTGG    1920

TATGTGTGGT TAGCCATAGC TTTTGSCACT ATTATCTTCA TCCTAATATT AGGGTGGGTG    1980

TTTTTCATGA CTGGTTGTTG TGGTTGTTGT TGTGGATGCT TTGGCATTAT TCCTCTAATG    2040

AGCAAGTGTG GTAAGAAATC TTCTTATTAC ACGACTTTGG ATAATGATGT GGTAACTGAA    2100

CAAWACAGAC CYAAAA                                                   2116
```

(2) INFORMATION FOR SEQ ID NO:19:

(i) SEQUENCE CHARACTERISTICS:
        (A) LENGTH: 705 amino acids
        (B) TYPE: amino acid
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:19:

```
Tyr Asn Tyr Leu Ala Asp Ala Gly Met Ala Ile Leu Asp Thr Ser Gly
 1               5                  10                  15

Ser Ile Asp Ile Phe Val Ala Gln Gly Glu Tyr Gly Leu Thr Tyr Tyr
            20                  25                  30

Lys Ala Asn Pro Cys Glu Asp Val Asn Gln Gln Phe Val Ser Gly
        35                  40                  45

Gly Lys Leu Val Gly Ile Leu Thr Ser Arg Asn Glu Thr Gly Ser Gln
    50                  55                  60

Leu Leu Glu Asn Gln Phe Tyr Ile Lys Ile Thr Asn Gly Thr Arg Arg
65                  70                  75                  80

Ser Arg Arg Ser Ile Thr Ala Asn Val Thr Asn Xaa Pro Tyr Val Ser
                85                  90                  95

Tyr Gly Lys Phe Cys Leu Lys Pro Asp Gly Ser Xaa Ser Xaa Ile Ala
            100                 105                 110

Pro Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa
145                 150                 155                 160

Val Cys Gly Asn Ser Leu Asp Cys Arg Lys Leu Xaa Gln Gln Tyr Gly
                165                 170                 175

Pro Val Xaa Asp Asn Ile Leu Ser Val Val Asn Ser Val Gly Gln Lys
            180                 185                 190

Glu Asp Met Glu Leu Leu Asn Leu Tyr Ser Ser Thr Lys Pro Ser Gly
        195                 200                 205
```

-continued

```
Phe Asn Thr Pro Val Phe Ser Asn Leu Ser Thr Gly Asp Phe Asn Ile
    210                 215                 220
Ser Leu Leu Val Asp Thr Ser Ser Thr Thr Gly Arg Ser Phe Ile
225                 230                 235                 240
Glu Asp Leu Leu Phe Thr Ser Val Glu Ser Val Gly Leu Pro Thr Asp
                    245                 250                 255
Glu Ala Tyr Lys Lys Cys Thr Ala Gly Pro Leu Gly Phe Leu Lys Asp
                260                 265                 270
Leu Ala Cys Ala Arg Glu Tyr Asn Gly Leu Leu Xaa Xaa Xaa Pro Ile
            275                 280                 285
Ile Thr Ala Glu Met Gln Thr Leu Tyr Thr Ser Ser Leu Val Ala  Ser
        290                 295                 300
Met Ala Phe Gly Gly Ile Thr Ala Gly Ala Ile Pro Phe Ala Thr
305                 310                 315                 320
Gln Leu Gln Ala Arg Ile Asn His Leu Gly Ile Thr Gln Ser Leu Leu
                    325                 330                 335
Gln Lys Asn Gln Glu Lys Ile Ala Ala Ser Phe Asn Lys Ala Ile Gly
                340                 345                 350
His Met Gln Glu Gly Phe Arg Ser Thr Ser Leu Ala Leu Gln Gln Val
            355                 360                 365
Xaa Asp Val Val Asn Lys Gln Ser Ala Ile Leu Thr Glu Thr Met Ala
370                 375                 380
Ser Leu Asn Lys Asn Xaa Gly Ala Ile Ser Ser Val Ile Gln Asp Ile
385                 390                 395                 400
Tyr Gln Gln Leu Asp Ala Ile Gln Ala Asn Ala Gln Val Asp Arg Leu
                    405                 410                 415
Ile Thr Gly Arg Leu Ser Ser Leu Ser Val Leu Ala Ser Ala Lys Gln
                420                 425                 430
Ala Glu Tyr Ile Arg Val Ser Gln Gln Arg Glu Leu Ala Thr Gln Lys
            435                 440                 445
Ile Asn Glu Cys Val Lys Ser Gln Ser Ile Arg Tyr Ser Phe Cys Gly
        450                 455                 460
Asn Gly Arg His Val Leu Thr Ile Pro Gln Asn Ala Pro Asn Gly Ile
465                 470                 475                 480
Val Phe Ile His Phe Thr Tyr Thr Pro Glu Ser Phe Xaa Asn Val Thr
                485                 490                 495
Ala Ile Val Gly Phe Cys Lys Ala Ala Asn Ala Ser Gln Tyr Ala Ile
                500                 505                 510
Val Pro Ala Asn Gly Arg Gly Ile Ser Ile Gln Val Asn Gly Ser His
            515                 520                 525
Tyr Ile Thr Ala Arg Asp Met Tyr Met Pro Arg Asp Ile Thr Ala Gly
        530                 535                 540
Asp Ile Val Thr Leu Thr Ser Cys Gln Ala Asn Tyr Val Ser Val Xaa
545                 550                 555                 560
Lys Thr Val Ile Thr Thr Xaa Val Asp Asn Asp Phe Asp Phe Asp
                565                 570                 575
Asp Glu Leu Ser Lys Trp Trp Asn Asp Thr Lys His Glu Leu Pro Asp
                580                 585                 590
Phe Asp Glu Phe Asn Tyr Thr Val Pro Ile Leu Asp Ile Gly Ser Glu
            595                 600                 605
Ile Asp Arg Ile Gln Gly Val Ile Gln Gly Leu Asn Asp Ser Leu Ile
        610                 615                 620
Asp Leu Glu Thr Leu Ser Ile Leu Lys Thr Tyr Ile Lys Trp Pro Trp
625                 630                 635                 640
```

```
       Tyr Val Trp Leu Ala Ile Ala Phe Xaa Thr Ile Ile Phe Ile Leu Ile
                       645                 650                 655

Leu Gly Trp Val Phe Phe Met Thr Gly Cys Cys Gly Cys Cys Cys Gly
                       660                 665                 670

Cys Phe Gly Ile Ile Pro Leu Met Ser Lys Cys Gly Lys Lys Ser Ser
                       675                 680                 685

Tyr Tyr Thr Thr Leu Asp Asn Asp Val Val Thr Glu Gln Xaa Arg Pro
                       690                 695                 700

Lys
       705
```

(2) INFORMATION FOR SEQ ID NO:20:

(i) SEQUENCE CHARACTERISTICS:
        (A) LENGTH: 36 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:20:

```
GAATTCGAGC TCGCCCGGGG ATCCTCTAGA GTCGAC                              36
```

(2) INFORMATION FOR SEQ ID NO:21:

(i) SEQUENCE CHARACTERISTICS:
        (A) LENGTH: 57 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION: 13..57

(xi) SEQUENCE DESCRIPTION: SEQ ID NO:21:

```
CACAGCTCAA CA ATG AAG TGG GCA ACG TGG ATC GAT CCC GTC GTT TTA       48
              Met Lys Trp Ala Thr Trp Ile Asp Pro Val Val Leu
                1               5                  10

CAA CGT CGT                                                         57
Gln Arg Arg
        15
```

(2) INFORMATION FOR SEQ ID NO:22:

(i) SEQUENCE CHARACTERISTICS:
        (A) LENGTH: 15 amino acids
        (B) TYPE: amino acid
        (D) TOPOLOGY: linear (ii) MOLECULE TYPE: protein (xi) SEQUENCE DESCRIPTION: SEQ ID NO:22:

```
Met Lys Trp Ala Thr Trp Ile Asp Pro Val Val Leu Gln Arg Arg
  1               5                  10                  15
```

(2) INFORMATION FOR SEQ ID NO:23:

(i) SEQUENCE CHARACTERISTICS:
        (A) LENGTH: 57 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:23:

ACTCGGGCAG CGTTGGGTCC TGGGACTCTA GAGGATCGAT CCCCTATGGC GATCATC      57

(2) INFORMATION FOR SEQ ID NO:24:

(i) SEQUENCE CHARACTERISTICS:
        (A) LENGTH: 99 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:24:

GCGCCCACGT GGCCTGGTAC AATTCGAGCT CGCCCGGGGA TCCTCTAGAG TCGACTCTAG   60

AGGATCGATC CTCTAGAGTC GGCGGGACGA GCCCGCGAT                         99

(2) INFORMATION FOR SEQ ID NO:25:

(i) SEQUENCE CHARACTERISTICS:
        (A) LENGTH: 57 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:25:

TCCACAGGAC CTGCAGCGAC CCGCTTAACA GCGTCAACAG CGTGCCGCAG ATCGGGG      57

(2) INFORMATION FOR SEQ ID NO:26:

(i) SEQUENCE CHARACTERISTICS:
        (A) LENGTH: 35 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:26:

GTTGATCCCG GGAGATGGGG GAGGCTAACT GAAAC                              35

(2) INFORMATION FOR SEQ ID NO:27:

(i) SEQUENCE CHARACTERISTICS:
            (A) LENGTH: 103 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:27:

GCTCATGGTG GCCCCCGGGC GGTTCAACGA GGGCCAGTAC CGGCGCCTGG TGTCCGTCGA      60

CCTGCAGGTC GACTCTAGAG GATCCCCGGG CGAGCTCGAA TTC      103

(2) INFORMATION FOR SEQ ID NO:28:

(i) SEQUENCE CHARACTERISTICS:
            (A) LENGTH: 66 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:28:

GAATTCGAGC TCGCCCGGGG ATCCTCTAGA GTCGACGTCT GGGGCGCGGG GGTGGTGCTC      60

TTCGAG      66

(2) INFORMATION FOR SEQ ID NO:29:

(i) SEQUENCE CHARACTERISTICS:
            (A) LENGTH: 66 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (ix) FEATURE:
            (A) NAME/KEY: CDS
            (B) LOCATION: 16..66

(xi) SEQUENCE DESCRIPTION: SEQ ID NO:29:

CTCCACAGCT CAACA ATG AAG TGG GCA ACG TGG ATC GAT CCC GTC GTT TTA      51
                Met Lys Trp Ala Thr Trp Ile Asp Pro Val Val Leu
                  1               5                  10

CAA CGT CGT GAC TGG      66
Gln Arg Arg Asp Trp
        15

(2) INFORMATION FOR SEQ ID NO:30:

(i) SEQUENCE CHARACTERISTICS:
            (A) LENGTH: 17 amino acids
            (B) TYPE: amino acid
            (D) TOPOLOGY: linear (ii) MOLECULE TYPE: protein (xi) SEQUENCE DESCRIPTION: SEQ ID NO:30:

```
Met Lys Trp Ala Thr Trp Ile Asp Pro Val Val Leu Gln Arg Arg Asp
 1               5                  10                  15
Trp
```

(2) INFORMATION FOR SEQ ID NO:31:

(i) SEQUENCE CHARACTERISTICS:
        (A) LENGTH: 132 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION: 1..93

(xi) SEQUENCE DESCRIPTION: SEQ ID NO:31:

```
GAC GAC TCC TGG AGC CCG TCA GTA TCG GCG GAA ATC CAG CTG AGC GCC      48
Asp Asp Ser Trp Ser Pro Ser Val Ser Ala Glu Ile Gln Leu Ser Ala
 1               5                  10                  15

GGT CGC TAC CAT TAC CAG TTG GTC TGG TGT CAA AAA GAT CTA GAA          93
Gly Arg Tyr His Tyr Gln Leu Val Trp Cys Gln Lys Asp Leu Glu
             20                  25                  30

TAAGCTAGAG GATCGATCCC CTATGGCGAT CATCAGGGC                          132
```

(2) INFORMATION FOR SEQ ID NO:32:

(i) SEQUENCE CHARACTERISTICS:
        (A) LENGTH: 31 amino acids
        (B) TYPE: amino acid
        (D) TOPOLOGY: linear (ii) MOLECULE TYPE: protein (xi) SEQUENCE DESCRIPTION: SEQ ID NO:32:

```
Asp Asp Ser Trp Ser Pro Ser Val Ser Ala Glu Ile Gln Leu Ser Ala
 1               5                  10                  15

Gly Arg Tyr His Tyr Gln Leu Val Trp Cys Gln Lys Asp Leu Glu
             20                  25                  30
```

(2) INFORMATION FOR SEQ ID NO:33:

(i) SEQUENCE CHARACTERISTICS:
        (A) LENGTH: 66 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:33:

```
AACGAGGGCC AGTACCGGCG CCTGGTGTCC GTCGACTCTA GAGGATCCCC GGGCGAGCTC      60

GAATTC                                                                 66
```

(2) INFORMATION FOR SEQ ID NO:34:

(i) SEQUENCE CHARACTERISTICS:
        (A) LENGTH: 65 base pairs (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:34:

CAGGTCGAAG CTTGGGCGCT GCCTATGTAG TGAAATCTAT ACTGGGATTT ATCATAACTA    60

GTTTA    65

(2) INFORMATION FOR SEQ ID NO:35:

(i) SEQUENCE CHARACTERISTICS:
            (A) LENGTH: 65 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:35:

AATAATCTAT CACTTTGTCA TGGAGATGCC CAAGCTTCGA CGACTCCCTT GGCCATGATG    60

AATGG    65

(2) INFORMATION FOR SEQ ID NO:36:

(i) SEQUENCE CHARACTERISTICS:
            (A) LENGTH: 65 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:36:

TATACCAGCT ACGGCGCTAG CATTCATGGT ATCCCGTGAT TGCTCGATGC TTTCCTTCTG    60

AATTC    65

(2) INFORMATION FOR SEQ ID NO:37:

(i) SEQUENCE CHARACTERISTICS:
            (A) LENGTH: 65 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:37:

AAGCTTGGCC TCGTCGTTAA TTAACCCAAT TCGAGCTCGC CCAGCTTGGG CTGCAGGTCG    60

GGAAC    65

(2) INFORMATION FOR SEQ ID NO:38:

(i) SEQUENCE CHARACTERISTICS:
        (A) LENGTH: 65 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:38:

```
TGTTTCAGTT AGCCTCCCCC ATCTCCCGAC TCTAGAGGAT CTCGACATAG CGAATACATT     60

TATGG                                                                 65
```

(2) INFORMATION FOR SEQ ID NO:39:

(i) SEQUENCE CHARACTERISTICS:
        (A) LENGTH: 130 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:39:

```
AACGTATATA TTTTTCACGA CGTAGACCAC TATTGCCATG GACTCTAGAG GATCGGGTAC     60

CGAGCTCGAA TTGGGAAGCT TGTCGACTTA ATTAAGCGGC CGCGTTTAAA CGGCCCTCGA    120

GGCCAAGCTT                                                          130
```

(2) INFORMATION FOR SEQ ID NO:40:

(i) SEQUENCE CHARACTERISTICS:
        (A) LENGTH: 60 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:40:

```
GTCGACGTCT GGGGCGCGGG GGTGGTGCTC TTCGAGACGC TGCCTACCCC AAGACGATCG     60
```

(2) INFORMATION FOR SEQ ID NO:41:

(i) SEQUENCE CHARACTERISTICS:
        (A) LENGTH: 60 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:41:

```
AGCTCAACAA TGAAGTGGGC AACGTGGATC GATCCCGTCG TTTTACAACG TCGTGACTGG     60
```

(2) INFORMATION FOR SEQ ID NO:42:

(i) SEQUENCE CHARACTERISTICS:
        (A) LENGTH: 120 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:42:

GAGCCCGTCA GTATCGGCGG AAATCCAGCT GAGCGCCGGT CGCTACCATT ACCAGTTGGT    60

GTTGGTCTGG TGTCAAAAAG ATCCGGACCG CGCCGTTAGC CAAGTTGCGT TAGAGAATGA   120

(2) INFORMATION FOR SEQ ID NO:43:

(i) SEQUENCE CHARACTERISTICS:
        (A) LENGTH: 60 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:43:

ACACAGTCAC ACTCATGGGG GCCGAAGGCA GAATTCGTAA TCATGGTCAT AGCTGTTTCC    60

(2) INFORMATION FOR SEQ ID NO:44:

(i) SEQUENCE CHARACTERISTICS:
        (A) LENGTH: 60 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:44:

AAACCTGTCG TGCCAGCGAG CTCGGGATCC TCTAGAGGAT CCCCGGGCCC CGCCCCCTGC    60

(2) INFORMATION FOR SEQ ID NO:45:

(i) SEQUENCE CHARACTERISTICS:
        (A) LENGTH: 60 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:45:

TCGTCCACAC GGAGCGCGGC TGCCGACACG GATCCCGGTT GGCGCCCTCC AGGTGCAGGA    60

```
(2) INFORMATION FOR SEQ ID NO:46:

(i) SEQUENCE CHARACTERISTICS:
        (A) LENGTH: 60 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:46:

AACCCCCCCC CCCCCCCCCC CCCCCCCCTG CAGGCATCGT GGTGTCACGC TCGTCGTTTG      60

(2) INFORMATION FOR SEQ ID NO:47:

(i) SEQUENCE CHARACTERISTICS:
        (A) LENGTH: 60 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:47:

TGTCATGCCA TCCGTAAGAT GCTTTTCTGT GACTGGTGAG TCGGATCCTC TAGAGTCGAC      60
```

RECOMBINANT HERPESVIRUS OF TURKEYS AND USES THEREOF

This application is a continuation-in-part of U.S. Ser. No. 898,087, filed Jun. 12, 1992 now abandoned; U.S. Ser. No. 225,032, filed Jul. 27, 1988, now U.S. Pat. No. 5,223,424, which is a continuation-in-part of U.S. Ser. No. 078,519, filed Jul. 27, 1987, now abandoned, U.S. Ser. No. 933,107, filed Nov. 20, 1986, now abandoned, U.S. Ser. No. 902,887, filed Sep. 2, 1986, now abandoned, U.S. Ser. No. 823,102, filed Jan. 27, 1986, now U.S. Pat. No. 5,068,192, issued Nov. 26, 1991, and U.S. Ser. No. 773,430, filed Sep. 6, 1985, now U.S. Pat. No. 4,877,737, issued Oct. 31, 1989; U.S. Ser. No. 649,380, filed Jan. 31, 1991, now abandoned, which is a continuation of U.S. Ser. No. 078,519, filed Jul. 27, 1987, now abandoned, which is a continuation-in-part of U.S. Ser. No. 933,107, filed Nov. 20, 1986, now abandoned, U.S. Ser. No. 902,877, filed Sep. 2, 1986, now abandoned, U.S. Ser. No. 887,140, filed Jul. 17, 1986, now abandoned, U.S. Ser. No. 823,102, filed Jan. 27, 1986, now U.S. Pat. No. 5,068, 192, issued Nov. 26, 1991, and U.S. Ser. No. 773,403, filed Sep. 6, 1985, now U.S. Pat. No. 4,716,287, issued Oct. 31, 1989; and U.S. Ser. No. 914,057, filed Jul. 13, 1992, now abandoned, which is a continuation-in-part of U.S. Ser. No. 696,262, filed Apr. 30, 1991, now abandoned, which is a continuation of U.S. Ser. No. 933,107, filed Nov. 20, 1986, now abandoned, which is a continuation-in-part of U.S. Ser. No. 773,430, filed Sep. 6, 1985, now U.S. Pat. No. 4,877, 737, issued Oct. 31, 1989, and U.S. Ser. No. 823,102, filed Jan. 27, 1986, now U.S. Pat. No. 5,068,192.

BACKGROUND OF THE INVENTION

The ability to isolate DNA and clone this isolated DNA into bacterial plasmids has greatly expanded the approaches available to make viral vaccines. The methods used to make the present invention involve modifying cloned DNA sequences from various pathogens of animals, by insertions, deletions, single or multiple base changes, and subsequent insertions of these modified sequences into the genome of the virus. One utility of the addition of foreign sequences is achieved when the foreign sequence encodes a foreign protein that is expressed during viral infection of the animal. The resulting live virus may then be used in a vaccine to elicit an immune response in a host animal and provide protection to the animal against disease. A virus with these characteristics is referred to as a viral vector, because it becomes a living vector that will carry and express the foreign protein in the host animal. In effect it becomes an elaborate delivery system for the foreign protein(s).

More specifically, the present invention relates to the use of herpesvirus of turkeys (HVT) as a viral vector for vaccination of birds against disease. The group of herpesviruses comprise various pathogenic agents that infect and cause disease in a number of target species: swine, cattle, chickens, horses, dogs, cats, etc. Each herpesvirus is specific for its host species, but they are all related in the structure of their genomes, their mode of replication, and to some extent in the pathology they cause in the host animal and in the mechanism of the host immune response to the virus infection.

The application of recombinant DNA techniques to animal viruses has a relatively recent history from about 1990. The first viruses to be engineered have been those with the smallest genomes. In the case of the papovaviruses, because these viruses are so small and cannot accommodate much extra DNA, their entire use in genetic engineering has been as defective replicons. Foreign gene expression from these viruses requires a wild-type helper virus and is limited to cell culture systems. For adenoviruses, there is a small amount of nonessential DNA that can be replaced by foreign sequences. The only foreign DNA that seems to have been expressed in adenoviruses are the T-antigen genes from papovaviruses (Mansour, et al., *Proc. Natl. Acad. Sci. US,* 1985; Thummel, et al., *Cell,* 1983; Scolnick, et al., *Cell,* 1981; Thummel, et al., *Cell,* 1981), and the herpes simplex virus (HSV) thymidine kinase gene (Haj-Ahmed and Graham, *J. of Virology,* 1986). These publications do not identify the nonessential regions in HVT wherein foreign DNA may be inserted, nor do they teach how to achieve the expression of the foreign genes in HVT, e.g., which promoter sequence and termination sequence to use.

Another group of viruses that have been engineered are the poxviruses. One member of this group, vaccinia, has been the subject of much research on foreign gene expression. Poxviruses are large DNA-containing viruses that replicate in the cytoplasm of the infected cell. They have a structure that is unique in that they do not contain any capsid that is based upon icosahedral symmetry or helical symmetry. The poxviruses are most likely to have evolved from bacterial-like microorganisms through the loss of function and degeneration. In part due to this uniqueness, the advances made in the genetic engineering of poxviruses cannot be directly extrapolated to other viral systems, including herpesviruses and HVT. Vaccinia recombinant virus constructs have been made in a number of laboratories that express the following inserted foreign genes: HSV thymidine kinase gene (Mackett, et al., *Proc. Natl. Acad. Sci. USA,* 1982; Panicali and Paoletti, *Proc. Natl. Acad. Sci. USA,* 1982, hepatitis B surface antigen (Paoletti, et al., *Proc. Natl. Acad. Sci. USA,* 1984; Smith et al., *Nature,* 1983), HSV glycoprotein D gene, influenzae hemagglutinin gene (Panicali, et al., *Proc. Natl. Acad. Sci. USA,* 1983; Smith, et al., *Proc. Natl. Acad. Sci. USA,* 1983), malaria antigen gene (Smith, et al., *Science,* 1984, and vesicular stomatitis glycoprotein G gent (Mackett, et al., *Science,* 1986). The general overall features of vaccinia recombinant DNA work are similar to the techniques used for all the viruses, especially as they relate to the techniques in reference (Maniatis, et al., *Molecular Cloning,* 1982). However in detail, the vaccinia techniques are not applicable to herpesviruses and HVT. The utility of vaccinia as a vaccine vector is in question because of its close relationship to human smallpox and its known pathogenicity to humans. Thus, the use of the host-specific herpesvirus HVT is a better solution to vaccination of poultry.

Among the primate herpesviruses, only HSV of humans and, to a limited extent, herpes saimiri of monkeys have been engineered to contain foreign DNA sequences. The first use of recombinant DNA to manipulate HSV involved cloning a piece of DNA from the L-S junction region into the unique long region of HSV DNA, specifically into the thymidine kinase gene (Moccarski, et al., *Cell,* 1980). This insert was not a foreign piece of DNA, rather it was a naturally occurring piece of herpesvirus DNA that was duplicated at another place in the genome. This piece of DNA was not engineered to specifically express a protein, and thus the work does not involve expression of protein in herpesviruses. The next manipulation of HSV involved the creation of deletions in the virus genome by a combination of recombinant DNA techniques and thymidine kinase selection. Using this approach, the HSV alpha-22 gene has been deleted (Post, et al., *Cell,* 1981), and a 15,000 basepair sequence of DNA has been deleted from the internal repeat of HSV (Poffenberger, et al., *Proc. Natl. Acad. Sci. USA,* 1981).

The insertion of genes that encode protein into herpesviruses have involved seven cases: the insertion of HSV glycoprotein C back into a naturally occurring deletion mutant of this gene in HSV (Gibson and Spear, *J. of Virology,* 1983); the insertion of glycoprotein D of HSV type 2 into HSV type 1 (Lee, et al., *Proc. Natl. Acad. Sci. USA,* 1982), again with no manipulation of promoter sequences since the gene is not 'foreign'; the insertion of hepatitis B surface antigen into HSV under the control of the HSV ICP4 promoter (Shih, et al., *Proc. Natl. Acad. Sci. USA,* 1984); and the insertion of bovine growth hormone into herpes saimiri virus with an SV40 promoter (the promoter did not work this system and an endogenous upstream served to transcribe the gene) (Desrosiers, et al., 1984). Two additional cases of foreign genes (chicken ovalbumin gene and Epstein-Barr virus nuclear antigen) have been inserted into HSV (Arsenakis and Roizman, 1984), and glycoprotein X of pseudorabies virus has been inserted into HSV (Post, et al., 1985).

These limited cases of deletion and insertion of genes into herpesviruses demonstrate that it is possible to genetically engineer herpesvirus genomes by recombinant DNA techniques. The methods that have been used to insert genes involve homologous recombination between the viral DNA cloned in plasmids and purified viral DNA transfected into the same animal cell. However, the extent to which one can generalize the location of the deletion and the sites for insertion of foreign genes is not known from these previous studies.

One object of the present invention is a vaccine for Marek's disease. Marek's disease virus (MDV) is the causative agent of Marek's disease which encompasses fowl paralysis, a common lymphoproliferative disease of chickens. The disease occurs most commonly in young chickens between 2 and 5 months of age. The prominent clinical signs are progressive paralysis of one or more of the extremities, incoordination due to paralysis of legs, drooping of the limb due to wing involvement, and a lowered head position due to involvement of the neck muscles. In acute cases, severe depression may result. In the case of highly oncogenic strains, there is characteristic bursal and thymic atrophy. In addition, there are lymphoid tumors affecting the gonads, lungs, liver, spleen, kidney and thymus (Mohanty and Dutta, 1981).

Most chickens are vaccinated against MDV at one day of age to protect the bird against MDV for life. Prior to the present invention, the principal vaccination method for MDV involved using naturally occurring strains of turkey herpesvirus (HVT). It would be advantageous to incorporate other antigens into this vaccination at one day of age, but efforts to combine conventional vaccines have not proven satisfactory to date due to competition and immunosuppression between pathogens. The multivalent HVT-based vaccines engineered in this invention represent a novel way to simultaneously vaccinate against a number of different pathogens. For the first time, a recombinant HVT with a foreign gene inserted into a non-essential region of the HVT genome is disclosed.

The types of genetic engineering that have been performed on these herpesviruses consist of cloning parts of the virus DNA into plasmids in bacteria, reconstructuring the virus DNA while in the cloned state so that the DNA contains deletions of certain sequences, and furthermore adding foreign DNA sequences either in place of the deletions or at sites removed from the deletions.

A foreign gene of interest targeted for insertion into the genome of HVT may be obtained from any pathogenic organism of interest. Typically, the gene of interest will be derived from pathogens that cause diseases in poultry that have an economic impact on the poultry industry. The genes may be derived from organisms for which there are existing vaccines, and because of the novel advantages of the vectoring technology the HVT derived vaccines will be superior. Also, the gene of interest may be derived from pathogens for which there is currently no vaccine but where there is a requirement for control of the disease. Typically, the gene of interest encodes immunogenic polypeptides of the pathogen, and may represent surface proteins, secreted proteins and structural proteins.

A relevant avian pathogen that is a target for HVT vectoring in the present invention is Infectious Laryngotracheitis virus (ILT). ILT is a member of the herpesviridiae family, and this pathogen is causes an acute disease of chickens which is characterized by respiratory depression, gasping and expectoration of bloody exudate. Viral replication is limited to cells of the respiratory tract, where in the trachea the infection gives rise to tissue erosion and hemorrhage. In chickens, no drug has been effective in reducing the degree of lesion formation or in decreasing clinical signs. Vaccination of birds with various modified forms of the ILT virus derived by cell passage and/or tedious regimes of administration have conferred acceptable protection in susceptible chickens. Because of the degree of attenuation of current ILT vaccines care must be taken to assure that the correct level of virus is maintained; enough to provide protection, but not enough to cause disease in the flock.

An additional target for the HVT vectoring approach and a subject of this invention is Newcastle disease, an infectious, highly contagious and debilitating disease that is caused by the Newcastle disease virus (NDV). NDV is a single-stranded RNA virus of the paramyxovirus family. The various pathotypes of NDV (velogenic, mesogenic, lentogenic) differ with regard to the severity of the disease, the specificity and symptoms, but most types seem to infect the respiratory system and the nervous system. NDV primarily infects chickens, turkeys and other avian species. Historically vaccination has been used to prevent disease, but because of maternal antibody interferences, life-span of the bird and route of administration, the producer needs to adapt immunization protocols to fit specific needs.

SUMMARY OF THE INVENTION

The present invention provides a recombinant herpesvirus of turkeys (HVT) which comprises the genomic DNA of herpesvirus of turkey containing foreign DNA not usually present within such genomic DNA. The foreign DNA is inserted within a region of the genomic DNA which is not essential for replication of the herpesvirus of turkeys and DNA corresponding to a promoter is located upstream of the said foreign DNA.

The invention provides for a homology vector for producing a recombinant herpesvirus of turkeys by inserting foreign DNA into the genomic DNA of a herpesvirus of turkeys. The homology vector comprises a double-stranded DNA molecule consisting essentially of a double-stranded foreign DNA not usually present within the herpesvirus of turkeys genomic DNA, with at one end of the foreign DNA, double-stranded herpesvirus of turkeys DNA homologous to genomic DNA located at one side of a site on the genomic DNA which is not essential for replication of the herpesvirus of turkeys, and at the other end of the foreign DNA, double-stranded herpesvirus of turkeys DNA homologous to genomic DNA located at the other side of the same site on the genomic DNA.

Details of HVT Construction and Map Data

A. BamHI restriction fragment map of HVT. Fragments are numbered in order of decreasing size; letters refer to small fragments whose comparative size has not been determined.

B. BamHI #16 fragment showing location of β-galactosidase gene insertion in S-HVT-001.

C. BamHI #19 fragment showing location of β-galactosidase gene insertion.

Legend: B=BamHI; X=XhoI; H=HindIII; P=PstI; S=SalI; N=NdeI; R=EcoRI.

FIG. 2A, FIG. 2B, FIG. 2C and FIG. 2D

Insertion in Plasmid 191-47

FIGS. 3A–3B

Details of S-HVT-003 Construction

A. Restriction map of HVT DNA in the region of the BamHI #16 fragment. This fragment is contained within large HindIII fragment that has no name in the prior art to applicants' knowledge. Shown also is the XhoI site (X) where applicants have made their constructions the XhoI site was first changed to an EcoRI (R) site by use of a "linker" and standard cloning procedures. Also, shows details of the construction of the beta-gal gene and IBVD gene inserted into the BamHI #16 fragment for use in homologous recombination. Both genes were under the control of the PRV gX gene promoter (gX).

B. The S-HVT-003 genome showing the location of the two inserted foreign genes, β-gal and IBDV.

Legend: H=HindIII; B=BamHI; X=XhoI; R=EcoRI; Xb=XbaI; Hp=HpaI; S=SmaI; UL=unique long region; US=unique short region; IR=internal repeat region; TR=terminal repeat region.

FIG. 4

Western blot showing the differential expression of the IBDV 32 kD antigen in cellular lysates of S-HVT-003 infected cells (32 kD present) and S-HVT-001 infected cells (32 kD negative). IBDV specific polypeptides were identified by probing the blot with hyper-immune rat antiserum directed against denatured IBDV virions. This serum reacts primarily with the immunodominant 32 kD antigen (VP3). The lanes on the blot contain: 1) Protein Molecular Weight Standards, 2) uninfected CEF cells, 3) S-HVT-001 infected CEF's, 4) 5) & 6) S-HVT-003 and 7) IBDV virion polypeptides.

FIG. 5

Western blot showing the presence of the 42 kD IBDV polypeptide (VP2) product in cellular lysates derived from CEF cells infected with either wild-type HVT virus or with S-HVT-001 that expresses β-galactosidase. IBDV specific polypeptides were identified using a VP-2 specific rabbit anti-peptide antiserum. The lanes contain: 1) Protein Molecular Weight Standards, 2) wild-type HVT infected CEF's, 3) S-HVT-001 infected CEF's, 4) S-HVT-003 infected CEF's, 5) S-HVT-003 infected CEF's, and 6) IBDV virion polypeptides.

FIGS. 6A–6C

Details of S-HVT-004 Construction

A. Restriction map of HVT DNA in the region of the BamHI #16 fragment. This fragment is contained within a large HindIII fragment that has no name in the prior art to applicants' knowledge. Shown also is the XhoI site (X) where applicants have made their insertion: for these constructions the XhoI site was first changed to an EcoRI (R) site by use of a "linker" and standard cloning procedures.

B. Details of the construction of the β-gal gene and MDV gA gene inserted into the BamHI #16 fragment for use in homologous recombination. Beta-gal was under the control of the PRV gX gene promoter (gX), while the MDV gA gene was under the control of its own promoter.

C. The S-HVT-004 genome showing the location of the two inserted foreign genes, β-gal and MDV gA.

Legend: H=HindIII; B=BamHI; X=XhoI; R=EcoRI; Xb=XbaI; UL=unique long region; US=unique short region; IR=internal repeat region; TR=terminal repeat region.

FIG. 7A and FIG. 7B

FIG. 7 is a detailed description of the β-galactosidase (lacZ) marker gene insertion in homology vector 467-22.A12. The diagram shows the orientation of DNA fragments assembled in the marker gene. The origin of each fragment is described in the Materials and Methods section. The sequences located at the junctions between each fragment and at the ends of the marker gene are shown. The restriction sites used to generate each fragment are indicated at the appropriate junction. The location of the lacZ gene coding region is also given. Numbers in parenthesis ( ) refer to amino acids, and restriction sites in brackets [ ] indicate the remnants of sites which were destroyed during construction. The following abbreviations are used, pseudorabies virus (PRV), lactose operon Z gene (lacZ), *Escherichia coil* (*E. Coli*), poly adenylation signal (pA), and glycoprotein X (gpx).

FIG. 8

FIG. 8 is a BamHI, NotI restriction map of the HVT genome. The unique long UL and unique short US regions are shown. The long and short region repeats are indicated by boxes. The BamHI fragments are numbered in decreasing order of size. The location of probes P1–P4 are indicated. The origin of each probe is as follows: P1—BamHI #6, P2—BamHI #2, P3—BamHI #13, and P4—4.0 kb BglII to StuI sub-fragment of HVT genomic XbaI fragment #5 (8.0 kb).

FIG. 9

FIG. 9 describes the creation of plasmid pSY229.

FIG. 10A and FIG. 10B

Detailed description of the MDV gene cassette insert in Homology Vectors 456-18.18 and 456-17.22. The diagram shows the orientation of DNA fragments assembled in the cassette. The origin of each fragment is described in the Materials and Methods section. The sequences located at the junctions between each fragment and at the ends of the marker gene are shown, including junction A (SEQ ID NO: 34), junction B (SEQ ID NO: 35), and junction C (SEQ ID NO: 36). The restriction sites used to generate each fragment are indicated at the appropriate junction. The location of the MDV gA and gB genes is also given. Numbers in parenthesis ( ) refer to amino acids, and restriction sites in brackets [ ] indicate the remnants of sites which were destroyed during construction.

FIG. 11A and FIG. 11B

Detailed description of the HindIII fragment insert in Homology Vector 556-41.5. The diagram shows the orientation of DNA fragments assembled in the cassette. The origin of each fragment is described in the Materials and Methods section. The sequences located at the junctions between each fragment and at the ends of the marker gene are shown, including junction A (SEQ ID NO: 37), junction B (SEQ ID NO: 38), and junction C (SEQ ID NO: 39). The restriction sites used to generate each fragment are indicated at the appropriate junction. The location of the MDV gD and a portion of the gI gene is also given. Numbers in parenthesis ( ) refer to amino acids, and restriction sites in brackets [ ] indicate the remnants of sites which were destroyed during construction.

Figure 12B:
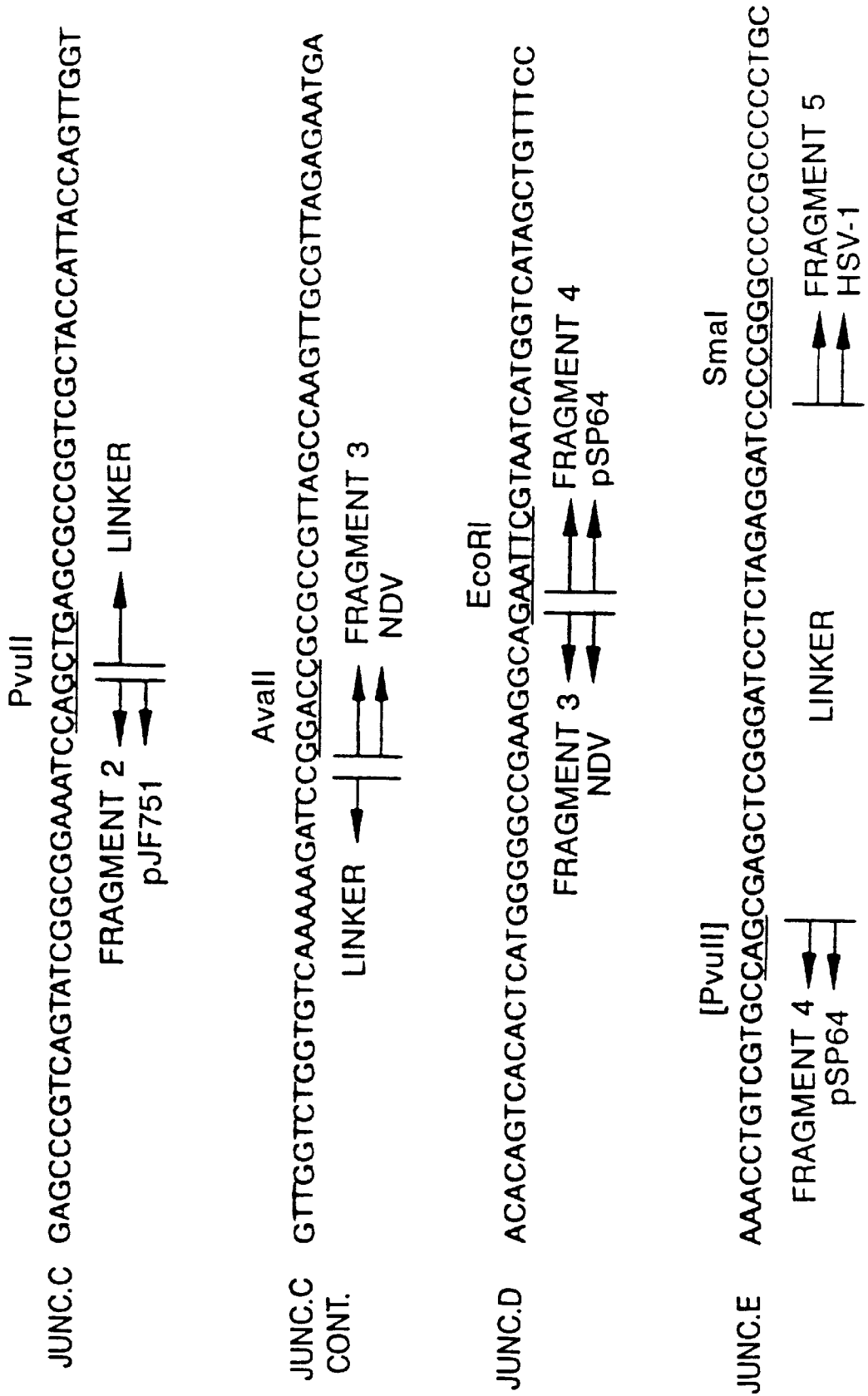

FIG. 12A, FIG. 12B and FIG. 12C

Detailed description of the SalI fragment insert in Homology Vector 255-18.B16. The diagram shows the orientation of DNA fragments assembled in the cassette. The origin of each fragment is described in the Materials and Methods section. The sequences located at the junctions between each fragment and at the ends of the marker gene are shown, including junction A (SEQ ID NO: 40), junction B (SEQ ID NO: 41), junction C (SEQ ID NO: 42), junction D (SEQ ID NO: 43), junction E (SEQ ID NO: 44), junction F(SEQ ID NO: 45), junction G (SEQ ID NO: 46), and junction H (SEQ ID NO: 47). The restriction sites used to generate each fragment are indicated at the appropriate junction. The location of the NDV F and lacZ-NDV HN hybrid gene are shown. Numbers in parenthesis ( ) refer to amino acids, and restriction sites in brackets [ ] indicate the remnants of sites which were destroyed during construction.

DETAILED DESCRIPTION OF THE INVENTION

The present invention provides a recombinant herpesvirus of turkeys (HVT) which comprises the genomic DNA of herpesvirus of turkey containing foreign DNA not usually present within such genomic DNA. The foreign DNA is inserted within a region of the genomic DNA which is not essential for replication of the herpesvirus of turkeys and DNA corresponding to a promoter is located upstream of the said foreign DNA.

For purposes of this invention, "genomic DNA" means the entire DNA which the naturally occurring herpesvirus of turkeys contains. For purposes of this invention, "foreign DNA" means any DNA that is exogenous to the genomic DNA.

For purposes of this invention, a "promoter" is a specific DNA sequence on the DNA molecule to which the foreign RNA polymerase attaches and at which transcription of the foreign RNA is initiated.

The invention further provides recombinant herpesvirus of turkeys whose genomic DNA contains foreign DNA which encodes a polypeptide. Preferably, the polypeptide is antigenic in the animal into which the recombinant HVT is introduced.

Preferably, this antigenic polypeptide is a linear polymer of more than 10 amino acids linked by peptide bonds which stimulates the animal to produce antibodies.

The invention further provides an insertion site present within BamHI #16 fragment of the herpesvirus of turkeys genome. Preferably, the insertion site is within an open reading frame encoding UL43 protein. Preferably, the insertion site is the XhoI restriction endonuclease site located within an open reading frame encoding UL43 protein.

For purposes of this invention, an "open reading frame" is a segment of DNA which contains codons that can be transcribed into RNA which can be translated into an amino acid sequence and which does not contain a termination codon.

The invention further provides an insertion site within EcoRI #9 fragment of the herpesvirus of turkeys genome. Preferably, the insertion site is XhoI restriction endonuclease site located within the EcoRI #9 fragment.

The invention further provides an insertion site within US2 gene coding region of the herpesvirus of turkeys genome. Preferably, the insertion site is StuI restriction endonuclease site located within the US2 gene coding region.

The invention further provides a recombinant herpesvirus of turkeys whose genomic DNA contains foreign DNA encoding a polypeptide which is a detectable marker. Preferably, the detectable marker is E. coli beta-galactosidase. For purposes of this invention, a "polypeptide which is a detectable marker" includes the bimer, trimer and tetramer form of the polypeptide. E. coli β-galactosidase is a tetramer composed of four polypeptides or monomer subunits. Preferably, this recombinant herpesvirus of turkeys is designated S-HVT-001, S-HVT-014, or S-HVT-012. The S-HVT-012 herpesvirus has been deposited pursuant to the Budapest Treaty on the International Deposit of Microorganism for the Purposes of Patent Procedure with the Patent Culture Depository of the American Type Culture Collection, 12301 Parklawn Drive, Rockville, Md. 20852 U.S.A.

The invention further provides a recombinant herpesvirus of turkeys whose genomic DNA contains foreign DNA encoding antigenic polypeptide which is from infectious bursal disease virus, Marek's disease virus, Newcastle disease virus, infectious laryngotracheitis virus, or infectious bronchitis virus.

The invention further provides a recombinant herpesvirus of turkeys whose genomic DNA contains foreign DNA encoding antigenic polypeptide which is from infectious bursal disease virus. Preferably, antigenic polypeptide is VP2, VP3 or VP4 protein.

The invention further provides a recombinant herpesvirus of turkeys whose genomic DNA contains foreign DNA encoding antigenic polypeptide from infectious bursal disease virus and further comprising foreign DNA encoding a polypeptide which is a detectable marker. Preferably, this recombinant herpesvirus of turkeys is designated S-HVT-003 or S-HVT-096. The S-HVT-003 herpesvirus has been deposited pursuant to the Budapest Treaty on the International Deposit of Microorganism for the Purposes of Patent Procedure with the Patent Culture Depository of the American Type Culture Collection, 12301 Parklawn Drive, Rockville, Md. 20852 U.S.A.

The invention further provides recombinant herpesvirus of turkeys whose genomic DNA contains foreign DNA encoding antigenic polypeptide from Marek's disease virus. Preferably, the antigenic polypeptide is Marek's disease virus glycoprotein gB, gA or gD.

The invention further provides recombinant herpesvirus of turkeys whose genomic DNA contains foreign DNA encoding Marek's disease virus glycoprotein gA.

The invention further provides recombinant herpesvirus of turkeys whose genomic DNA contains foreign DNA encoding Marek's disease virus glycoprotein gA and further comprising foreign DNA encoding a polypeptide which is a detectable marker. Preferably, this recombinant herpesvirus of turkeys is designated S-HVT-004. The S-HVT-004 herpesvirus has been deposited pursuant to the Budapest Treaty on the International Deposit of Microorganism for the Purposes of Patent Procedure with the Patent Culture Depository of the American Type Culture Collection, 12301 Parklawn Drive, Rockville, Md. 20852 U.S.A. under ATCC Accession No. VR.

The invention further provides recombinant herpesvirus of turkeys whose genomic DNA contains foreign DNA encoding Marek's disease virus glycoprotein gB. Preferably, this recombinant herpesvirus of turkeys is designated S-HVT-045. The S-HVT-045 herpesvirus has been deposited pursuant to the Budapest Treaty on the International Deposit of Microorganism for the Purposes of Patent Procedure with the Patent Culture Depository of the American Type Culture Collection, 12301 Parklawn Drive, Rockville, Md. 20852 U.S.A.

This invention further provides recombinant herpesvirus of turkeys whose genomic DNA contains foreign DNA encoding Marek's disease virus glycoprotein gB and further comprising foreign DNA encoding Marek's disease virus glycoprotein gA. Preferably, this recombinant herpesvirus of turkeys is designated S-HVT-046 or S-HVT-047.

The invention further provides recombinant herpesvirus of turkeys whose genomic DNA contains foreign DNA encoding Marek's disease virus glycoprotein gB, Marek's disease virus glycoprotein gA, and Marek's disease virus glycoprotein gD. Preferably, this recombinant herpesvirus of turkeys is designated S-HVT-048.

The invention further provides recombinant herpesvirus of turkeys whose genomic DNA contains foreign DNA encoding antigenic polypeptide from Newcastle disease virus. Preferably, this antigenic polypeptide is Newcastle disease virus fusion (F) protein or Newcastle disease virus hemagglutinin-neuraminidase (HN) protein.

The invention further provides recombinant herpesvirus of turkeys whose genomic DNA contains foreign DNA encoding Newcastle disease virus fusion (F) protein and further comprising foreign DNA encoding a recombinant protein, wherein E. coli beta-galactosidase is fused to Newcastle disease virus hemmagglutinin-neuraminidase (HN) protein. Preferably, this recombinant herpesvirus of turkeys is designated S-HVT-007.

The invention further provides recombinant herpesvirus of turkeys whose genomic DNA contains foreign DNA encoding antigenic polypeptide from Marek's disease virus and further comprising foreign DNA encoding antigenic polypeptide from Newcastle disease virus.

The invention further provides recombinant herpesvirus of turkeys whose genomic DNA contains foreign DNA encoding Marek's disease virus glycoprotein gB and Marek's disease virus glycoprotein gA and further comprising foreign DNA encoding Newcastle disease virus fusion (F) protein. Preferably, this recombinant herpesvirus of turkeys is designated S-HVT-048.

The invention further provides recombinant herpesvirus of turkeys whose genomic DNA contains foreign DNA encoding Marek's disease virus glycoprotein gB and Marek's disease virus glycoprotein gA and further comprising foreign DNA encoding Newcastle disease virus hemagglutinin-neuraminidase (HN) protein. Preferably, this recombinant herpesvirus of turkeys is designated S-HVT-049.

The invention further provides recombinant herpesvirus of turkeys whose genomic DNA contains foreign DNA encoding Marek's disease virus glycoprotein gB and Marek's disease virus glycoprotein gA and further comprising foreign DNA encoding Newcastle disease virus fusion (F) protein and Newcastle disease virus hemagglutinin-neuraminidase (HN) protein. Preferably, this recombinant herpesvirus of turkeys is designated S-HVT-050.

The invention further provides recombinant herpesvirus of turkeys whose genomic DNA contains foreign DNA encoding Marek's disease virus glycoprotein gB, Marek's disease virus glycoprotein gA, and Marek's disease virus glycoprotein gD and further comprising foreign DNA encoding Newcastle disease virus fusion (F) protein and foreign DNA encoding Newcastle disease virus hemagglutinin-neuraminidase (HN) protein. Preferably, this recombinant herpesvirus of turkeys is designated S-HVT-106.

The invention further provides recombinant herpesvirus of turkeys whose genomic DNA contains foreign DNA encoding infectious laryngotracheitis virus glycoprotein gB or infectious laryngotracheitis virus glycoprotein gD. Preferably, this recombinant herpesvirus of turkeys is designated S-HVT-051 or S-HVT-052.

The invention further provides recombinant herpesvirus of turkeys whose genomic DNA contains foreign DNA encoding antigenic polypeptide from Marek's disease virus and further comprising foreign DNA encoding antigenic polypeptide from infectious laryngotracheitis virus.

The invention further provides recombinant herpesvirus of turkeys whose genomic DNA contains foreign DNA encoding Marek's disease virus glycoprotein gA and further comprising foreign DNA encoding infectious laryngotracheitis virus glycoprotein gD and foreign DA encoding infectious laryngotracheitis virus glycoprotein gB. Preferably, this recombinant herpesvirus of turkeys is designated S-HVT-096.

The invention further provides recombinant herpesvirus of turkeys whose genomic DNA contains foreign DNA encoding Marek's disease virus glycoprotein gB, Marek's disease virus glycoprotein gA, and Marek's disease virus glycoprotein gD and further comprising foreign DNA which encodes infectious laryngotracheitis virus glycoprotein gD, infectious laryngotracheitis virus glycoprotein gB, and E. coli beta-galactosidase. Preferably, this recombinant herpesvirus of turkeys is designated S-HVT-104.

The invention further provides recombinant herpesvirus of turkeys whose genomic DNA contains foreign DNA encoding infectious bronchitis virus spike protein or infectious bronchitis virus matrix protein.

The invention further provides recombinant herpesvirus of turkeys whose genomic DNA contains foreign DNA encoding antigenic polypeptide from Marek's disease virus and further comprising foreign DNA encoding infectious bronchitis virus spike protein or infectious bronchitis matrix protein. Preferably, this recombinant herpesvirus of turkeys is designated S-HVT-066.

The inserted foreign DNA is under the control of a promoter. Preferably, the promoter is a herpesvirus promoter. Preferably, the promoter is selected from PRV gX, HSV-1 alpha 4, HCMV immediate early, MDV gB, MDV gD, ILT gB, and ILT gD. For purposes of this invention, the promoters were generated by methods well known to those of skill in the art.

The invention provides for a homology vector for producing a recombinant herpesvirus of turkeys by inserting foreign DNA into the genomic DNA of a herpesvirus of turkeys. The homology vector comprises a double-stranded DNA molecule consisting essentially of a double-stranded foreign DNA not usually present within the herpesvirus of turkeys genomic DNA, with at one end of the foreign DNA, double-stranded herpesvirus of turkeys DNA homologous to genomic DNA located at one side of a site on the genomic DNA which is not essential for replication of the herpesvirus of turkeys, and at the other end of the foreign DNA, double-stranded herpesvirus of turkeys DNA homologous to genomic DNA located at the other side of the same site on the genomic DNA. DNA sequence corresponding to a promoter is located upstream of the foreign DNA and controls the expression of the foreign DNA.

In one embodiment of the invention, the foreign DNA encodes a polypeptide. In one embodiment of the invention, the polypeptide is antigenic in the animal into which the recombinant herpesvirus of turkeys is introduced.

Preferably, the antigenic polypeptide is from infectious bursal disease virus, Marek's disease virus, Newcastle disease virus, infectious laryngotracheitis virus, or infectious bronchitis virus. Preferably, the antigenic polypeptide is selected from a group consisting of infectious bursal disease virus VP2 protein, infectious bursal disease virus VP3 protein, infectious bursal disease virus VP4 protein, Marek's disease virus glycoprotein gB, Marek's disease virus glycoprotein gA, Marek's disease virus glycoprotein gD, Newcastle disease virus fusion (F) protein, Newcastle disease virus hemagglutinin-neuraminidase (HN) protein, infectious laryngotracheitis virus glycoprotein gB, infectious laryngotracheitis virus glycoprotein gD, infectious bronchitis virus spike protein, or infectious bronchitis virus matrix protein.

In one embodiment of the invention, the polypeptide is a detectable marker. Preferably, the polypeptide which is a detectable marker is *E. coli* beta-galactosidase.

In one embodiment of the invention, the double-stranded herpesvirus of turkeys DNA is homologous to DNA sequences present within the BamHI #16 fragment of the herpesvirus of turkeys genome. Preferably, the double-stranded herpesvirus of turkeys DNA is homologous to DNA sequences present within the open reading frame encoding UL 43 protein of the herpesvirus of turkeys genome. Preferably, this homology vector is designated 172-29.31.

For purposes of this invention, a "homology vector" is a plasmid constructed to insert foreign DNA in a specific site on the genome of a herpesvirus of turkeys.

In one embodiment of the invention, the double-stranded herpesvirus of turkeys DNA is homologous to DNA sequences present within the EcoRI #9 fragment of the herpesvirus of turkeys genome. Preferably, this homology vector is designated 172-63.1.

In one embodiment of the invention, the double-stranded herpesvirus of turkeys DNA is homologous to DNA sequences present within the US2 gene coding region of the herpesvirus of turkeys genome. Preferably, this homology vector is designated 435-47.1.

The invention further provides a vaccine which comprises an effective immunizing amount of a recombinant herpesvirus of turkeys of the present invention and a suitable carrier.

Suitable carriers for the herpesvirus of turkeys are well known in the art and include proteins, sugars, etc. One example of such a suitable carrier is a physiologically balanced culture medium containing one or more stabilizing agents such as stabilized, hydrolyzed proteins, lactose, etc.

For purpose of this invention, an "effective immunizing amount" of recombinant herpesvirus of the present invention is within the range of $10^2$ to $10^9$ PFU/dose.

The present invention also provides a method of immunizing a fowl. For purposes of this invention, this includes immunizing a fowl against infectious bursal disease virus, Marek's disease virus, Newcastle disease virus, infectious laryngotracheitis virus, or infectious bronchitis virus. The method comprises administering to the fowl an effective immunizing dose of the vaccine of the present invention. The vaccine may be administered by any of the methods well known to those skilled in the art, for example, by intramuscular, subcutaneous, intraperitoneal or intravenous injection. Alternatively, the vaccine may be administered intranasally or orally.

The present invention also provides a host cell infected with a recombinant herpesvirus of turkeys. Preferably, the host cell is an avian cell.

For purposes of this invention, a "host cell" is a cell used to propagate a vector and its insert. Infecting the cell was accomplished by methods well known to those skilled in the art, for example, as set forth in DNA TRANSFECTION FOR GENERATING RECOMBINANT HERPESVIRUS in *Materials and Methods*.

A recombinant herpesvirus of turkeys of the present invention provide a way for distinguishing an animal vaccinated with the vaccine of the present invention from an animal infected with a naturally-occurring, wild-type infectious bursal disease virus, Marek's disease virus, Newcastle disease virus, infectious laryngotracheitis virus, or infectious bronchitis virus. This is possible because recombinant herpesvirus of turkeys contain foreign DNA which encodes a limited number of antigens from the above mentioned viruses that are needed to confer protective immunity to the corresponding pathogens. Consequently, host animals vaccinated with the recombinant herpesvirus of turkeys can be distinguished from those which have been infected with wild-type infectious bursal disease virus, Marek's disease virus, Newcastle disease virus, infectious laryngotracheitis virus, or infectious bronchitis virus by the absence of antigens that are normally present in the wild type viruses.

Methods for constructing, selecting and purifying recombinant herpesvirus of turkeys are detailed below in *Materials and Methods*.

MATERIALS AND METHODS

PREPARATION OF HERPESVIRUS OF TURKEYS STOCK SAMPLES. Herpesvirus of turkeys stock samples were prepared by infecting tissue culture cells at a multiplicity of infection of 0.01 PFU/cell in Dulbecco's Modified Eagle Medium (DMEM) containing 2 Mm glutamine, 100 units/ml penicillin, 100 units/ml streptomycin (these components are obtained from Irvine Scientific or an equivalent supplier, and hereafter are referred to as complete DME medium) plus 1% fetal bovine serum. After cytopathic effect was complete, the medium and cells were harvested and the cells were pelleted at 3000 rpm for 5 minutes in a clinical centrifuge. Infected cells were resuspended in complete medium containing 20% fetal bovine serum, 10% DMSO and stored frozen at −70° C.

PREPARATION OF HERPESVIRUS OF TURKEY DNA. All manipulations of herpesvirus of turkey (HVT) were made using strain FC-126 (ATCC #584-C). For the preparation of HVT viral DNA from the cytoplasm of infected cells, primary chicken embryo fibroblasts were infected at a MOI sufficient to cause extensive cytopathic effect before the cells overgrew. All incubations were carried out at 39° C. in a humidified incubator with 5% $CO_2$ in air. Best DNA yields were obtained by harvesting monolayers which were maximally infected, but showing incomplete cell lysis (typically 5–7 days). Infected cells were harvested by scraping the cells into the medium using a cell scraper (Costar brand). The cell suspension was centrifuged at 3000 rpm for 10 minutes at 5° C. in a GS-3 rotor (Sorvall Instruments). The resultant pellet was resuspended in cold PBS (20 ml/Roller Bottle) and subjected to another centrifugation for 10 minutes at 3000 rpm in the cold. After decanting the PBS, the cellular pellet was resuspended in 4 ml/roller bottle of RSB buffer (10 mM Tris pH 7.5, 1 mM EDTA, and 1.5 mM $MgCl_2$). NP40 (Nonidet P-40™; Sigma) was added to the sample to a final concentration of 0.5% and allowed to incubate on ice for 15 minutes with occasional mixing. The sample was centrifuged for 10 minutes at 3000 rpm in the cold to pellet the nuclei and remove cellular debris. The supernatant fluid was carefully transferred to a 15 ml Corex centrifuge tube. Both EDTA (0.5M pH 8.0) and SDS (sodium dodecyl sulfate; stock 20%) were added to the sample to final concentrations of 5 mM and 1%, respectively. One hundred µl of proteinase-K (10 mg/ml; Boehringer Mannheim) was added per 4 ml of sample, mixed, and incubated at 45° C. for 1–2 hours. After this period, an equal volume of water-saturated phenol was added to the sample and gently mixed by hand. The sample was spun in a clinical centrifuge for 5 minutes at 3000 rpm to separate the phases. NaAc was added to the aqueous phase to a final concentration of 0.3M (stock solution 3M pH 5.2), and the nucleic acid precipitated at −70° C. for 30 minutes after the addition of 2.5 volumes of cold absolute ethanol. DNA in the sample was pelleted by spinning for 20 minutes to 8000 rpm in an HB-4 rotor at 5° C. The supernatant was carefully removed and the DNA pellet washed once with 25 ml of 80% ethanol. The DNA pellet was dried briefly by vacuum (2–3 minutes), and resuspended in 50 µl/roller bottle of infected cells of TE buffer (10 mM Tris pH 7.5, 1 mM EDTA). Typically, yields of viral DNA ranged between 5–10 µg/roller bottle of infected cells. All viral DNA was stored at approximately 10° C.

POLYMERASE FILL-IN REACTION. DNA was resuspended in buffer containing 50 mM Tris pH 7.4, 50 mM KCl, 5 mM $MgCl_2$, and 400 micromolar each of the four deoxynucleotides. Ten units of Klenow DNA polymerase (BRL) were added and the reaction was allowed to proceed for 15 minutes at room temperature. The DNA was then phenol extracted and ethanol precipitated as above.

DNA SEQUENCING. Sequencing was performed using the USB Sequenase Kit and $^{35}$S-dATP (NEN). Reactions using both the dGTP mixes and the dITP mixes were performed to clarify areas of compression. Alternatively, compressed areas were resolved on formamide gels. Templates were double-stranded plasmid subclones or single stranded M13 subclones, and primers were either made to the vector just outside the insert to be sequenced, or to previously obtained sequence. Sequence obtained was assembled and compared using Dnastar software. Manipulation and comparison of sequences obtained was performed with Superclone and Supersee programs from Coral Software.

MOLECULAR BIOLOGICAL TECHNIQUES. Techniques for the manipulation of bacteria and DNA, including such procedures as digestion with restriction endonucleases, gel electrophoresis, extraction of DNA from gels, ligation, phosphorylation with kinase, treatment with phosphatase, growth of bacterial cultures, transformation of bacteria with DNA, and other molecular biological methods are described by Maniatis et al (1982) and Sambrook et al (1989). The polymerase chain reaction (PCR) was used to introduce restriction sites convenient for the manipulation of various DNAs. The procedures used are described by Innis et al (1990). In general amplified fragments were less than 500 base pairs in size and critical regions of amplified fragments were confirmed by DNA sequencing. Except as noted, these techniques were used with minor variation.

SOUTHERN BLOTTING OF DNA. The general procedure for Southern blotting was taken from Maniatis et al. (1982). DNA was blotted to nitrocellulose filters (S&S BA85) in 20× SSC (1×ssc=0.15M NaCl, 0.015M sodium citrate, pH 7.0), and prehybridized in hybridization solution consisting of 30% formamide, 1× Denhardt's solution (0.02% polyvinylpyrrolidone (PVP), 0.02% bovine serum albumin (BSA), 0.02% Ficoll), 6× SSC, 50 mM $NaH_2PO_4$, pH 6.8, 200 µg/ml salmon sperm DNA for 4–24 hours at 55° C. Labeled probe DNA was added that had been labeled by nick translation using a kit from Bethesda Research Laboratories (BRL) and one $^{32}$P-labeled nucleotide. The probe DNA was separated from the unincorporated nucleotides by NACS column (BRL) or on a Sephadex G50 column (Pharmacia). After overnight hybridization at 55° C., the filter was washed once with 2× SSC at room temperature followed by two washes with 0.1× SSC, 0.1% sodium dodecyl sulfate (SDS) for 30 minutes at 55° C. The filter was dried and autoradiographed.

cDNA CLONING PROCEDURE. cDNA cloning refers to the methods used to convert RNA molecules into DNA molecules following state of the art procedures. Applicants' methods are described in (Gubler and Hoffman, 1983). Bethesda Research Laboratories (Gaithersburg, Md.) have designed a cDNA Cloning Kit that is very similar to the procedures used by applicants, and contains a set of reagents and protocols that may be used to duplicate our results.

For cloning virus mRNA species, a host cell line sensitive to infection by the virus was infected at 5–10 plaque forming units per cell. When cytopathic effect was evident, but before total destruction, the medium was removed and the cells were lysed in 10 mls lysis buffer (4 M guanidine thiocyanate, 0.1% antifoam A, 25 mM sodium citrate pH 7.0, 0.5% N-lauroyl sarcosine, 0.1 M beta-mercaptoethanol). The cell lysate was poured into a sterilized Dounce homogenizer and homogenized on ice 8–10 times until the solution was homogenous. For RNA purification, 8 mls of cell lysate were gently layered over 3.5 mls of CsCl solution (5.7 M CsCl, 25 mM sodium citrate pH 7.0) in a Beckman SW41 centrifuge tube. The samples were centrifuged for 18 hrs at 20° C. at 36000 rpm in a Beckman SW41 rotor. The tubes were put on ice and the supernatants from the tubes were carefully removed by aspiration to leave the RNA pellet undisturbed. The pellet was resuspended in 400 µl glass distilled water, and 2.6 mls of guanidine solution (7.5 M guanidine-HCl, 25 mM sodium citrate pH 7.0, 5 mM dithiothreitol) were added. Then 0.37 volumes of 1 M acetic acid were added, followed by 0.75 volumes of cold ethanol and the sample was put at −20° C. for 18 hrs to precipitate RNA. The precipitate was collected by centrifugation in a Sorvall centrifuge for 10 min at 4° C. at 10000 rpm in an SS34 rotor. The pellet was dissolved in 1.0 ml distilled water, recentrifuged at 13000 rpm, and the supernatant saved. RNA was re-extracted from the pellet 2 more times as above with 0.5 ml distilled water, and the supernatants were pooled. A 0.1 volume of 2 M potassium acetate solution was added to the sample followed by 2 volumes of cold ethanol and the sample was put at −20° C. for 18 hrs. The precipitated RNA was collected by centrifugation in the SS34 rotor at 4° C. for 10 min at 10000 rpm. The pellet was dissolved in 1 ml distilled water and the concentration taken by adsorption at A260/280. The RNA was stored at −70° C.

mRNA containing polyadenylate tails (poly-A) was selected using oligo-dT cellulose (Pharmacia #27 5543-0). Three mg of total RNA was boiled and chilled and applied to a 100 mg oligo-dT cellulose column in binding buffer (0.1 M Tris pH 7.5, 0.5 M LiCl, 5 mM EDTA pH 8.0, 0.1% lithium dodecyl sulfate). The retained poly-$A^+$ RNA was eluted from the column with elution buffer (5 mM Tris pH 7.5, 1 mM EDTA pH 8.0, 0.1% sodium dodecyl sulfate). This mRNA was reapplied to an oligo-dT column in binding buffer and eluted again in elution buffer. The sample was precipitated with 200 mM sodium acetate and 2 volumes cold ethanol at −20° C. for 18 hrs. The RNA was resuspended in 50 µl distilled water.

Ten µg poly-$A^+$ RNA was denatured in 20 mM methyl mercury hydroxide for 6 min at 22° C. β-mercaptoethanol was added to 75 mM and the sample was incubated for 5 min at 22° C. The reaction mixture for first strand cDNA synthesis in 0.25 ml contained 1 μg oligo-dT primer (P-L Bio-chemicals) or 1 μg synthetic primer, 28 units placental ribonuclease inhibitor (Bethesda Research Labs #5518SA), 100 mM Tris pH 8.3, 140 mM KCl, 10 mM MgCl$_2$, 0.8 mM DATP, dCTP, dGTP, and dTTP (Pharmacia), 100 microcuries $^{32}$P-labeled dCTP (New England Nuclear #NEG-013H), and 180 units AMV reverse transcriptase (Molecular Genetics Resources #MG 101). The reaction was incubated at 42° C. for 90 min, and then was terminated with 20 mM EDTA pH 8.0. The sample was extracted with an equal volume of phenol/chloroform (1:1) and precipitated with 2 M ammonium acetate and 2 volumes of cold ethanol −20° C. for 3 hrs. After precipitation and centrifugation, the pellet was dissolved in 100 μl distilled water. The sample was loaded onto a 15 ml G-100 Sephadex column (Pharmacia) in buffer (100 mM Tris pH 7.5, 1 mM EDTA pH 8.0, 100 mM NaCl). The leading edge of the eluted DNA fractions was pooled, and DNA was concentrated by lyophilization until the volume was about 100 μl, then the DNA was precipitated with ammonium acetate plus ethanol as above.

The entire first strand sample was used for second strand reaction which followed the Gubler and Hoffman (1983) method except that 50 μg/ml dNTP's, 5.4 units DNA polymerase I (Boerhinger Mannheim #642-711), and 100 units/ml E. coli DNA ligase (New England Biolabs #205) in a total volume of 50 microliters were used. After second strand synthesis, the CDNA was phenol/chloroform extracted and precipitated. The DNA was resuspended in 10 μl distilled water, treated with 1 μg RNase A for 10 min at 22° C., and electrophoresed through a 1% agarose gel (Sigma Type II agarose) in 40 mM Tris-acetate buffer pH 6.85. The gel was stained with ethidium bromide, and DNA in the expected size range was excised from the gel and electroeluted in 8 mM Tris-acetate pH 6.85. Electroeluted DNA was lyophilized to about 100 microliters, and precipitated with ammonium acetate and ethanol as above. The DNA was resuspended in 20 μl water.

Oligo-dC tails were added to the DNA to facilitate cloning. The reaction contained the DNA, 100 mM potassium cacodylate pH 7.2, 0.2 mM dithiothreitol, 2 mM CaCl$_2$, 80 μmoles dCTP, and 25 units terminal deoxynucleotidyl transferase (Molecular Genetic Resources #S1001) in 50 μl. After 30 min at 37° C., the reaction was terminated with 10 mM EDTA, and the sample was phenol/chloroform extracted and precipitated as above.

The dC-tailed DNA sample was annealed to 200 ng plasmid vector pBR322 that contained oligo-dG tails (Bethesda Research Labs #5355 SA/SB) in 200 μl of 0.01 M Tris pH 7.5, 0.1 M NaCl, 1 mM EDTA pH 8.0 at 65° C. for 2 min and then 57° C. for 2 hrs. Fresh competent E. coli DH-1 cells were prepared and transformed as described by Hanahan (1983) using half the annealed cDNA sample in twenty 200 μl aliquots of cells. Transformed cells were plated on L-broth agar plates plus 10 μg/ml tetracycline. Colonies were screened for the presence of inserts into the ampicillin gene using Ampscreen\(Bethesda Research Labs #5537 UA), and the positive colonies were picked for analysis.

DNA TRANSFECTION FOR GENERATING RECOMBINANT HERPESVIRUS. The method is based upon the polybrene-DMSO procedure of Kawai and Nishizawa (1984) with the following modifications. Generation of recombinant HVT virus is dependent upon homologous recombination between HVT viral DNA and the plasmid homology vector containing the desired foreign DNA flanked by the appropriate herpesvirus cloned sequences. Transfections were carried out in 6 cm plates (Corning plastic) of 50% confluent primary chick embryo fibroblast (CEF) cells. The cells were plated out the day before in CEF growth media (1× F10/199, 5% fetal calf serum, 2% glutamine, 1% non-essential amino acids, and 2% penicillin/streptomycin) containing 4 μg/ml polybrene (stock 4 mg/ml in 1×HBSS). For cotransfections into CEF cells, 5 μg of the plasmid homology vector was mixed with 5 μg of intact HVT DNA, and suspended in 1 ml of CEF media containing 30 μg/ml polybrene (stock 4 mg/ml in 1× HBSS). The DNA-polybrene suspension (1 ml) was then added to a 6 cm plate of CEF cells from which the media had been aspirated, and incubated at 39° C. for 30 minutes. The plates were rocked periodically during this time to redistribute the inoculum. After this period, 4 ml of CEF growth media was added directly to wash plate, and incubated an additional 2.5 hours at 39° C. At this time, the media was removed from each plate, and the cells shocked with 2 ml of 30% DMSO (Dimethyl Sulfoxide, J.T. Baker Chemical Co.) in 1× HBSS for 4 minutes at room temperature. The 30% DMSO was carefully removed and the monolayers washed once with 1× HBSS at room temperature. The cells were then incubated at 39° C. after the addition of 5 mls of CEF growth media. The next day, the media was changed to remove any last traces of DMSO and to stimulate cell growth. Cytopathic effect from the virus becomes apparent within 6 days. Generation of a high titer stock (80%–90% CPE) can usually be made within 1 week from this date. HVT stock samples were prepared by resuspending the infected cells in CEF growth media containing 20% fetal calf serum, 10% DMSO and stored at −70° C.

PROCEDURE FOR GENERATING RECOMBINANT HERPESVIRUS FROM SUBGENOMIC DNA FRAGMENTS. The ability to generate herpesviruses by cotransfection of cloned overlapping subgenmoic fragments has been demonstrated for pseudorabies virus (Zijl et al., 1988). If deletions and/or insertions are engineered directly into the subgenomic fragments prior to the cotransfection, this procedure results in a high frequency of viruses containing the genomic alteration, greatly reducing the amount of screening required to purify the recombinant virus. We have used this procedure to construct recombinant HVT.

A library of subclones containing overlapping HVT subgenomic fragments was generated as follows. HVT DNA was obtained from the American Type Culture Collection (FC-126 ("Calnek")). It was sheared and then size selected on a glycerol gradient as described by van Zijl et al.,(1988) with 40–50 kb fragments chosen as the insert population. The pooled fractions were diluted twofold with TE, one-tenth volume of 3M NaAc and 2.5 volumes of ethanol were added, and the DNA was precipitated at 30K rpm in a Beckman SW41 rotor for 1 hr. The sheared fragments were given blunt ends by initial treatment with T4 DNA polymerase, using low DNTP concentrations to promote 3' overhang removal, followed by treatment with Klenow polymerase to fill in recessed 3' ends. These insert fragments were then ligated to a pWE15 (Strategene) cosmid vector, which had been digested with BamHI, treated with calf intestinal phosphatase, and made blunt by treatment with Klenow polymerase. The ligated mixture was then packaged using Gigapack XL packaging extracts (Stratagene). Ligation and packaging was as recommended by the manufacturer.

Published restriction maps for the enzymes BamHI, HindIII, and XhoI permitted the use of subcloned fragments as specific probes to screen the cosmid library for subclones spanning the genome. Probes were generated from subcloned restriction fragments. The fragments were then labeled using a non-radioactive system (Genius, Boehringer Mannheim). Screening was facilitated by picking colonies to media followed by growth overnight. Sets of five filters and a master plate were stamped from microtiter dish and again grown overnight. Glycerol was added to the wells to 15% and the plates were frozen at −20° C. to provide stock cultures of each colony. Filters were BioRad Colony Lift Membranes and were treated and hybridized per manufacturer's instructions, and washed in 0.1× SSC, 0.1% SDS, 65° C. Clones which hybridized with the non-radioactive probe were detected according to the Genius kit directions.

Colonies were selected for further analysis on the basis of their hybridization to two or more of the specific probes. These were then digested with BamHI, and compared to published maps of HVT (Buckmaster et al., 1988). The three cosmids (407-32.2C3, 407-32.1G7, and 407-32.5G6) were obtained in this manner. A detailed description of each clone is given below. It was found that chloramphenicol amplification (Maniatis et al., 1982) was necessary to achieve reasonable yields of DNA from these clones. In addition, one cosmid clone (407-32.5G6) was unstable and had to be grown from the original frozen stock in order to obtain satisfactory DNA preparations.

The pWE15 vector allows the inserts to be excised with NotI. However, four NotI sites are present in the HVT genome, so that inserts spanning these sites cannot be excised with NotI. Two of the NotI sites are present in the BamHI #2 fragment of HVT, this fragment was cloned directly in pSP64. The other two sites are present in the unique short region within the BamHI #1 fragment. This fragment was cloned directly in the pWE15 vector. The three sheared cosmids and the two BamHI fragments cover all but a small portion of the ends of the HVT genome. Because these regions are repeated in the internal portions of the genome, all of the genetic information is available.

A StuI site within the HVT US2 gene was established as a useful site for foreign DNA insertion utilizing the HOMOLOGOUS RECOMBINATION PROCEDURE FOR GENERATING RECOMBINANT HERPESVIRUSES (see Example 6). The HVT US2 gene is located within the BamHI #1 fragment which contains five StuI sites. To facilitate the use of this site for insertion of foreign DNA by the StuI site within the US2 gene was converted to a unique HindIII site. This was accomplished by partially digesting the BamHI #1 subclone with StuI, and then inserting a 10 kb fragment conferring kanomycin resistance ($Neo^R$) into the site using HindIII linkers. The kanomycin resistance gene allowed positive selection of recombinant clones. The $Neo^R$ fragment was removed by digestion with HindIII followed by religation generating clone 430-84.215.

DNA was prepared for reconstruction experiments by restriction digestion with enzymes which cut the subclones outside or flanking the HVT insertions. In some instances, one cosmid in a reconstruction was used undigested. Digested DNAs were extracted once with phenol and precipitated with ethanol. DNA was resuspended at a concentration of 0.5 to 1 ug/ml. Viral reconstruction experiments were performed using Lipofectin (BRL) to mediate transfection. Two to three micrograms each of subclone were added to 0.5 ml of MEM media (Earle's salts) supplemented with 1% non-essential amino acids and 2% penicillin/Streptomycin (MEM+). Controls consisted of MEM+ with no DNA, with several ug of HVT DNA, or with 4 out of 5 of the subclones. Separately, 30 μl of the Lipofectin were added to another 0.5 ml. of MEM+. These two mixtures were then combined and incubated at RT for 15 minutes.

Chick embryo fibroblast (CEF) cells were prepared for transfection in the following manner. CEFs (Spafas) were grown in 6 well dishes at 39° C. in F10/M199 (1:1) media containing 1% non-essential amino acids, 2% penicillin/streptomycin, and 5% fetal calf serum (CEF+). Cells were transfected at a confluence of 90–95%. For transfection, wells were aspirated and rinsed 3 times with MEM+, and then incubated 4 hours at 39° C. with the 1 ml lipofectin/DNA mixture above. One ml more of CEF+ was then added to the wells, and cells were incubated overnight and fed with CEF+. Plates were then examined daily for the appearance of plaques.

Lipofectin with control HVT DNA resulted in the appearance of plaques within 5 days. When only four of the five subclones were used, no plaques were obtained. When the five overlapping genomic fragments of HVT were used to reconstruct the virus, plaques appeared anywhere from 5 to 19 days after the initial lipofection. In the case of plaques appearing late, plaques were not initially seen on the infected monolayer, and it was only after passaging the monolayer and replating on a larger surface that plaques appeared. After passaging, plaques generally appeared within 3 days. Recombinant viruses were plaque purified approximately three and then analyzed for insertion of foreign DNAs.

BLUOGAL SCREEN FOR RECOMBINANT HERPESVIRUS. When the foreign gene encoded the enzyme β-galactosidase, the plaques that contained the gene were visualized more easily. The chemical Bluogal™ (Bethesda Research Labs) was incorporated at the level of 200–300 μg/ml into the agarose overlay during the plaque assay, and the plaques that expressed active β-galactosidase turned blue. The blue plaques were then picked and purified by further blue plaque isolations. Other foreign genes were inserted by homologous recombination such that they replaced the β-galactosidase gene; in this instance non-blue plaques were picked for purification of the recombinant virus.

SCREEN FOR FOREIGN GENE EXPRESSION IN RECOMBINANT HVT USING BLACK PLAQUE ASSAYS. To analyze expression of foreign antigens expressed by recombinant HVT viruses, monolayers of CEF cells are infected with recombinant HVT, overlaid with nutrient agarose media and incubated for 4–5 days at 39° C. Once plaques have developed, the agarose overlay is removed from the dish, the monolayer rinsed 1× with PBS, fixed with 100% methanol for 10 minutes at room temperature and the cells air dried. After re-hydrating the plate with PBS, the primary antibody is diluted to the appropriate dilution with PBS and incubated with the cell monolayer for 2 hours to overnight at room temperature. Unbound antibody is then removed from the cells by washing three times with PBS at room temperature. An alkaline phosphatase conjugated secondary antibody is diluted with PBS and incubated with the cells for 2 hours at room temperature. Unbound secondary antibody is then removed by washing the cells three times with PBS at room temperature. Next, the monolayer is rinsed in color development buffer (100 mM Tris pH 9.5/100 mM NaCl/5 mM MgCl2), and then incubated 10 minutes to overnight at room temperature with freshly prepared substrate solution (0.3 mg/ml Nitro Blue tetrazolium+0.15 mg/ml 5-Bromo-4-Chloro-3-Indolyl Phosphatase in color development buffer.) Finally, the reaction is stopped by replacing the substrate solution with TE (10 mM Tris, pH7.5/1 mM EDTA). Plaques expressing the correct antigen will stain black.

PLAQUE HYBRIDIZATION PROCEDURE FOR ASSESSING THE PURITY OF RECOMBINANT HVT STOCKS. When no suitable immunological reagent exists to detect the presence of a particular antigen in a recombinant HVT virus, plaque hybridization can be used to assess the purity of a stock. Initially, CEF cell monolayers are infected with various dilutions of the viral stocks to give ≠50–100 plaques/10 cm.dish, overlaid with nutrient agarose media and incubated for 4–5 days at 39° C. Once plaque development occurs, the position of each plaque is marked on bottom of the dish. The agarose overlay is then removed, the plate washed with PBS, and the remaining CEF monolayer is transferred to a NC membrane or BioRad nylon membrane pre-wetted with PBS (making note of the membrane position relative to the dish). Cells contained on the NC membranes are then lysed by placing the membranes in 1.5 mls of 1.5M NaCl and 0.5M NaOH for five minutes. The membranes are neutralized by placing them in 1.5 mls of 3M Sodium acetate (pH 5.2) for five minutes. DNA from the lysed cells is then bound to the NC membranes by baking at 80° C. for one hour. After this period the membranes are prehybridized in a solution containing 6× SSC, 3% skim milk, 0.5% SDS, (±) salmon sperm DNA (50 µg/ml) for one hour at 65° C. Radio-labeled probe DNA (alpha 32P-dCTP) is then added and the membranes incubated at 65° C. overnight (≠12 hours). After hybridization the NC membranes are washed two times (30 minutes each) with 2× SSC at 65° C., followed by two additional washes at 65° C. with 0.5× SSC. The NC membranes are then dried and exposed to X-ray film (Kodak X-OMAT,AR) at −70° C. for 12 hours. Positive signals are then aligned with the position of the plaques on the dish and purity of the stock is recorded as the percentage of positive plaques over the total.

Figure 7A:
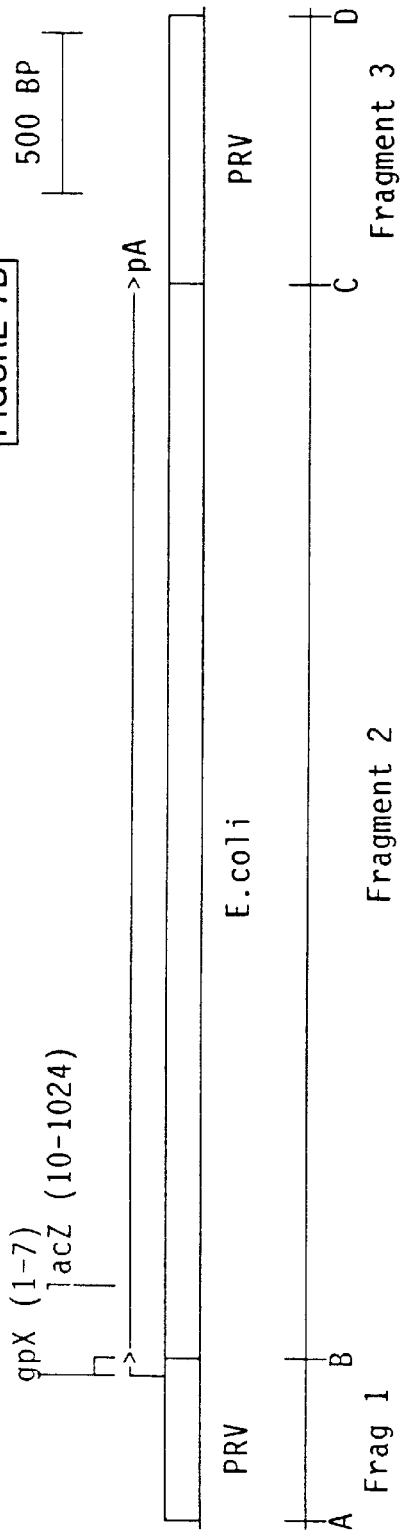
Figure 7B:
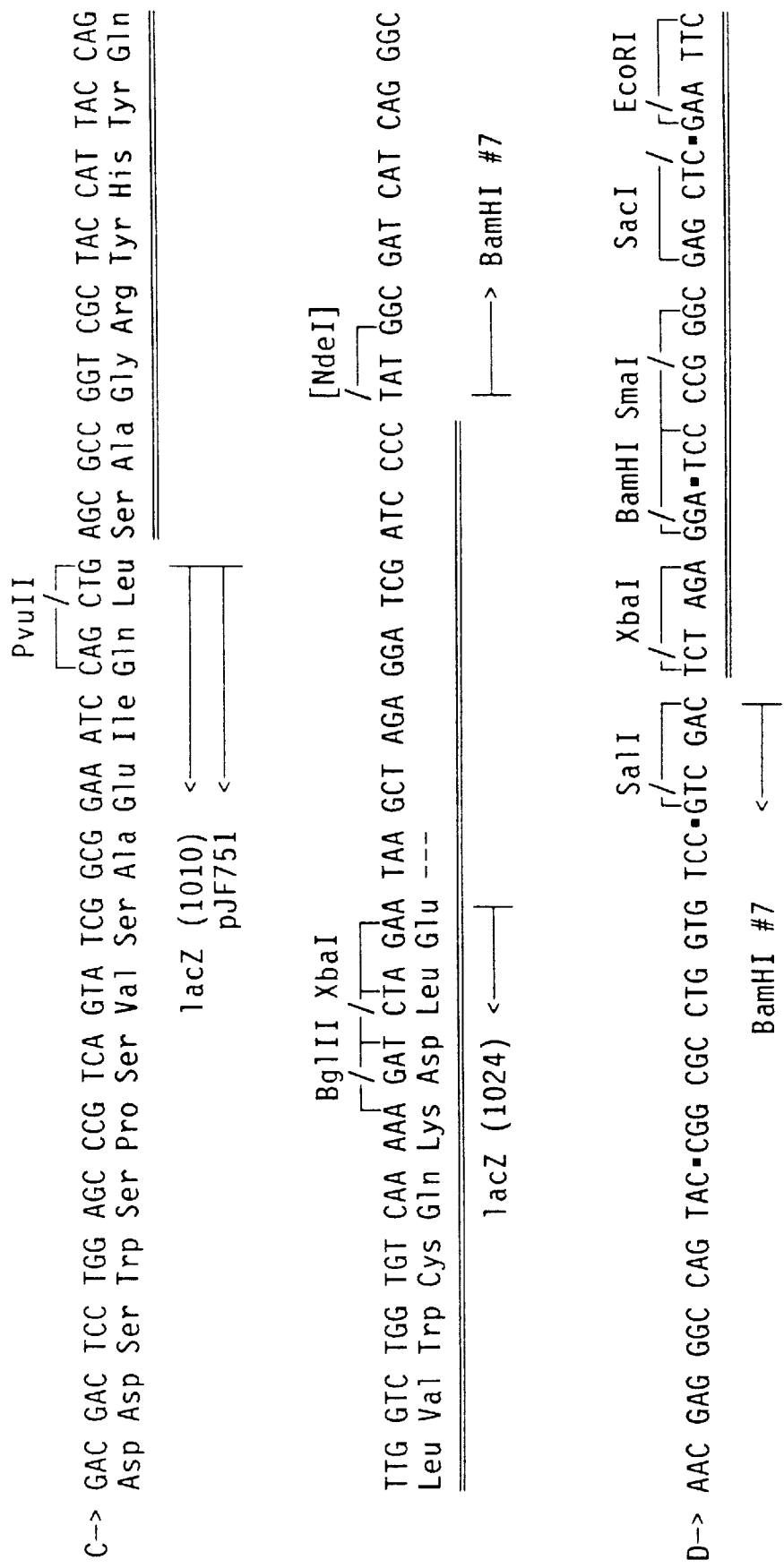

CONSTRUCTION OF HOMOLOGY VECTOR FOR INSERTION OF THE BETA-GALACTOSIDASE GENE INTO HVT US2 GENE. The beta-galactosidase (lacz) gene was inserted into the HVT EcoRI # 7 fragment at the unique StuI site. The marker gene is oriented in the same direction as the US2 gene. A detailed description of the marker gene is given in FIG. 7. It is constructed utilizing standard recombinant DNA techniques (Maniatis et al, 1982 and Sambrook et al, 1989), by joining restriction fragments from the following sources with the synthetic DNA sequences indicated in FIG. 7. Fragment 1 is an approximately 413 base pair SalI to BamHI restriction sub-fragment of the PRV BamHI restriction fragment 10 (Lomniczi et al., 1984). Fragment 2 is an approximately 3010 base pair BamHI to PvuII restriction fragment of plasmid pJF751 (Ferrari et al., 1985). Fragment 3 is an approximately 754 base pair NdeI to SalI restriction sub-fragment of the PRV BamHI restriction fragment #7 (Lomniczi et al., 1984).

SUBGENOMIC CLONE 172-07.BA2. Plasmid 172-07.BA2 was constructed for the purpose of generating recombinant HVT. It contains an approximately 25,000 base pair region of genomic HVT DNA. It may be used in conjunction with other subgenomic clones according to the PROCEDURE FOR GENERATING RECOMBINANT HERPESVIRUS FROM OVERLAPPING SUBGENOMIC FRAGMENTS for the construction of recombinant HVT. This plasmid may be constructed utilizing standard recombinant DNA techniques (Maniatis et al, 1982 and Sambrook et al, 1989), by joining two restriction fragments from the following sources. The first fragment is an approximately 2999 base pair BamHI to BamHI restriction fragment of pSP64 (Promega). The second fragment is the approximately 25,000 base pair BamHI #2 fragment of HVT (Buckmaster et al., 1988).

HOMOLOGY VECTOR 172-29.31. The plasmid 172-29.31 was constructed for the purpose of inserting foreign DNA into HVT. It contains a unique XhoI restriction enzyme site into which foreign DNA may be inserted. When a plasmid containing a foreign DNA insert at the XhoI site is used according to the DNA COTRANSFECTION FOR GENERATING RECOMBINANT HERPESVIRUSES or the PROCEDURE FOR GENERATING RECOMBINANT HERPESVIRUS FROM OVERLAPPING SUBGENOMIC FRAGMENTS a virus containing the foreign DNA will result. This plasmid may be constructed utilizing standard recombinant DNA techniques (Maniatis et al, 1982 and Sambrook et al, 1989), by joining two restriction fragments from the following sources. The first fragment is an approximately 2999 base pair BamHI to BamHI restriction fragment of pSP64 (Promega). The second fragment is the approximately 3300 base pair BamHI #16 fragment of HVT (Buckmaster et al., 1988). The complete sequence of the BamHI #16 fragment is given in SEQ ID NO:3. Note that the fragment was cloned such that the UL43 ORF is in the opposite transcriptional orientation to the pSP64 β-lacatamase gene.

HOMOLOGY VECTOR 172-63.1. The plasmid 172-63.1 was constructed for the purpose of inserting foreign DNA into HVT. It contains a unique XhoI restriction enzyme site into which foreign DNA may be inserted. When a plasmid containing a foreign DNA insert at the XhoI site is used according to the DNA COTRANSFECTION FOR GENERATING RECOMBINANT HERPESVIRUSES or the PROCEDURE FOR GENERATING RECOMBINANT HERPESVIRUS FROM OVERLAPPING SUBGENOMIC FRAGMENTS a virus containing the foreign DNA will result. This plasmid may be constructed utilizing standard recombinant DNA techniques (Maniatis et al, 1982 and Sambrook et al, 1989), by joining two restriction fragments from the following sources. The first fragment is an approximately 2999 base pair EcoRI to EcoRI restriction fragment of pSP64 (Promega). The second fragment is the approximately 5500 base pair EcoRI #9 fragment of HVT. Note that the EcoRI fragment was cloned such that the unique XhoI site is closest to the unique HindIII site in the pSP64 vector.

HOMOLOGY VECTORS 255-18.B16. The plasmid 255-18.B16 was constructed for the purpose of inserting the NDV HN and F genes into HVT. The NDV HN and F genes were inserted as a SalI fragment into the homology vector 172-29.31 at the XhoI site. The NDV HN and F genes were inserted in the same transcriptional orientation the UL43 ORF in the parental homology vector. A detailed description of the SalI fragment is shown in FIG. 12. The inserted SalI fragment may be constructed utilizing standard recombinant DNA techniques (Maniatis et al, 1982 and Sambrook et al, 1989), by joining restriction fragments from the following sources with the synthetic DNA sequences indicated in FIG. 12. Fragment 1 is an approximately 416 base pair SalI to BamHI restriction sub-fragment of the PRV BamHI restriction fragment 10 (Lomniczi et al., 1984). Fragment 2 is an approximately 3009 base pair BamHI to PvuII fragment of the plasmid pJF751 (Ferrari et al., 1985). Fragment 3 is an approximately 1200 base pair AvaII to EcoRI restriction fragment of full length NDV HN cDNA. Fragment 4 is an approximately 179 base pair EcoRI to PvuII restriction fragment of the plasmid pSP64 (Promega). Fragment 5 is an approximately 357 base pair SmaI to BamHI restriction sub-fragment of the HSV-l BamHI restriction fragment N. Fragment 6 is an approximately 1812 base pair BamHI to PstI restriction fragment of the full length NDV F cDNA. Fragment 7 is an approximately 235 base pair PstI to ScaI restriction fragment of the plasmid pBR322.

SUBGEMOMIC CLONE 378-50.BA1. Cosmid 378-50.BA1 was constructed for the purpose of generating recombinant HVT. It contains an approximately 29,500 base pair region of genomic HVT DNA. It may be used in conjunction with other subgenomic clones according to the PROCEDURE FOR GENERATING RECOMBINANT HERPESVIRUS FROM OVERLAPPING SUBGENOMIC FRAGMENTS for the construction of recombinant HVT. This cosmid may be constructed by joining two restriction fragments from the following sources. The first fragment is an approximately 8164 base pair BamHI to BamHI restriction fragment of pWE15 (Stratagene). The second fragment is the approximately 29,500 base pair BamHI #1 fragment of HVT (Buckmaster et al., 1988).

Figure 8:
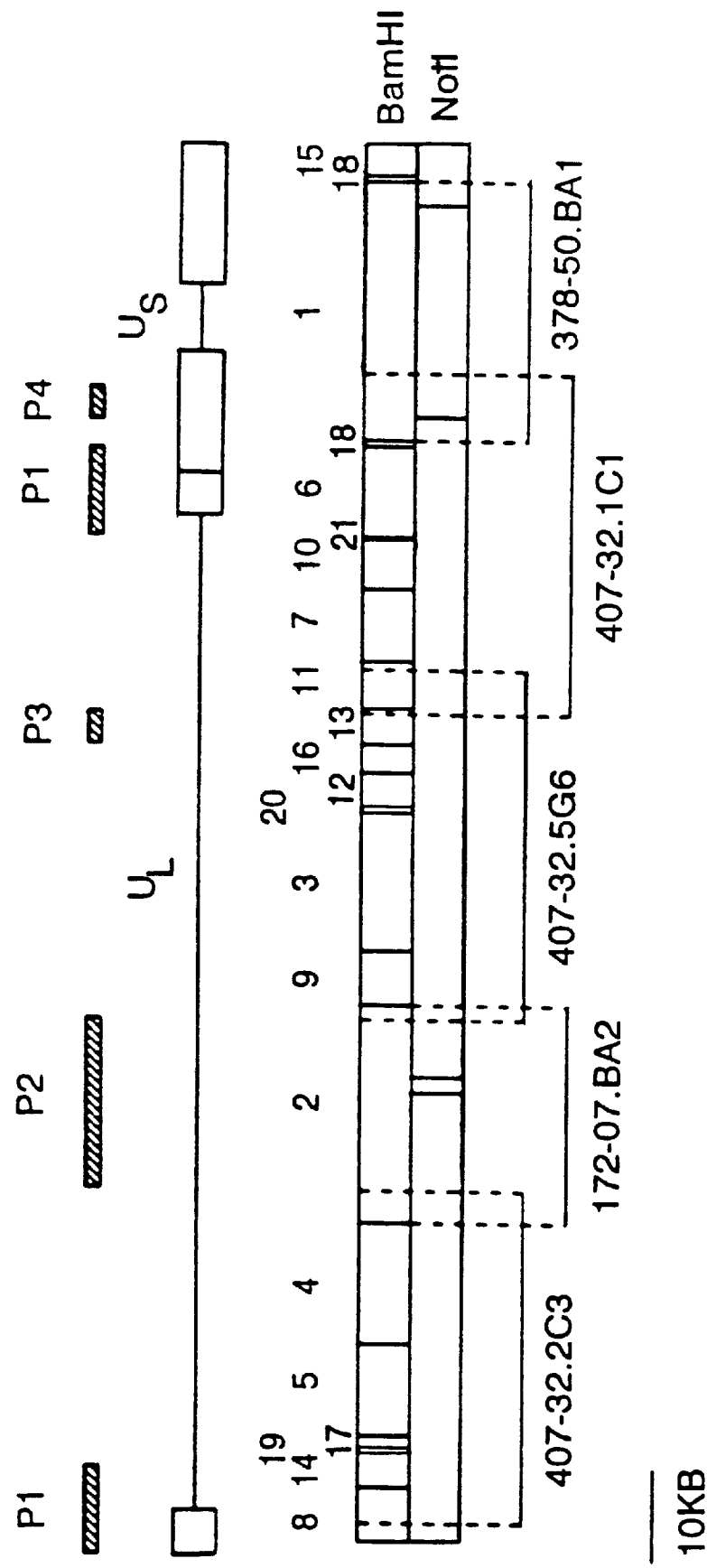
Figure 9:
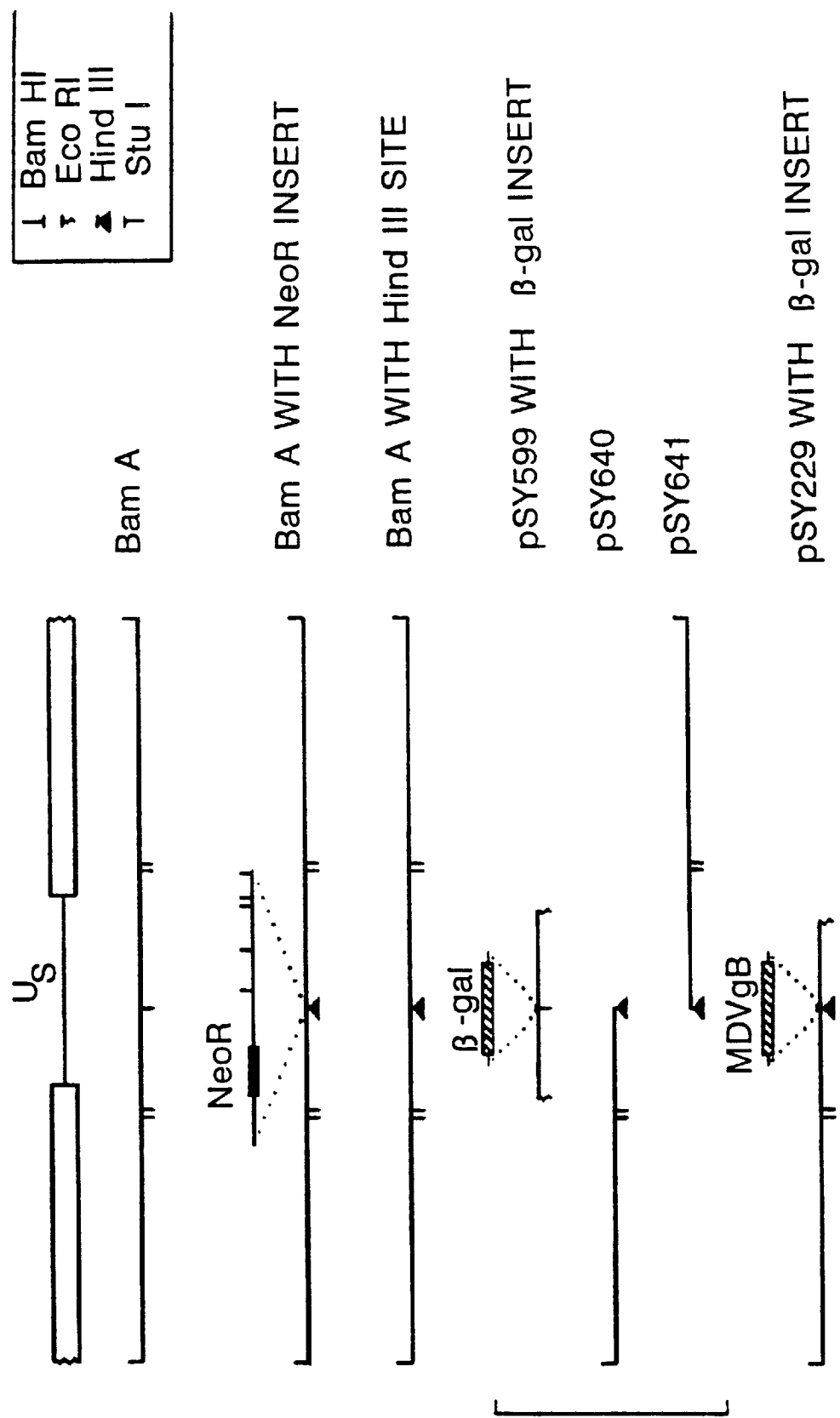

SUBGEMOMIC CLONE 407-32.1C1. Cosmid 407-32.1C1 was constructed for the purpose of generating recombinant HVT. It contains an approximately 38,850 base pair region of genomic HVT DNA (see FIG. 8). This region includes BamHI fragments 11, 7, 8, 21, 6, 18, approximately 1250 base pairs of fragment 13, and approximately 6,700 base pairs of fragment 1. It may be used in conjunction with other subgenomic clones according to the PROCEDURE FOR GENERATING RECOMBINANT HERPESVIRUS FROM OVERLAPPING SUBGENOMIC FRAGMENTS for the construction of recombinant HVT. This cosmid maybe constructed as described above in the PROCEDURE FOR GENERATING RECOMBINANT HERPESVIRUS FROM OVERLAPPING SUBGENOMIC FRAGMENTS. It was isolated from the sheared DNA library by screening with the probes P1 and P4 (described in FIG. 8). A bacterial strain containing this cosmid has been deposited pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A.

SUBGEMOMIC CLONE 407-32.2C3. Cosmid 407-32.2C3 was constructed for the purpose of generating recombinant HVT. It contains an approximately 40,170 base pair region of genomic HVT DNA (see FIG. 8). This region includes BamHI fragments 10, 14, 19, 17, 5, and approximately 2,100 base pairs of fragment 2. It may be used in conjunction with other subgenomic clones according to the PROCEDURE FOR GENERATING RECOMBINANT HERPESVIRUS FROM OVERLAPPING SUBGENOMIC FRAGMENTS for the construction of recombinant HVT. This cosmid may be constructed as described above in the PROCEDURE FOR GENERATING RECOMBINANT HERPESVIRUS FROM OVERLAPPING SUBGENOMIC FRAGMENTS. It was isolated from the sheared DNA library by screening with the probes P1 and P2 (described in FIG. 8). A bacterial strain containing this cosmid has been deposited pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A.

SUBGEMOMIC CLONE 407-32.5G6. Cosmid 407-32.5G6 was constructed for the purpose of generating recombinant HVT. It contains an approximately 40,000 base pair region of genomic HVT DNA (see FIG. 8). This region includes BamHI fragments 9, 3, 20, 12, 16, 13, approximately 1,650 base pairs of fragment 2, and approximately 4,000 base pairs of fragment 11. It may be used in conjunction with other subgenomic clones according to the PROCEDURE FOR GENERATING RECOMBINANT HERPESVIRUS FROM OVERLAPPING SUBGENOMIC FRAGMENTS for the construction of recombinant HVT. This cosmid may be constructed as described above in the PROCEDURE FOR GENERATING RECOMBINANT HERPESVIRUS FROM OVERLAPPING SUBGENOMIC FRAGMENTS. It was isolated from the sheared DNA library by screening with the probes P2 and P3 (described in FIG. 8). A bacterial strain containing this cosmid has been deposited pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A.

HOMOLOGY VECTOR 435-47.1. The plasmid 435-47.1 was constructed for the purpose of inserting foreign DNA into HVT. It contains a unique HindIII restriction enzyme site into which foreign DNA may be inserted. When a plasmid containing a foreign DNA insert at the HindIII site is used according to the DNA COTRANSFECTION FOR GENERATING RECOMBINANT HERPESVIRUSES or the PROCEDURE FOR GENERATING RECOMBINANT HERPESVIRUS FROM OVERLAPPING SUBGENOMIC FRAGMENTS a virus containing the foreign DNA will result. This plasmid may be constructed utilizing standard recombinant DNA techniques (Maniatis et al, 1982 and Sambrook et al, 1989), by joining two restriction fragments from the following sources. The first fragment is an approximately 2999 base pair EcoRI to EcoRI restriction fragment of pSP64 (Promega). The second fragment is the approximately 7300 base pair EcoRI #7 fragment of HVT. Note that the HindIII site of the pSP64 vector was removed by digesting the subclone with HindIII followed by a Klenow fill in reaction and religation. A synthetic HindIII linker (CAAGCTTG) was then inserted into the unique StuI site of the EcoRI #7 fragment.

SUBGEMOMIC CLONE 437-26.24. Plasmid 437-26.24 was constructed for the purpose of generating recombinant HVT. It contains an approximately 13,600 base pair region of genomic HVT DNA. It may be used in conjunction with other subgenomic clones according to the PROCEDURE FOR GENERATING RECOMBINANT HERPESVIRUS FROM OVERLAPPING SUBGENOMIC FRAGMENTS for the construction of recombinant HVT. This plasmid may be constructed utilizing standard recombinant DNA techniques (Maniatis et al, 1982 and Sambrook et al, 1989), by joining two restriction fragments from the following sources. The first fragment is an approximately 2970 base pair HindIII to BamHI restriction fragment of pSP64 (Promega). The second fragment is the approximately 13,600 base pair BamHI to StuI sub-fragment of the BamHI #2 fragment of HVT (Buckmaster et al., 1988). Note that the BamHI #2 fragment contains five StuI sites, the site utilized in this subcloning was converted to a HindIII site as described in the PROCEDURE FOR GENERATING RECOMBINANT HERPESVIRUS FROM OVERLAPPING SUBGENOMIC FRAGMENTS.

SUBGEMOMIC CLONE 437-26.26. Plasmid 437-26.26 was constructed for the purpose of generating recombinant HVT. It contains an approximately 15,300 base pair region of genomic HVT DNA. It may be used in conjunction with other subgenomic clones according to the PROCEDURE FOR GENERATING RECOMBINANT HERPESVIRUS FROM OVERLAPPING SUBGENOMIC FRAGMENTS for the construction of recombinant HVT. This plasmid may be constructed utilizing standard recombinant DNA techniques (Maniatis et al, 1982 and Sambrook et al, 1989), by joining two restriction fragments from the following sources. The first fragment is an approximately 2970 base pair HindIII to BamHI restriction fragment of pSP64 (Promega). The second fragment is the approximately 15,300 base pair BamHI to StuI sub-fragment of the BamHI #2 fragment of HVT (Buckmaster et al., 1988). Note that the BamHI #2 fragment contains five StuI sites, the site utilized in this subcloning was converted to a HindIII site as described in the PROCEDURE FOR GENERATING RECOMBINANT HERPESVIRUS FROM OVERLAPPING SUBGENOMIC FRAGMENTS.

Figure 10B:
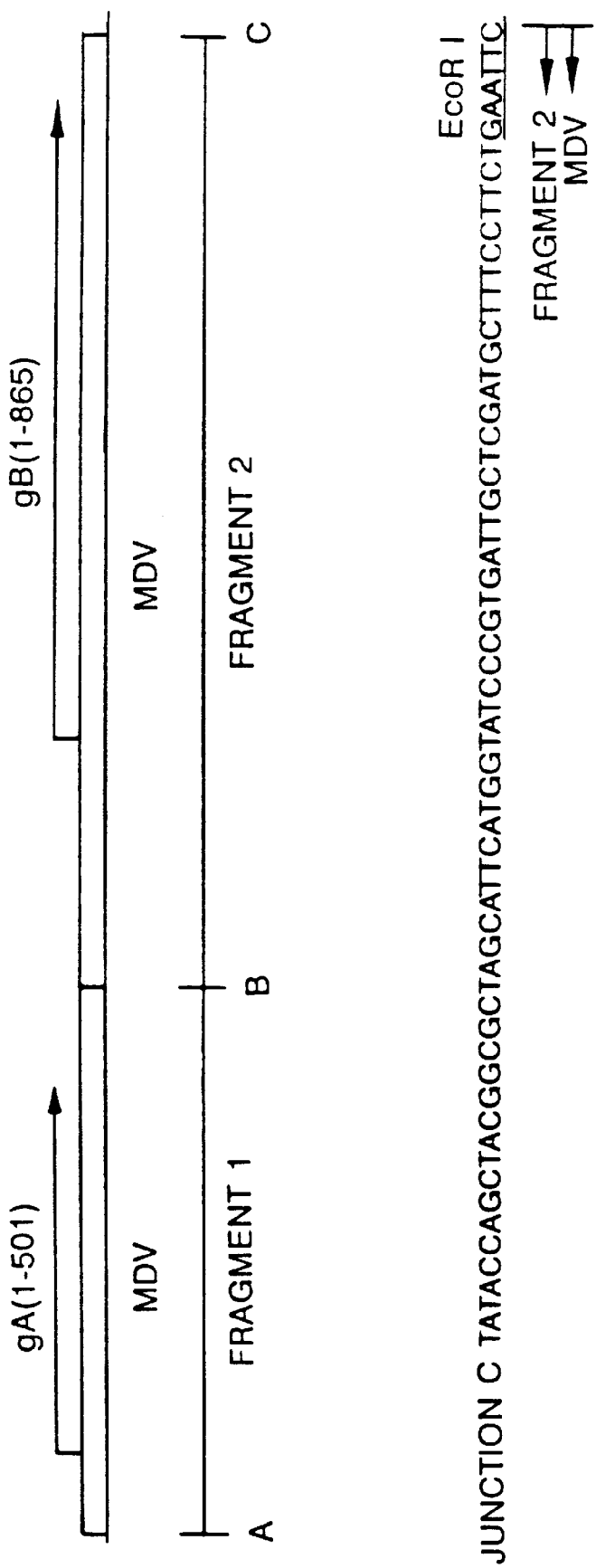
Figure 11A:
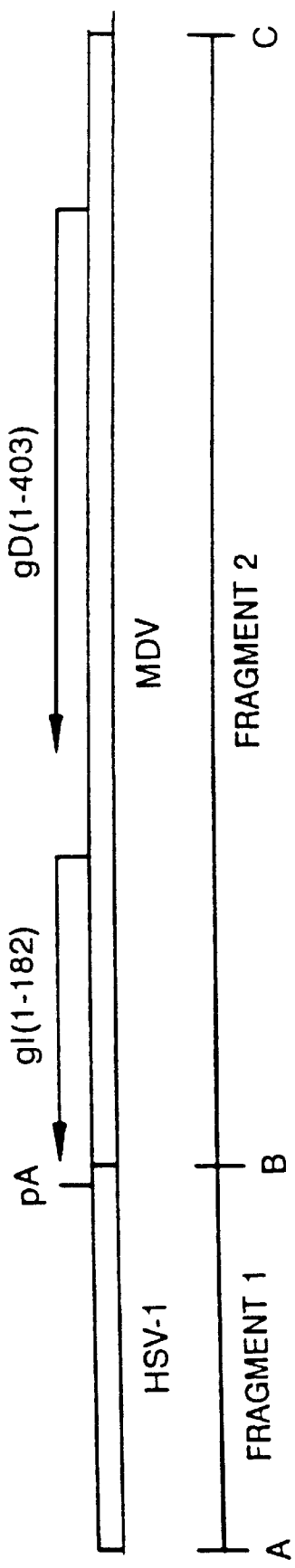
Figure 11B:
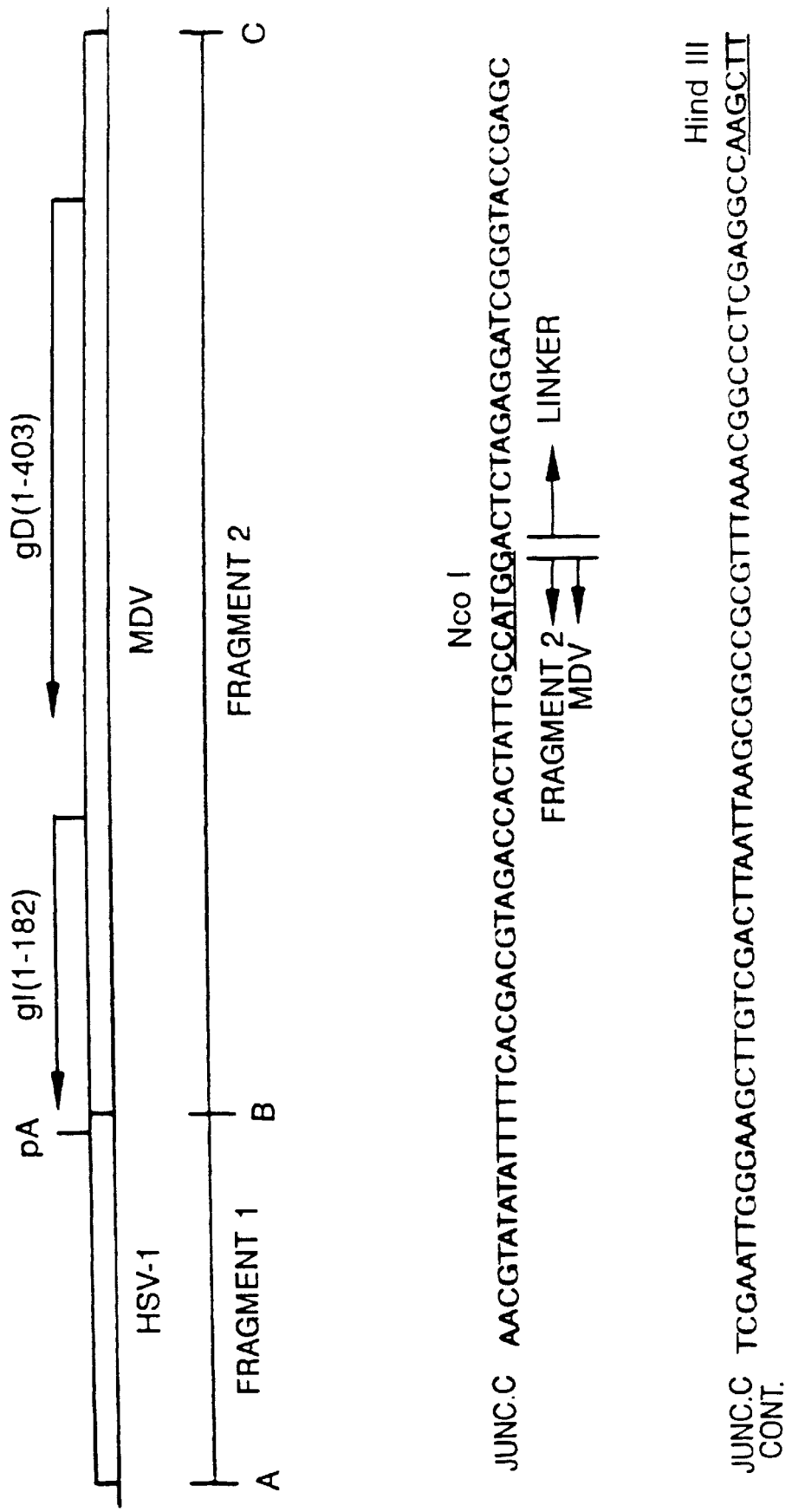

HOMOLOGY VECTORS 456-18.18 and 456-17.22. The plasmids 456-18.18 and 456-17.22 were constructed for the purpose of inserting the MDV gA and gB genes into HVT. The MDV genes were inserted as a cassette into the homology vector 435-47.1 at the unique HindIII site. The MDV genes were inserted at the blunt ended HindIII site as a blunt ended PstI to EcoRI fragment (see FIG. 10). The HindIII and EcoRI sites were blunted by the Klenow fill in reaction. The PstI site was blunted by the T4 DNA polymerase reaction. Note that the MDV cassette was inserted in both orientations. Plasmid 456-18.18 contains the MDV genes inserted in the opposite transcriptional orientation to the US2 gene in the parental homology vector. Plasmid 456-17.22 contains the MDV genes inserted in the same transcriptional orientation as the US2 gene in the parental homology vector. A detailed description of the MDV cassette is given in FIG. 10. It may be constructed utilizing standard recombinant DNA techniques (Maniatis et al, 1982 and Sambrook et al, 1989), by joining restriction fragments from the following sources with the synthetic DNA sequences indicated in FIG. 10. Fragment 1 is an approximately 2178 base pair PvuII to EcoRV restriction sub-fragment of the MDV EcoRI 6.9 KB genomic restriction fragment (Ihara et al., 1989). Fragment 2 is an approximately 3898 base pair SalI to EcoRI genomic MDV fragment (Ross, et al., 1989).

HOMOLOGY VECTOR 528-03.37. The plasmid 528-03.37 was constructed for the purpose of inserting the infectious laryngotracheitis (ILT) virus gD gene into HVT. The gD gene followed by the PRV gX poly adenylation signal was inserted as a cassette into the homology vector 435-47.1 at the unique HindIII site. The cassette may be constructed utilizing standard recombinant DNA techniques (Maniatis et al, 1982 and Sambrook et al, 1989), by joining restriction fragments from the following sources. The first fragment is an approximately 2060 base pair EcoRI to BclI restriction sub-fragment of the ILT KpnI genomic restriction fragment #8 (10.6 KB). The second fragment is an approximately 754 base pair NdeI to SalI restriction sub-fragment of the PRV BamHI restriction fragment #7 (Lomniczi et al., 1984). Note that the fragments are oriented such that BclI and NdeI sites are contiguous.

HOMOLOGY VECTOR 528-11.43. The plasmid 528-11.43 was constructed for the purpose of inserting the infectious laryngotracheitis (ILT) virus gB gene (A. M. Grifin, 1991) into HVT. The gB gene was inserted as an EcoRI fragment into the homology vector 435-47.1 at the unique HindIII site. The gB gene was inserted at the blunt ended HindIII site as a blunt ended EcoRI fragment. The HindIII and EcoRI sites were blunted by the Klenow fill in reaction. The gB gene was inserted in the same transcriptional orientation as the US2 gene in the parental homology vector. The EcoRI fragment may be obtained as a 3.0 KB ILT virus genomic fragment.

HOMOLOGY VECTOR 518-46.B3. The plasmid 518-46.B3 was constructed for the purpose of inserting foreign DNA into HVT. It contains a unique HindIII restriction enzyme site into which foreign DNA may be inserted. When a plasmid containing a foreign DNA insert at the HindIII site is used according to the DNA COTRANSFECTION FOR GENERATING RECOMBINANT HERPESVIRUSES or the PROCEDURE FOR GENERATING RECOMBINANT HERPESVIRUS FROM OVERLAPPING SUBGENOMIC FRAGMENTS a virus containing the foreign DNA will result. This plasmid may be constructed utilizing standard recombinant DNA techniques (Maniatis et al, 1982 and Sambrook et al, 1989), by joining three restriction fragments from the following sources. The first fragment is an approximately 1649 base pair PvuI to SalI restriction fragment of pSP64 (Promega). The second fragment is an approximately 1368 base pair PvuI to SalI restriction fragment of pSP65 (Promega). The third fragment is the approximately 3400 base pair XhoI to XhoI fragment of plasmid 437-47.1.

HOMOLOGY VECTOR 535-70.3. The plasmid 535-70.3 was constructed for the purpose of inserting the MDV gB, and gA genes and the NDV F gene into HVT. The F gene was inserted as a cassette into homology vector 456-17.22 at the HindIII site located between the MDV gA and gB genes (see FIG. 10A junction B). The F gene is under the control of the HCMV immediate early promoter and followed by the HSV-1 TK poly adenylation signal. The F gene was inserted in the same transcriptional orientation as the US2 gene in the parental homology vector. The cassette may be constructed utilizing standard recombinant DNA techniques (Maniatis et al, 1982 and Sambrook et al, 1989), by joining restriction fragments from the following sources. The first fragment is an approximately 1191 base pair PstI to AvaII restriction sub-fragment of the HCMV genomic XbaI E fragment (D. R. Thomsen, et al., 1981). The second fragment is an approximately 1812 base pair BamHI to PstI restriction fragment of the full length NDV F cDNA clone (B1 strain). The last fragment is an approximately 784 base pair SmaI to SmaI restriction sub-fragment of the HSV-1 BamHI restriction fragment Q (McGeoch, et al., 1985).

HOMOLOGY VECTOR 549-24.15. The plasmid 549-24.15 was constructed for the purpose of inserting the MDV gB, and gA genes and the NDV HN and F genes into HVT. The HN and F genes were inserted as a cassette into homology vector 456-17.22 at the HindIII site located between the MDV gA and gB genes (see FIG. 10A junction B). The HN and F genes are under the control of the PRV gpX and HCMV immediate early promoters respectively. The HN and F genes are followed by the PRV gX poly and HSV-1 TK adenylation signals respectively. The cassette may be constructed utilizing standard recombinant DNA techniques (Maniatis et al, 1982 and Sambrook et al, 1989), by joining restriction fragments from the following sources. The first fragment is an approximately 413 base pair SalI to BamHI restriction sub-fragment of the PRV BamHI fragment #10 (Lomniczi, et al., 1984). The second fragment is an approximately 1811 base pair AvaII to NaeI restriction fragment of the full length NDV HN cDNA clone (B1 strain). The third fragment is an approximately 754 base pair NdeI to SalI restriction sub-fragment of the PRV BamHI restriction fragment #7 (Lomniczi, et al., 1984). The fourth fragment is an approximately 1191 base pair PstI to AvaII restriction sub-fragment of the HCMV genomic XbaI E fragment (D. R. Thomsen, et al., 1981). The fifth fragment is an approximately 1812 base pair BamHI to PstI restriction fragment of the full length NDV F cDNA clone (B1 strain). The last fragment is an approximately 784 base pair SmaI to SmaI restriction sub-fragment of the HSV-1 BamHI restriction fragment Q (McGeoch, et al., 1985).

HOMOLOGY VECTOR 549-62.10. The plasmid 549-62.10 was constructed for the purpose of inserting the MDV gB, and gA genes and the NDV HN gene into HVT. The HN gene was inserted as a cassette into homology vector 456-17.22 at the HindIII site located between the MDV gA and gB genes (see FIG. 10A junction B). The HN gene is under the control of the PRV gpX promoter and followed by the PRV gX poly adenylation signal. The HN gene was inserted in the same transcriptional orientation as the US2 gene in the parental homology vector. The cassette may be constructed utilizing standard recombinant DNA techniques (Maniatis et al, 1982 and Sambrook et al, 1989), by joining restriction fragments from the following sources. The first fragment is an approximately 413 base pair SalI to BamHI restriction sub-fragment of the PRV BamHI fragment #10 (Lomniczi, et al., 1984). The second fragment is an approximately 1811 base pair AvaII to NaeI restriction fragment of the full length NDV HN CDNA clone (B1 strain). The last fragment is an approximately 754 base pair NdeI to SalI restriction sub-fragment of the PRV BamHI restriction fragment #7 (Lomniczi, et al., 1984).

SUBGENOMIC CLONE 550-60.6 Plasmid 550-60.6 was constructed for the purpose of generating recombinant HVT. It contains an approximately 12,300 base pair region of genomic HVT DNA. It may be used in conjunction with other subgenomic clones according to the PROCEDURE FOR GENERATING RECOMBINANT HERPESVIRUS FROM OVERLAPPING SUBGENOMIC FRAGMENTS for the construction of recombinant HVT. This plasmid may be constructed utilizing standard recombinant DNA techniques (Maniatis et al, 1982 and Sambrook et al, 1989), by joining two restriction fragments from the following sources. The first fragment is an approximately 4176 base pair EcoRV to BamHI restriction fragment of pBR322. The second fragment is the approximately 12,300 base pair sub-fragment of the BamHI #2 fragment of HVT (Buckmaster et al., 1988). This fragment was generated in the following manner. Plasmid 437-26.26 was linearized with HindIII and then resected with the ExoIII Mung Bean Deletion Kit (Stratagene). Samples from the 3 and 4 minute reactions were combined and digested with BamHI resulting in a population of fragments containing the desired 12,300 base pair sub-fragment. This population was cloned into the pBR322 fragment and the resulting clones were screened for the appropriate size and restriction map. Fortuitously the resected sub-fragment that generated clone 550-60.6 ended in the nucleotides GG which generated a second BamHI site when ligated to the EcoRV site (ATCC) of pBR322. A bacterial strain containing this plasmid has been deposited pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A.

HOMOLOGY VECTORS 566-41.5. The plasmid 566-41.5 was constructed for the purpose of inserting the MDV gA, gB and gD genes into HVT. The MDV gD gene was inserted as a HindIII fragment into the homology vector 456-17.22 at the HindIII site located between MDV gA and gB (see FIG. 10). The MDV gene was inserted in the same transcriptional orientation as gA and gB in the parental homology vector. A detailed description of the HindIII fragment containing the MDV gD gene is shown in FIG. 11. Note that a herpesvirus polyadenation signal was added to the gD gene cassette. The inserted HindIII fragment may be constructed utilizing standard recombinant DNA techniques (Maniatis et al, 1982 and Sambrook et al, 1989), by joining restriction fragments from the following sources with the synthetic DNA sequences indicated in FIG. 11. Fragment 1 is an approximately 784 base pair SmaI to SmaI restriction sub-fragment of the HSV-1 BamHI restriction fragment Q (McGeoch et al., 1988). Note that this fragment is oriented such that the polyadenylation sequence (AATAAA) is located closest to junction B. Fragment 2 is an approximately 2177 base pair SalI to NcoI sub-fragment of the MDV BglII 4.2 KB genomic restriction fragment (Ross, et al., 1991).

HOMOLOGY VECTOR 567-72.1D. The plasmid 567-72.1D was constructed for the purpose of inserting the MDV gB, gA, and gD genes and the infectious bronchitis virus (IBV) matrix and spike genes into HVT. The IBV genes were inserted as a cassette into homology vector 566-41.5 at the unique NotI site located upstream of the MDV gD gene (see FIG. 11B junction C). The IBV spike and matrix genes are under the control of the HCMV immediate early and PRV gpX promoters respectively. The IBV spike and matrix genes are followed by the HSV-1 TK and PRV gX poly adenylation signals respectively. The IBV genes were inserted in the same transcriptional orientation as the US2 gene in the parental homology vector. The cassette may be constructed utilizing standard recombinant DNA techniques (Maniatis et al, 1982 and Sambrook et al, 1989), by joining restriction fragments from the following sources. The first fragment is an approximately 413 base pair SalI to BamHI restriction sub-fragment of the PRV BamHI fragment #10 (Lomniczi, et al., 1984). The second fragment contains amino acids 1 to 223 of the IBV matrix gene. The coding region was obtained from a cDNA clone of the Arkansas strain of IBV. The third fragment is an approximately 754 base pair NdeI to SalI restriction sub-fragment of the PRV BamHI restriction fragment #7 (Lomniczi, et al., 1984). The fourth fragment is an approximately 1191 base pair PstI to AvaII restriction sub-fragment of the HCMV genomic XbaI E fragment (D. R. Thomsen, et al., 1981). The fifth fragment contains amino acids 4 to 1162 of the IBV spike gene. The coding region was obtained from a cDNA clone of the Arkansas strain of IBV. The last fragment is an approximately 784 base pair SmaI to SmaI restriction sub-fragment of the HSV-1 BamHI restriction fragment Q (McGeoch, et al., 1985).

HOMOLOGY VECTOR 603-57.F1. The plasmid 603-57.F1 was constructed for the purpose of inserting the IBDV VP2 gene into HVT. The IBDV VP2 gene was inserted as a cassette into homology vector 435-47.1 at the unique HindIII site. The VP2 gene is under the control of the HCMV immediate early promoter and is followed by the HSV-1 TK poly adenylation signal. The VP2 gene was inserted in the same transcriptional orientation as the US2 in the parental homology vector. The cassette may be constructed utilizing standard recombinant DNA techniques (Maniatis et al, 1982 and Sambrook et al, 1989), by joining restriction fragments from the following sources. The first fragment is an approximately 1191 base pair PstI to AvaII restriction sub-fragment of the HCMV genomic XbaI E fragment (D. R. Thomsen, et al., 1981). The second fragment is an approximately 1081 base pair BclI to BamHI restriction sub-fragment of the full length IBDV cDNA clone (see SEQ ID NO:1). Note that the BclI site was introduced into the cDNA clone directly upstream of the VP2 initiator methionine by converting the sequence CGCAGC to TGATCA. The first and second fragments are oriented such that AvaII and BclI sites are contiguous. The third fragment is an approximately 784 base pair SmaI to SmaI restriction sub-fragment of the HSV-1 BamHI restriction fragment Q (McGeoch, et al., 1985).

HOMOLOGY VECTOR 633-13.27. The plasmid 633-13.27 was constructed for the purpose of inserting the MDV gB, gA and gD genes and the NDV HN and F genes into HVT. The HN and F genes are under the control of the PRV gpX and HCMV immediate early promoters respectively. The HN and F genes are followed by the PRV gX poly and HSV-1 TK adenylation signals respectively. All five genes were inserted in the same transcriptional orientation as the US2 gene in the parental homology vector. The genes were inserted in the following order MDV gA, NDV HN, NDV F, MDV gD, and MDV gB.

HOMOLOGY VECTOR 634-29.16. The plasmid 634-29.16 was constructed for the purpose of inserting the ILT virus gB and gD genes into HVT. The lacZ marker gene followed by the ILT gB and gD genes inserted as a cassette into the homology vector 172-29.31 at the unique XhoI site. The cassette may be constructed utilizing standard recombinant DNA techniques (Maniatis et al, 1982 and Sambrook et al, 1989), by joining restriction fragments from the following sources. The first fragment is an approximately 4229 base pair SalI to SalI restriction fragment derived from the lacZ marker gene described above and shown in FIG. 7. The second fragment is an approximately 2060 base pair EcoRI to BclI restriction sub-fragment of the ILT KpnI genomic restriction fragment #8 (10.6 KB). The third fragment is an approximately 754 base pair NdeI to SalI restriction sub-fragment of the PRV BamHI restriction fragment #7 (Lomniczi et al., 1984). Note that the second and third fragments are oriented such that BclI and NdeI sites are contiguous. The fourth fragment is the 3.0 KB ILT virus genomic EcoRI fragment containing the gB gene. All three genes are in the same transcriptional orientation as the UL43 gene.

EXAMPLES

Example 1

S-HVT-001

Figure 1A:
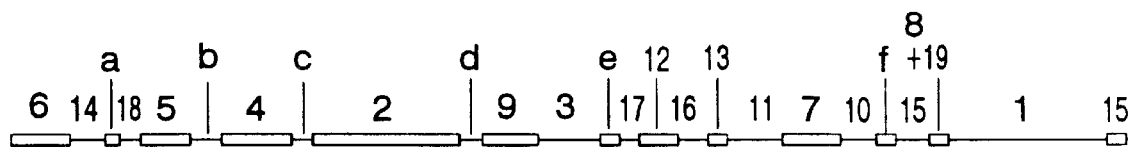
FIGS. 1A–1C

S-HVT-001 is a herpesvirus of turkeys (HVT) that contains the E. coli β-galactosidase gene inserted into the unique long region of the HVT genome. The restriction enzyme map of HVT has been published (T. Igarashi, et al., 1985). This information was used as a starting point to engineer the insertion of foreign genes into HVT. The BamHI restriction map of HVT is shown in FIG. 1A. From this data, several different regions of HVT DNA into which insertions of foreign genes could be made were targeted. The foreign gene chosen for insertion was the E. coli β-galactosidase (lacZ) gene, which we have used in PRV. The promoter was the PRV gpX promoter. The lacZ gene was inserted into the unique long region of HVT, specifically into the XhoI site in the BamHI #16 (3329 bp) fragment, and was shown to be expressed in an HVT recombinant by the formation of blue plaques using the substrate Bluogal™ (Bethesda Research Labs). Similarly, the lacZ gene has been inserted into the SalI site in the repeat region contained within the BamHI #19 (900 bp) fragment.

Figure 1B:
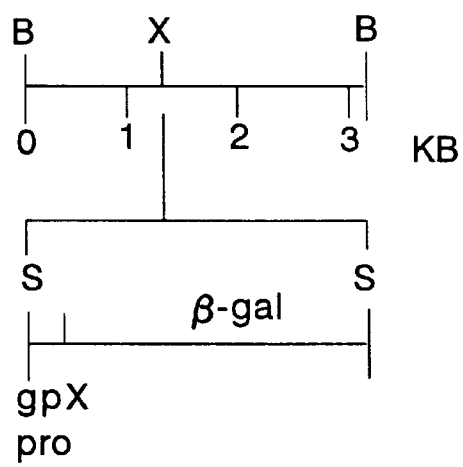
Figure 1C:
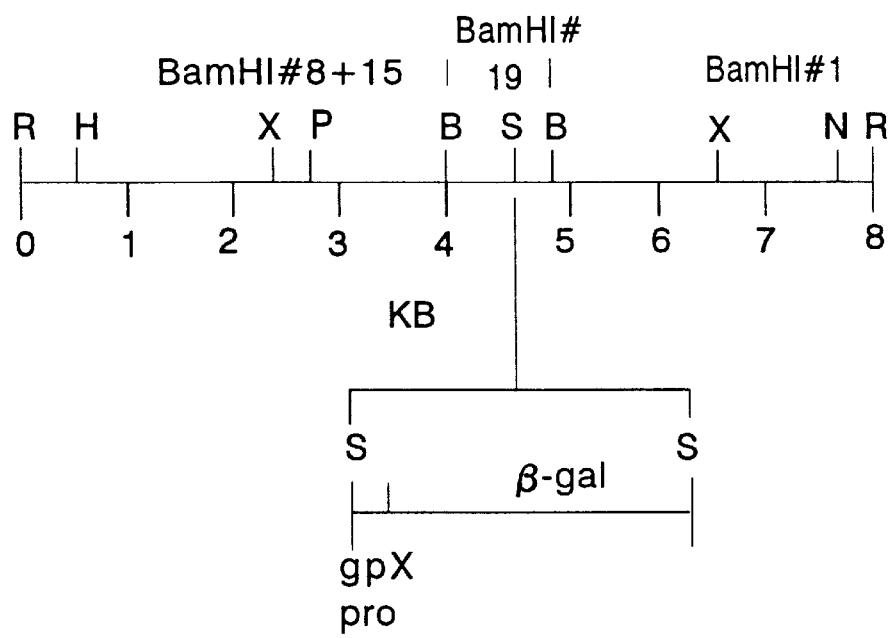
Figure 2B:
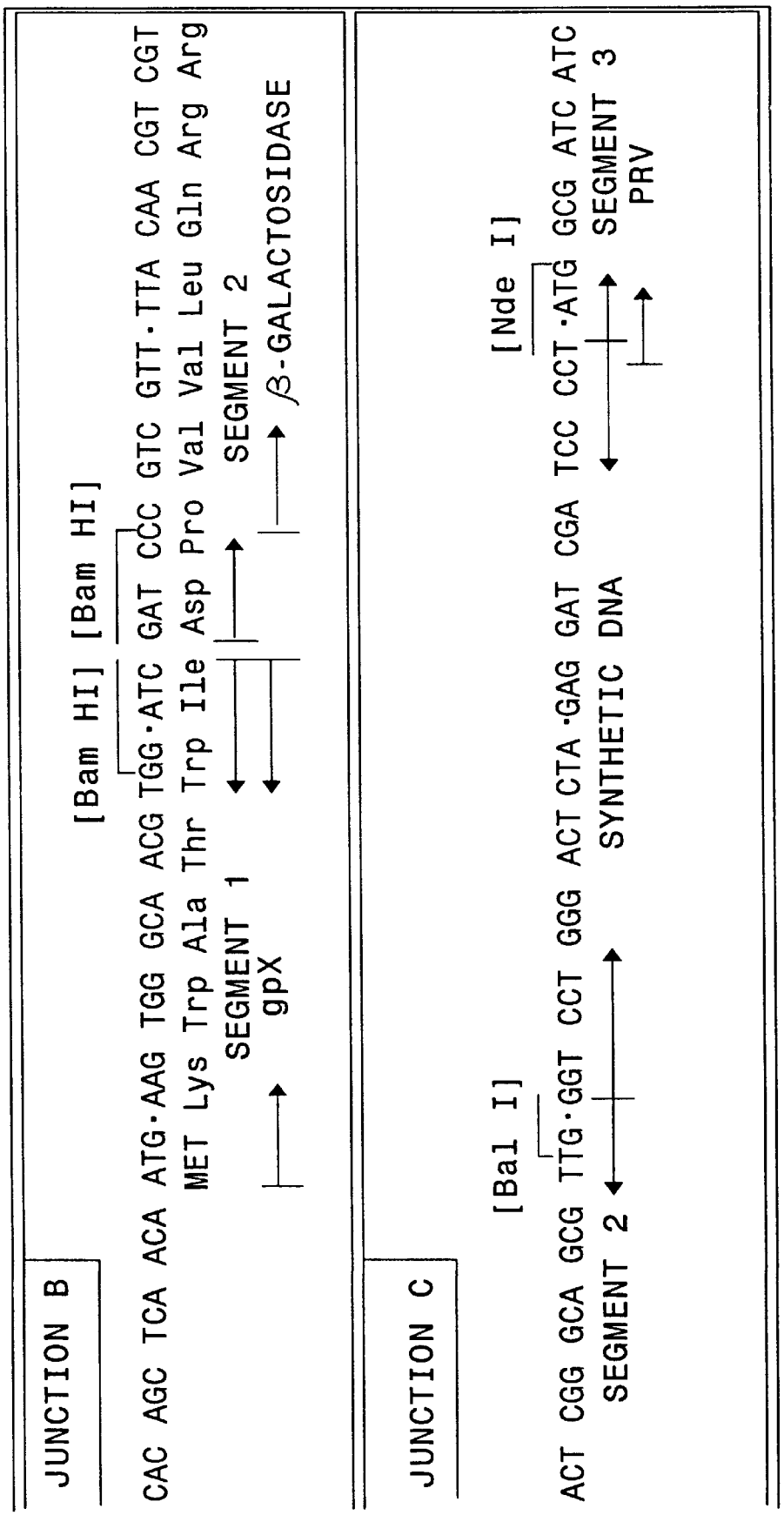
Figure 2D:
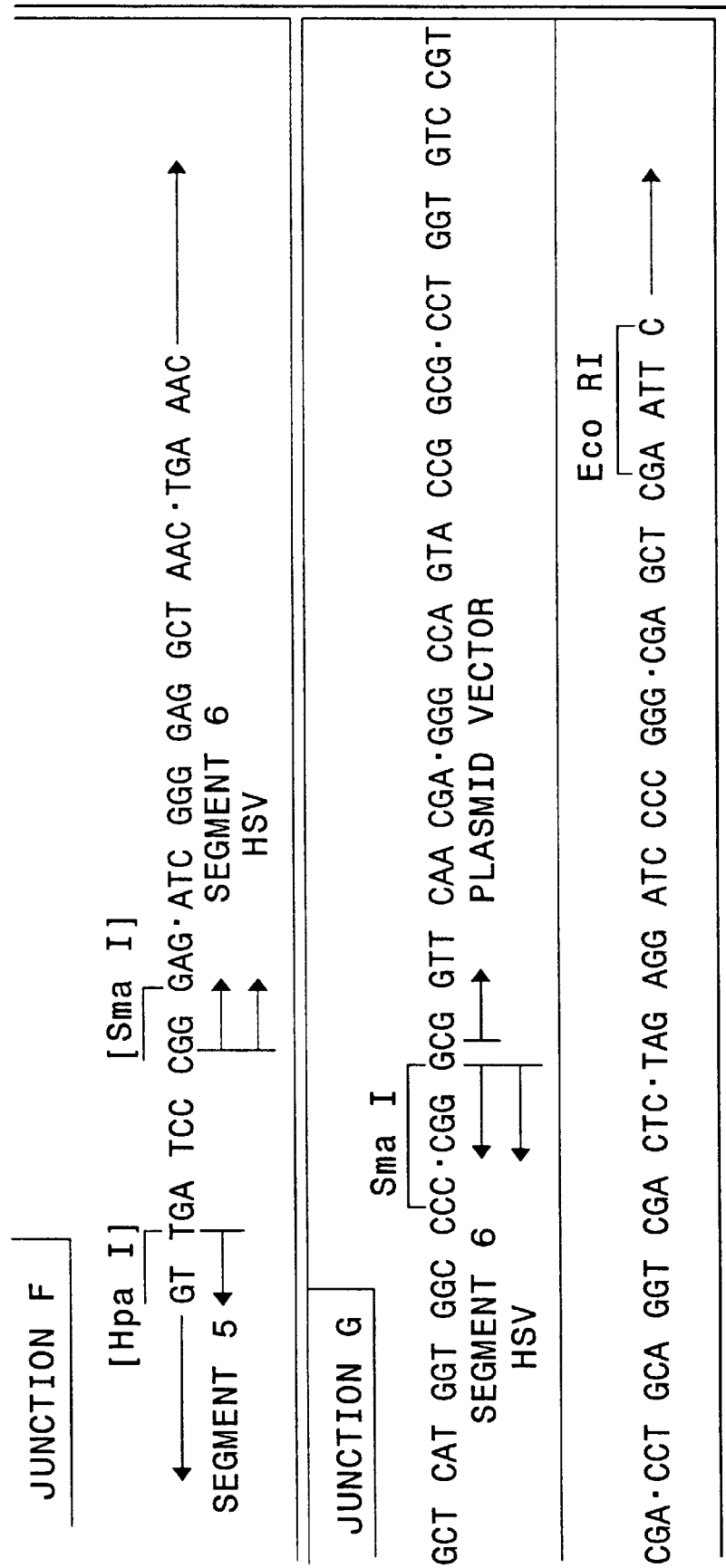

These experiments show that HVT is amenable to the procedures described within this application for the insertion and expression of foreign genes in herpesviruses. In particular, two sites for insertion of foreign DNA have been identified (FIGS. 1B and 1C).

Example 2

S-HVT-003

S-HVT-003 is a herpesvirus of turkeys (HVT) that contains the E. coli β-galactosidase (lacZ) gene and the infectious bursal disease virus (IBDV) strain S40747 large segment of RNA (as a cDNA copy) inserted into the unique long region of the HVT genome. This IBDV DNA contains one open reading frame that encodes three proteins (5'VP2-VP4-VP3 3'), two of which are antigens to provide protection against IBDV infections of chickens. Expression of the genes for both β-galactosidase and the IBDV polyprotein are under the control of the pseudorabies virus (PRV) gpX gene promoter. S-HVT-003, deposited under ATCC Accession No. VR 2178, was made by homologous recombination.

The IBDV genes were cloned by the cDNA CLONING PROCEDURE. Clones representing the genome of IBDV were screened by SOUTHERN BLOTTING OF DNA procedure against blots containing authentic IBDV RNA. Positive clones were then characterized by restriction mapping to identify groups of clones. Two such clones were identified, that together were found to represent the entire coding region of the IBDV large segment of RNA (3.3 kb dsRNA). One cDNA clone (2-84) contained an approximately 2500 base pair fragment representing the first half of the IBDV gene. The second clone (2-40) contained an approximately 2000 base pair fragment representing the distal half of the IBDV gene. Plasmid 2-84/2-40, representing the entire IBDV gene, was constructed by joining clone 2-84 and 2-40 at a unique PvuII site present in the overlapping sequences. The IBDV genome can be obtained from plasmid 2-84/2-40 as an approximately 3400 base pair SmaI to HpaI fragment. Confirmation of the nature of the proteins encoded by the IBDV gene was obtained by expressing the clone (2-84/2-40) in E. coli and detecting VP3 antigen using antiserum made against purified IBDV capsid proteins on Western blots. Applicants' sequence of the large DNA segment that encodes the IBDV antigens is given seq ID # 1. This sequence shows one open reading frame that will henceforth be referred to as the IBDV gene. The sequence of an Australian IBDV strain has been published which bears close homology to applicants' sequence (Hudson et al, 1986). Comparison of the amino acid differences between the two viruses revealed 29 amino acid changes within the 1012 amino acid coding region. There were only 3 amino acid differences deduced for VP4 and only 8 in VP3. In contrast, VP2 contained 18 amino acid changes, 14 of which were clustered between amino acids 139 to 332.

For insertion into the genome of HVT, the coding region for the IBDV gene was cloned between the PRV gpx promoter and the HSV TK poly-A signal sequence, creating plasmid 191-23. To aid in the identification of HVT recombinants made by homologous recombination containing the IBDV gene the gpX promoted IBDV fragment from plasmid 191-23 was inserted behind (in tandem to) a lacZ gene controlled by a gpX promoter. The resultant plasmid, 191-47, contains the E. coli lacZ gene and the IBDV gene under the control of individual PRV gpX promoters. In constructing plasmid 191-47, various DNA fragments were joined by recombinant DNA techniques using either naturally occurring restriction sites or synthetic linker DNA. Details concerning the construction of these genes contained in plasmid 191-47 can be seen in FIG. 2. The first segment of DNA (segment 1, FIG. 2) contains the gpX promoter region including the residues encoding the first seven amino acids of the gpX gene, and was derived from a subclone of the PRV BamHI #10 fragment as an approximately 800 base pair SalI to BamHI fragment. The second segment of DNA (segment 2, FIG. 2) contains the E. coli β-galactosidase coding region from amino acid 10 to amino acid 1024 and was derived from the plasmid pJF751 (obtained from Jim Hoch, Scripps Clinic and Research Foundation) as an approximately 3300 base pair BamHI to BalI fragment followed by an approximately 40 base pair Ava I to Sma I fragment. The third segment of DNA (segment 3, FIG. 2) contains the gpX poly A signal sequence and was derived from a subclone of the PRV BamHI #7 fragment as an approximately 700 base pair NdeI to StuI fragment. Segment three was joined to segment two by ligating the NdeI end which had been filled in according to the POLYMERASE FILL-IN REACTION, to the SmaI site. The fourth segment of DNA (segment 4 FIG. 2) contains the gpX promoter (TATA box and cap site) and was derived from a subclone of the PRV BamHI #10 fragment as an approximately 330 base pair NaeI to AluI fragment. Additionally, segment four contains approximately 36 base pairs of HSV TK 5' untranslated leader sequence as a PstI to BglII fragment in which the PstI site has been joined to the AluI site through the use of a synthetic DNA linker (McKnight and Kingbury, 1982). DNA segments four through six were inserted as a unit into the unique Kpn I site of segment three which is located 3' of the gpX poly A signal sequence. The fifth segment of DNA (segment 5, FIG. 2) contains the entire coding region of the IBDV large segment of RNA (cDNA clone) as an approximately 3400 base pair SmaI to HpaI fragment. The SmaI site of segment five was fused to the BglII site of segment four which had been filled in according to the POLYMERASE FILL IN REACTION Expression of the IBDV gene (5' VP2-VP4-VP3 3'), is under the control of the gpX promoter (segment 4), but utilizes its own natural start and stop codons. The sixth segment of DNA (segment 6, FIG. 2) contains the HSV TK poly-A signal sequence as an approximately 800 base pair SmaI fragment (obtained from Bernard Roizman, Univ. of Chicago). The HpaI site of segment five was fused to the SmaI site of segment six through the use of a synthetic DNA liner.

In summary, the construct used to create S-HVT-003 (plasmid 191-47) contains (5' to 3') the PRV promoter, the gpX TATA box, the gpX cap site, the first seven amino acids of gpX, the *E. coli* β-galactosidase (lacZ) gene, the PRV poly-A signal sequence, the PRV gpX promoter, the gpX TATA box, the gpX cap site, a fusion within the gpX untranslated 5' leader to the IBDV gene, IBDV start codon, a fusion within the IBDV untranslated 3' end to HSV TK untranslated 3' end, and the TK poly-A signal sequence. The cassette containing these genes was engineered such that it was flanked by two EcoRI restriction endonuclease sites. As a result, an approximately 9100 base pair fragment containing both lacZ gene and the IBDV gene can be obtained by digestion with EcoRI. Henceforth, the 9161 base pair EcoRI fragment will be referred to as the IBDV/lacZ cassette. The following procedures were used to construct S-HVT-003 by homologous recombination. The IBDV/lacZ cassette was inserted into the unique XhoI site present within a subclone of the HVT BamHI #16 fragment. To achieve this, the XhoI site was first changed to an EcoRI site through the use of an EcoRI linker. This site had previously been shown to be nonessential in HVT by the insertion of lacZ (S-HVT-001). It was also shown that the flanking homology regions in BamHI #16 were efficient in homologous recombination. Shown in FIG. 3, the genomic location of the BamHI #16 fragment maps within the unique long region of HVT. The complete nucleotide sequence of the approximately 3329 base pair BamHI #16 fragment is presented as seq ID #3. HVT DNA was prepared by the PREPARATION OF HERPESVIRUS DNA procedure. Cotransfections of HVT DNA and plasmid DNA into primary chick embryo fibroblast (CEF) cells were done according to the DNA TRANSFECTION FOR GENERATING RECOMBINANT HERPESVIRUS. The recombinant virus resulting from the cotransfection stock was purified by three successive rounds of plaque purification using the BLUOGAL SCREEN FOR RECOMBINANT HERPESVIRUS procedure. When 100% of the plaques were blue, the DNA was analyzed for the presence of the IBDV gene by the SOUTHERN BLOTTING OF DNA procedure. Southern blots, probing EcoRI digested S-HVT-003 DNA with an IBDV specific nick translated probe (plasmid 2-84/2-40), confirmed the presence of the 9100 base pair EcoRI fragment. This result confirmed that S-HVT-003 contained both the lacZ gene and the IBDV gene incorporated into its genome. Additional Southern blots, using a probe specific for BamHI #16, confirmed that the homologous recombination occurred at the appropriate position in BamHI #16 and that no deletions were created. No differences in the growth of S-HVT-003 compared to wild type virus (S-HVT-000) were observed in vitro.

Expression of IBDV specific proteins from S-HVT-003 were assayed in vitro using the WESTERN BLOTTING PROCEDURE. Cellular lysates were prepared as described in PREPARATION OF HERPESVIRUS CELL LYSATES. Briefly, the proteins contained in the cellular lysates of S-HVT-003 were separated by polyacrylamide gel electrophoresis, transferred to nitrocellulose, and probed with either an antiserum made against denatured purified IBDV capsid proteins or antiserum made against a synthetic peptide corresponding to a predicted imuno dominant region of the IBDV 40 kd (VP2) capsid protein. The filters were washed and treated with [$^{125}$I] protein A to detect the position of the bound antibodies. FIG. 4 shows the results obtained using the antiserum made against denatured purified IBDV capsid proteins, which have been shown by the applicants to react primarily with VP3 (32 kd protein). As seen, S-HVT-003 produces a protein which is immunologically indistinguishable from the authentic VP3 protein from intact IBDV virions. Moreover, the polyprotein appears to be processed correctly, producing a VP3 species that comigrates with the authentic VP3 protein. Recent evidence using an Australian IBDV stain indicates that VP4 is involved in the processing of the precursor polyprotein into mature VP2 and VP3 protein species (Jagadish, et al., 1988). FIG. 5 shows the results obtained using a rabbit antiserum raised against a synthetic peptide that is homologous to a 14 amino acid region of the IBDV VP2 (40 kd) capsid protein. As seen, S-HVT-003 produces a protein that is immunologically indistinguishable from the authentic viral VP2 protein. In addition, the VP2 protein produced from S-HVT-003 comigrates with the 40 kd species of VP2 isolated from intact IBDV virions. This species represents a major component of infectious (complete) viral particles.

In summary, analysis of the expression of IBDV specific proteins from S-HVT-003 has shown that the polyprotein is processed in CEF cell culture, producing proteins of the appropriate size that react to immunological reagents specific for either VP2 or VP3 proteins on Western blots.

The following set of experiments was carried out in chickens to analyze the in vivo expression of the IBDV genes contained within S-HVT-003 as determined by seroconversion data, serum neutralization results, and protection from IBDV challenge.

The first experiment was designed to show the seroconversion of chickens to IBDV upon being vaccinated with S-HVT-003. Eleven 11-week-old chickens, seronegative to HVT and IBDV were obtained from SPAFAS Inc. Six birds were vaccinated subcutaneously in the abdominal region with 0.5 ml of a cellular suspension of CEF cells containing S-HVT-003 (40,000 PFU/ml). Serum samples were obtained every seven days for eight weeks for all birds in this study. On day 28 (4th week), three of these birds received a boost of S-HVT-003, while the other three birds received 0.5 ml of an inactivated IBDV vaccine inoculated subcutaneously in the cervical region. Three additional birds were given only the inactivated vaccine on day 28. Two birds served as contact controls and received no vaccinations. On day 56, all birds were sacrificed and necropsied. Table 1 show the results of the serum neutralization assay against IBDV. No detectable SN activity was observed in the birds given only S-HVT-003. Additionally, only one of the three birds that were given only the inactivated vaccine demonstrated low but detectable SN activity. SN titers were also detected in one of the three birds that received the S-HVT-003 followed by the inactivated IBDV vaccine boost; these titers were at a much higher level than with the inactivated IBDV vaccine alone. These results suggest that S-HVT-003 is priming the chicken for a secondary response against IBDV. In vitro analysis of the serum samples by WESTERN BLOTTING confirmed the seroconversion of the chickens to IBDV upon vaccination with S-HVT-003 both prior to and after boosts administered on day 28.

TABLE 1

| Vaccine Group | Bird No. | DAY | | | | | |
|---|---|---|---|---|---|---|---|
| | | 28 | 31 | 35 | 38 | 42 | 49 |
| HVT-003 | 265 | <2 | <2 | <2 | <2 | <2 | <2 |
| HVT-003 | 266 | <2 | <2 | <2 | <2 | <2 | <2 |
| | 267 | <2 | <2 | <2 | <2 | <2 | <2 |
| HVT-003 | 260 | <2 | <2 | <2 | <2 | <2 | <2 |
| IBDV[a] | 264 | <2 | <2 | <2 | 1:64 | 1:256 | 1:512 |
| | 269 | <2 | <2 | <2 | <2 | <2 | <2 |
| C | 261 | <2 | <2 | <2 | <2 | <2 | <2 |
| IBDV[a] | 262 | <2 | <2 | <2 | <2 | 1:4 | 1:4 |
| | 263 | <2 | <2 | <2 | <2 | <2 | <2 |
| C | 270 | <2 | <2 | <2 | <2 | <2 | <2 |
| | 271 | <2 | <2 | <2 | <2 | <2 | <2 |

[a]Commercial

In the second experiment, twenty five 1-day old SPF chicks were vaccinated with S-HVT-003 (20 with 0.2 ml subcutaneously and 5 by bilateral eyedrop). Twenty chicks were kept as controls. On days four and seven postinfection, five vaccinates and two control birds were bled, sacrificed and their spleens removed for virus isolation. Spleen cell suspensions were made by standard method, and $\neq 1 \times 10^6$ cells in 3 ml of chick embryo fibroblast (CEF) growth media were inoculated directly onto secondary cells. Cultures were incubated for 6–7 days and then scored for cytopathic effects (CPE) as determined by observing cell morphology. The cultures were passed a second time, and again scored for CPE. The results are shown in Table 2. All nonvaccinated control birds remained negative for HVT for both day 4 and 7 spleen cell isolations. Four out of the five birds vaccinated with S-HVT-003 were positive for HVT at day 4 for both the first and second passages. One bird did not produce virus, this may represent a vaccination failure. Five out of five birds were positive for HVT on day 7 at both passage one and two. Overall, the vector recovery experiment demonstrates that S-HVT-003 replicates as well as wild type HVT virus in vivo and that insertion of the IBDV/lacZ cassette into the XhoI site of BamHI #16 does not result in detectable attenuation of virus. Subsequent experiments examining the recovered virus by the BLUOGAL SCREEN FOR RECOMBINANT HERPESVIRUS procedure confirmed the in vivo stability of S-HVT-003, by demonstrating β-galactosidase expression in 100% of the viruses.

TABLE 2

| | Harvest Date | | | |
|---|---|---|---|---|
| | Day 4 | | Day 7 | |
| Sample | P1 | P2 | P1 | P2 |
| N1 | – | – | | |
| N2 | – | – | | |
| N3 | | | – | – |
| N4 | | | – | – |
| T1 | – | – | | |
| T2 | 2+ | 2+ | | |
| T3 | 2+ | 2+ | | |

TABLE 2-continued

| | Harvest Date | | | |
|---|---|---|---|---|
| | Day 4 | | Day 7 | |
| Sample | P1 | P2 | P1 | P2 |
| T4 | + | 4+ | | |
| T5 | 3+ | 3+ | | |
| T6 | | | 2+ | contaminated |
| T7 | | | + | 5+ |
| T8 | | | + | 5+ |
| T8 | | | + | 5+ |
| T9 | | | + | 5+ |
| T10 | | | + | 5+ |

N = control,
T = vaccinated
CPE ranged from negative (–) to 5+

At days 0, 4, 7, 14, 21, and 27 postinfection, blood samples were obtained from the rest of the chickens for determining serum ELISA titers against IBDV and HVT antigens as well as for virus neutralizing tests against IBDV. Additionally, at 21 days postinfection five control and fourteen vaccinated chicks were challenged with virulent IBDV by bi-lateral eyedrop ($10^{3.8}\text{EID}_{50}$). All birds were sacrificed 6-days post challenge and bursa to body weight ratios were calculated. A summary of the results is shown in tables X and XI, respectively. As presented in Table 3, no antibodies were detected against HVT antigens by ELISA prior to 21–27 days post vaccination. In chickens, the immune response during the first two weeks post hatch is both immature and parentally suppressed, and therefore these results are not totally unexpected. In contrast, IBDV ELISA's were negative up to day 21 postvaccination, and were only detectable after challenge on day 27. The ELISA levels seen on day 27 postvaccination indicate a primary response to IBDV. Table 3I comparing the Bursa-to-Body weight ratios for challenged controls and vaccinated/challenged groups show no significant differences. Vaccination with S-HVT-003 under these conditions did not prevent infection of the vaccinated birds by IBDV challenge, as indicated by the death of four vaccinated birds following challenge.

TABLE 3

| Sample Group | | ELISA | | VN |
|---|---|---|---|---|
| | | HVT | IBDV | IBDV |
| C-0 | (n = 3) | 0 | 0 | <100 |
| C-4 | (n = 2) | 0 | 0 | nd |
| T-4 | (n = 5) | 0 | 0 | nd |
| C-7 | (n = 2) | 0 | 0 | <100 |
| T-7 | (n = 5) | 0 | 0 | <100 |
| C-14 | (n = 5) | 0 | 0 | nd |
| T-14 | (n = 14) | 0 | 0 | <100 |
| C-21 | (n = 5) | 0 | 0 | nd |
| T-21 | (n = 14) | 1 | 0 | <100 |
| C-27 | (n = 5) | 0 | 0 | nd |
| CC-27 | (n = 5) | 0 | 5 | nd |
| CT-27 | (n = 10) | 3.2 | 2 | nd |

C = control,
T = vaccinated,
CC = challenged control,
CT = Challenged & vaccinated.
ELISA titers are GMTs and they range from 0–9.

TABLE 4

| Sample Group | Body wt. | Bursa wt. | BBR |
|---|---|---|---|
| Con. (n = 5) | 258.8 | 1.5088 | 0.0058 |
| Chall. | 209 | 0.6502 | 0.0031 |
| Con. (n = 5) Chall. Treated (n = 10) | 215.5 | 0.5944 | 0.0027 |

Values are mean values.
Body weights are different in control group because challenged birds did not feed well. Four challenged-treated birds died.

A third experiment was conducted repeating Experiment 2 but using immunologically responsive chicks (3 weeks of age). Six three week old SPF leghorn chickens were vaccinated intraperitoneally with 0.2 ml of S-HVT-003 (one drop in each eye). Serum samples were obtained every seven days for six-weeks and the birds were challenged with the virulent USDA standard challenge IBDV virus on day 43 postvaccination. Six days post challenge, the control, vaccinated-challenged, and challenged groups were sacrificed and bursas were harvested for probing with anti-IBDV monoclonal antibodies (MAB) (provided by Dr. David Snyder, Virginia-Maryland Regional College of Veterinary Medicine). Bursal homogenates were prepared by mixing 1 ml of 0.5% NP40 with one bursa. Bursa were then ground and briefly sonicated. Supernatants from the homogenates were reacted with the R63 MAB which had been affixed to 96-well Elisa plates via a protein A linkage. After incubation, a biotin labeled preparation of the R63 MAB was added. After washing, an avidin-horse radish peroxidase conjugate was added and incubated. Tests were developed with Tris-malcate buffer (TMB)+$H_2O_2$ substrate. The test results are presented in Table 5. The data show the presence of high levels of IBDV antigen in all bursa in the vaccinate-challenged group and in the challenged group. No IBDV antigen was detected in the controls. IBDV specific antigen could be detected at dilutions of over 1/1000, and there does not appear to be differences between vaccinated and non-vaccinated challenged groups. HVT titers as determined by ELISA were first detectable at day 7 in four out of the six birds vaccinated. By day 14, six out of six vaccinated birds showed titers to HVT. All six birds continued to show HVT titers throughout the experiment. No IBDV SN titers were seen prior to the challenge. In contrast, analysis of these same serum samples by the WESTERN BLOTTING procedure demonstrated the seroconversion of chickens vaccinated with S-HVT-003 to IBDV prior to administration of the virus challenge. The level of response, however, remains small unless boosted by challenge. Comparison between the vaccinated/challenged and challenged only groups clearly demonstrates that the level of reactivity by Western blots is much higher in the vaccinated/challenged group. These results show that S-HVT-003 is seroconverting vaccinated birds to IBDV, and suggest that the level of IBDV specific expression are not high enough to induce a neutralizing response in the birds.

S-HVT-003 shows the merit of the vaccine approach the applicants have invented. HVT has been engineered to simultaneously express the foreign antigens (β-galactosidase and IBDV antigens) that are recognized in the host by an immune response directed to these proteins. Applicants' invention will enable progression towards a product based on this technology.

TABLE 5

Serology: Herpes/IBDV ELISA titer

| Bird # | Bleed Date | | | | | | | |
|---|---|---|---|---|---|---|---|---|
|  | 11/3 | 11/10 | 11/14 | 11/24 | 12/1 | 12/8 | 12/15 | 12/22 |
| Vaccinated Challenged | | | | | | | | |
| 221 | 0/0 | 7/0 | 5/0 | 6/0 | 5/0 | 5/0 | 5/0 | 3/3 |
| 41 | 0/0 | 4/0 | 4/0 | 1/0 | 1/0 | 1/0 | 1/0 | 1/3 |
| 42 | 0/0 | 3/0 | 2/0 | 1/0 | 5/0 | 5/0 | 5/0 | 3/2 |
| 43 | 0/0 | 0/0 | 5/0 | 5/0 | 5/0 | 5/0 | 3/0 | 3/2 |
| 44 | 0/0 | 1/0 | 5/0 | 1/0 | 2/0 | 1/0 | 1/0 | 2/4 |
| 45 | 0/0 | 0/0 | 1/0 | 1/0 | 1/0 | 1/0 | 1/0 | 1/3 |
| Control | | | | | | | | |
| 28 | 0/0 | | | | | | | 0/0 |
| 38 | 0/0 | | | | | | | 0/0 |
| 73 | 0/0 | | | | | | | 0/0 |
| 75 | 0/0 | | | | | | | 0/0 |
| Challenged only | | | | | | | | |
| 40 | 0/0 | | | | | | | 0/3 |
| 74 | 0/0 | | | | | | | 0/5 |
| 39 | 0/0 | | | | | | | 0/3 |
| 72 | 0/0 | | | | | | | 0/3 |

Maximum titer level is 9

Example 3

S-HVT-004

S-HVT-004 is a recombinant herpesvirus of turkeys that contains the Marek's disease virus (MDV) glycoprotein A (gpA) gene inserted into the long unique region, and the β-galactosidase (lacZ) gene also inserted in the long unique region. The MDV antigen is more likely to elicit the proper antigentic response than the HVT equivalent antigen.

The MDV gpA gene was cloned by standard DNA cloning gpA procedures. An EcoRI restriction fragment had been reported to contain the MDV gpA gene (Isfort et al., 1984) and this fragment was identified by size in the DNA clones. The region of the DNA reported to contain the gpA gene was sequenced by applicants and found to contain a glycoprotein gene as expected. The DNA from this gene was used to find the corresponding gene in HVT by the SOUTHERN BLOTTING OF DNA procedure, and a gene in HVT was identified that contained a very similar sequence. This gene is the same gene previously called gpA (Isfort et al., 1984).

Figure 6A:
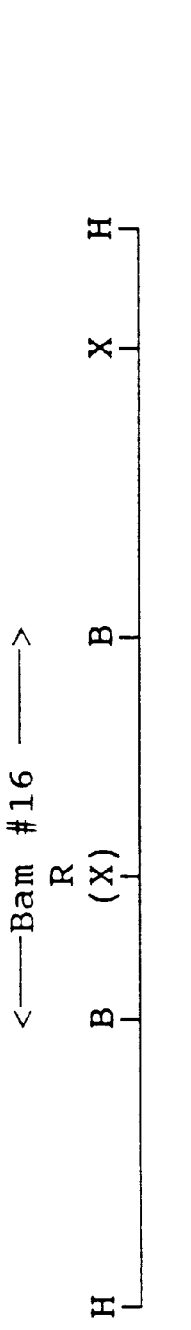
Figure 6B:
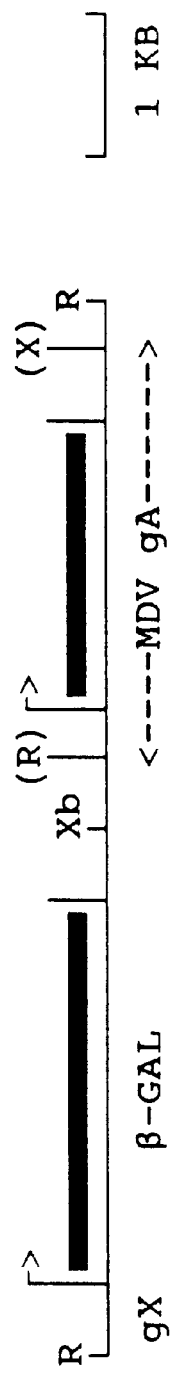

For insertion into the genome of HVT, the MDV gpA gene was used intact because it would have good herpesvirus signal sequences already. The lacZ gene was inserted into the XhoI fragment in BamHI fragment #16, and the MDV gpA gene was inserted behind lacZ as shown in FIGS. 6A and 6B. Flanking regions in BamHI #16 were used for the homologous recombination. HVT DNA and plasmid DNA were co-transfected according to the DNA TRANSFECTION FOR GENERATING RECOMBINANT HERPESVIRUS procedure into primary chick embryo fibroblast (CEF) cells. The virus from the transfection stock was purified by successive plaque purifications using the BLUOGAL SCREEN FOR RECOMBINANT HERPESVIRUS procedure. At the end of this procedure, when 100% of the plaques were blue, the DNA was analyzed for the presence of the MDV gpA gene. S-HVT-004 is a recombinant virus that contains both the β-galactosidase gene and the MDV gpA gene incorporated into the genome.

Figure 6C:
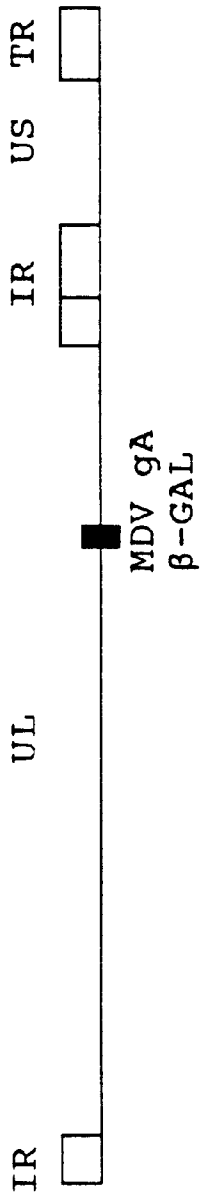

FIG. 6C shows the structure of S-HVT-004.

Example 4
Newcastle Disease Virus

Newcastle disease virus (NDV) is closely related to PI-3 in overall structure. We have engineered the hemagglutinin (HN) and fusion (F) genes of PI-3 for expression in IBR (ref). Similarly we have cloned the hemagglutinin (HN) and fusion (F) genes from NDV for use in the herpesvirus delivery system (Herpesvirus of turkeys, HVT).

The procedures that we have utilized for construction of herpesvirus control sequences for expression have been applied to NDV.

Infectious Bronchitis Virus

Infectious bronchitis virus (IBV) is a virus of chickens closely related in overall structure to TGE. We have engineered the major neutralizing antigen of TGE for expression in PRV (ref). Similarly we have cloned the major neutralizing antigens from three strains of IBV: Massachusetts (SEQ ID NO: 14), Connecticut (SEQ ID NO: 16), and Arkansas-99 (SEQ ID NO: 18) for use in a herpesvirus delivery system (HVT).

The procedures that we have utilized for the construction of herpesvirus control sequences for expression have been applied to IBV.

Example 5
S-HVT-045

S-HVT-045 is a recombinant herpesvirus of turkeys that contains the Marek's disease virus (MDV) glycoprotein B (gpB) gene inserted into the short unique region. The MDV antigen is more likely to elicit the proper antigenic response than the HVT equivalent antigen. S-HVT-045 has been deposited pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A.

The MDV gpB gene was cloned by standard DNA cloning procedures. The MDV gpB gene was localized to a 3.9 kb EcoRI-SalI fragment using an oligonucleotide probe based on the HSV gB sequence in a region found to be conserved among known herpesvirus gB genes. The restriction map 3.9 kb EcoRI-SalI fragment is similar to the published map (Ross et al., 1989).

For insertion into the HVT genome, the MDV gpB was used intact because it would have good herpesvirus signal sequences already. The MDV gpB gene was inserted into a cloned 17.15 kb BamHI-EcoRI fragment derived from the HVT BamHI #1 fragment. The site used for insertion was the StuI site within HVT US2, previously utilized for the construction of S-HVT-012. The site was initially altered by insertion of a unique HindIII linker, and the MDV gpB gene was inserted by standard DNA cloning procedures. Flanking regions in the 17.15 kb BamHI-EcoRI fragment were used, together with the remaining cloned HVT fragments using the PROCEDURE FOR GENERATING RECOMBINANT HERPESVIRUSES FROM OVERLAPPING SUBGENOMIC FRAGMENTS. The virus obtained from the transfection stock was plaque purified and the DNA was analyzed for the presence of the MDV gpB gene. S-HVT-045 is a recombinant virus that contains the MDV gpB gene incorporated into the genome at the StuI site in HVT US2 gene.

Testing of Recombinant S-HVT-045

Two studies were conducted to demonstrate the effectiveness of these recombinant HVT/MDV viruses in protecting against challenge with virulent Marek's disease virus. In Study A, one-day-old specific pathogen free (SPF) chicks were vaccinated with either S-HVT-045 or S-HVT-046. Seven days post-vaccination, vaccinated chicks, and non-vaccinated, control chicks were challenged with the highly virulent MD-5 strain of Marek's disease virus. Following a 6-week post-challenge observation period for clinical signs typical of Marek's disease, all chicks were necropsied and examined for lesions diagnostic of Marek's disease. The results, in Table 6, show that both recombinant viruses gave complete protection against a challenge that caused Marek's disease in 90% of non-vaccinated control chicks.

In a second study, one-day-old chicks were vaccinated either with S-HVT-045 or S-HVT-047. A third group of chicks were vaccinated with a USDA-licensed, conventional vaccine comprised of HVT and SB-1 viruses. Five days post-vaccination, the vaccinated chicks and a group of non-vaccinated, control chicks were challenged with virulent Marek's virus, strain RBLB. The chicks were observed for 8 weeks for clinical signs of Marek's disease, then necropsied and observed for Marek's lesions. This study demonstrated the ability of HVT-045 and HVT-047 to provide 100% protection against challenge (Table 1). The commercial vaccine gave 96% protection, and 79% of the non-vaccinated chicks developed Marek's disease.

TABLE 6

EFFICACY OF RECOMBINANT HVT/MDV VIRUSES
TO PROTECT SUSCEPTIBLE CHICKS
AGAINST VIRULENT MAREK'S DISEASE VIRUS

| | Marek's Protection | |
| --- | --- | --- |
| Vaccine Group | MD-5 Challenge | RB1B Challenge |
| S-HVT-045 | 20/20 | 24/24 |
| S-HVT-046 | 20/20 | Not Tested |
| S-HVT-047 | Not Tested | 24/24 |
| HVT[a] | Not Tested | 24/25 |
| Controls | 2/20 | 5/24 |

[a]Commercial

Example 6
S-HVT-012

S-HVT-012 is a recombinant herpesvirus of turkeys that contains the E. coli β-galactosidase (lacZ) gene inserted into the short unique region. The lacZ gene was used to determine the viability of this insertion site in HVT [ATCC F-126 ("Calnek")]. S-HVT-012 has been deposited pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A.

For insertion into the genome of HVT, the β-galactosidase gene was introduced into the unique StuI site of the cloned EcoRI fragment #7 of HVT, i.e., the fragment containing the StuI site within the US2 gene of HVT (as described in Methods and Materials). Flanking regions of EcoRI fragment #7 were used for homologous recombination. HVT DNA and plasmid DNA were co-transfected according to the DNA TRANSFECTION FOR GENERATING RECOMBINANT VIRUS procedure into primary chick embryo fibroblast (CEF) cells. A blue virus obtained from the transfection stock was purified by successive plaque purifications using the BLUOGAL SCREEN FOR RECOMBINANT HERPESVIRUS procedure. At the end of this procedure, when 100% of the plaques were blue, the DNA was analyzed for the presence of the lacZ gene. S-HVT-012 is a recombinant virus that contains the lacZ gene incorporated into the genome at the StuI site within the US2 gene of HVT.

Testing of Recombinant S-HVT-012

S-HVT-012 may be formulated as a vaccine in the same manner as S-HVT-045. When administered to chickens, such a vaccine provides protection against Marek's disease virus.

Example 7
Sites for Insertion of Foreign DNA into HVT

In order to define appropriate insertion sites, a library of HVT BamHI and EcoRI restriction fragments was generated. Several of these restriction fragments (BamHI fragments #16 and #13, and EcoRI fragments #6, #7, and #9 (see FIG. 1)) were subjected to restriction mapping analysis. One unique restriction site was identified in each fragment as a potential insertion site. These sites included XhoI in BamHI fragments #13 and #16, and EcoRI fragment #9 and SalI in EcoRI fragment #6 and StuI in EcoRI fragment #7. A β-galactosidase (lacZ) marker gene was inserted in each of the potential sites. A plasmid containing such a foreign DNA insert may be used according to the DNA COTRANSFECTION FOR GENERATING RECOMBINANT HERPESVIRUSES to CONSTRUCT a HVT containing the foreign DNA. For this procedure to be successful it is important that the insertion site be in a region non-essential to the replication of the HVT and that the site be flanked with HVT DNA appropriate for mediating homologous recombination between virus and plasmid DNAs. The plasmids containing the lacZ marker gene were utilized in the DNA COTRANSFECTION FOR GENERATING RECOMBINANT HERPESVIRUSES. The generation of recombinant virus was determined by the BLUOGAL SCREEN FOR RECOMBINANT HERPESVIRUS. Three of the five sites were successfully used to generate a recombinant virus. In each case the resulting virus was easily purified to 100%, clearly defining an appropriate site for the insertion of foreign DNA. The three homology vectors used to define these sites are described below.

Example 7A

Homology Vector 172-29.31

The homology vector 172-29.31 contains the HVT BamHI #16 fragment and is useful for the insertion of foreign DNA into HVT. Plasmid 172-29.31 contains a unique XhoI restriction site into which foreign DNA may be cloned. We have demonstrated that the XhoI site in homology vector 172-29.31 may be used to insert foreign DNA into HVT by the construction of at least three recombinant HVT (see examples 1–3).

The homology vector 172-29.31 was further characterized by DNA sequence analysis. The complete sequences of the BamHI #16 fragment was determined. Approximately 2092 base pairs of the adjacent BamHI #13 fragment was also determined (see SEQ ID 3). This sequence indicates that the open reading frame coding for HVT glycoprotein A (gA) spans the BamHI #16—BamHI #13 junction. The HVT gA gene is homologous to the HSV-1 glycoprotein C (gC). The XhoI site interrupts an ORF which lies directly upstream of the HVT gA gene. This ORF shows amino acid sequence homology to the PRV p43 and the VZV gene 15. The PRV and VZV genes are the homologues of HSV-1 UL43. Therefore we have designated this ORF as HVT UL43. It should be noted that the HVT UL43 does not exhibit direct homology to HSV-1 UL43. Although HVT UL43 is located upstream of the HVT gC homologue it is encoded on the same DNA strand as HVT gA, where as the HSV-1 UL43 is on the opposite strand relative to HSV-1 gC. The XhoI site interrupts UL43 at approximately amino acid 6, suggesting that the UL43 gene is non-essential for HVT replication.

Example 7B

Homology Vector 435-47.R17

The homology vector 435-47.R17 contains the HVT EcoRI #7 fragment and is useful for the insertion of foreign DNA into HVT. Plasmid 435-47.R17 contains a unique HindIII restriction site into which foreign DNA may be cloned. The HindIII restriction site in plasmid results from the insertion of a HindIII linker into the naturally occurring StuI site of EcoRI fragment #7. We have demonstrated that the HindIII site in homology vector 435-47.R17 may be used to insert foreign DNA into HVT by the construction of at least 25 recombinant HVT.

DNA sequence analysis at the StuI indicated that this fragment contains open reading frames coding for US10, US2, and US3. The StuI site interrupts US2 at approximately amino acid 124, suggesting that the US2 gene is non-essential for HVT replication.

Example 7C

Homology Vector 172-63.1

The homology vector 172-63.1 contains the HVT EcoRI #9 fragment and is useful for the insertion of foreign DNA into HVT. Plasmid 172-63.1 contains a unique XhoI restriction site into which foreign DNA may be cloned. We have demonstrated that the XhoI site in homology vector 172-63.1 may be used to insert foreign DNA into HVT by the construction of S-HVT-014 (see example 8).

Example 8

S-HVT-014

S-HVT-014 is a recombinant herpesvirus of turkeys that contains the *E. coli* β-galactosidase (lacZ) gene inserted into the long unique region. The lacZ gene was used to determine the viability of this insertion site in HVT [ATCC F-126 ("Calnek")].

For insertion into the genome of HVT, the β-galactosidase gene was introduced into the unique XhoI site of the cloned EcoRI fragment #9 (as described in Methods and Materials). Flanking regions of EcoRI fragment #8 were used for homologous recombination. HVT DNA and plasmid DNA were co-transfected according to the DNA TRANSFECTION FOR GENERATING RECOMBINANT VIRUS procedure into primary chick embryo fibroblast (CEF) cells. A blue virus obtained from the transfection stock was purified by successive plaque purifications using the BLUOGAL SCREEN FOR RECOMBINANT HERPESVIRUS procedure. At the end of this procedure when 100% of the plaques were blue. S-HVT-014 is a recombinant virus that contains the lacZ gene incorporated into the genome at the XhoI site within the EcoRI #9 fragment of HVT.

Testing of Recombinant S-HVT-014

S-HVT-014 may be formulated as a vaccine in the same manner as S-HVT-045. When administered to chickens, such a vaccine provides protection against Marek's disease virus.

Example 9

S-HVT-005

S-HVT-005 is a recombinant herpesvirus of turkeys that contains the *E. coli* β-galactosidase (lacZ) gene inserted into the long unique region. The lacZ gene was used to determine the viability of this insertion site in HVT [ATCC F-126 ("Calnek")].

For insertion into the genome of HVT, the β-galactosidase gene was introduced into an approximately 1300 base pair deletion of the XhoI #9 fragment of HVT. The deletion which lies between the unique MluI and EcoRV sites removes the complete coding region of the HVT gA gene (see SEQ ID 3). Flanking regions of XhoI fragment #9 were used for homologous recombination. HVT DNA and plasmid DNA were co-transfected according to the DNA TRANSFECTION FOR GENERATING RECOMBINANT VIRUS procedure into primary chick embryo fibroblast (CEF) cells. A blue virus obtained from the transfection stock was purified by successive plaque purifications using the BLUOGAL SCREEN FOR RECOMBINANT HERPESVIRUS procedure. At the end of this procedure, when 100% of the plaques were blue, the DNA was analyzed for the presence of the lacZ gene. S-HVT-005 is a recombinant virus that contains the lacZ gene incorporated into the genome at in place of the deleted gA gene of HVT.

Testing of Recombinant S-HVT-005

S-HVT-005 may be formulated as a vaccine in the same manner as S-HVT-045. When administered to chickens, such a vaccine provides protection against Marek's disease virus.

Example 10

Marek's Disease Vaccines

Recombinant HVT expressing glycoproteins from MDV make superior vaccines for Marek's Disease. We have constructed several recombinant HVT expressing MDV glycoproteins S-HVT-004 (example 3), S-HVT-005 (example 9), S-HVT-045 (example 5), S-HVT-046 (example 10A), S-HVT-047 (example 10B), S-HVT-062 (example 10C).

Example 10A

S-HVT-046

S-HVT-046 is a recombinant herpesvirus of turkeys that contains the Marek's disease virus (MDV) glycoprotein B (gB) and glycoprotein A (gA) genes inserted into the short unique region. The MDV genes are inserted in the same transcriptional orientation as the US2 gene. The MDV antigens are more likely to elicit the proper antigenic response than the HVT equivalent antigen.

S-HVT-046 was constructed according to the PROCEDURE FOR GENERATING RECOMBINANT HERPESVIRUS FROM SUBGENOMIC DNA FRAGMENTS. The following combination of subgenomic clones and enzymes were used: 407-32.2C3 with NotI, 172-07.BA2 with BamHI, 407-32.5G6 with NotI, 407-32.1C1 with NotI, 437-26.24 with BamHI and HindIII, 437-26.26 with BamHI and HindIII, and 456-17.22 uncut. Insertion of the appropriate DNA was confirmed by southern blot analysis.

Example 10B

S-HVT-047

S-HVT-047 is a recombinant herpesvirus of turkeys that contains the MDV gB and gA genes inserted into the short unique region. The MDV genes are inserted in the opposite transcriptional orientation as the US2 gene. The MDV antigens are more likely to elicit the proper antigenic response than the HVT equivalent antigen.

S-HVT-047 was constructed according to the PROCEDURE FOR GENERATING RECOMBINANT HERPESVIRUS FROM SUBGENOMIC DNA FRAGMENTS. The following combination of subgenomic clones and enzymes were used: 407-32.2C3 with NotI, 172-07.BA2 with BamHI, 407-32.5G6 with NotI, 407-32.1C1 with NotI, 437-26.24 with BamHI and HindIII, 437-26.26 with BamHI and HindIII, and 456-17.18 uncut. Insertion of the appropriate DNA was confirmed by southern blot analysis.

Example 10C

S-HVT-062

S-HVT-062 is a recombinant herpesvirus of turkeys that contains the MDV gB, glycoprotein D (gD) and gA genes inserted into the short unique region. The MDV genes are inserted in the same transcriptional orientation as the US2 gene. The MDV antigens are more likely to elicit the proper antigenic response than the HVT equivalent antigen. S-HVT-062 has been deposited pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2401 on Feb. 23, 1993.

S-HVT-062 was constructed according to the PROCEDURE FOR GENERATING RECOMBINANT HERPESVIRUS FROM SUBGENOMIC DNA FRAGMENTS. The following combination of subgenomic clones and enzymes were used: 407-32.2C3 with NotI, 172-07.BA2 with BamHI, 407-32.5G6 with NotI, 407-32.1C1 with NotI, 437-26.24 with BamHI and HindIII, 566-41.5, with BamHI and HindIII, and 456-17.22 uncut. Insertion of the appropriate DNA was confirmed by southern blot analysis.

Testing of Recombinant HVT Expressing MDV Antigens

Two studies were conducted to demonstrate the effectiveness of these recombinant HVT/MDV viruses in protecting against challenge with virulent Marek's disease virus. In Study 1, one-day-old specific pathogen free (SPF) chicks were vaccinated with either S-HVT-045, S-HVT-046, or S-HVT-047. Five days post-vaccination, vaccinated chicks, and non-vaccinated, control chicks were challenged with MDV. Following a 6-week post-challenge observation period for clinical signs typical of Marek's disease, all chicks were necropsied and examined for lesions diagnostic of Marek's disease. The results, in Table 7, show these recombinant viruses gave complete protection against a challenge that caused Marek's disease in 84% of non-vaccinated control chicks.

In the second study, one-day-old chicks were vaccinated with S-HVT-062. Two more groups of chicks were vaccinated with a USDA-licensed, conventional vaccines comprised of HVT and a combination HVT and SB-1 viruses. Five days post-vaccination, the vaccinated chicks and a group of non-vaccinated, control chicks were challenged with MDV. The chicks were observed for 8 weeks for clinical signs of Marek's disease, then necropsied and observed for Marek's lesions. This study demonstrated the ability of S-HVT-062 to provide 100% protection against challenge (Table 7). The commercial vaccines gave 81% and 95% protection, respectively and 100% of the non-vaccinated chicks developed Marek's disease.

TABLE 7

EFFICACY OF RECOMBINANT HVT/MDV VIRUSES AGAINST VIRULENT MAREK'S VIRUS CHALLENGE

| Study | Vaccine Group | Dose[a] | Protection[b] |
|---|---|---|---|
| 1 | S-HVT-045 | $2.2 \times 10^3$ | 24/24 (100%) |
| 1 | S-HVT-046 | $2.2 \times 10^3$ | 20/20 (100%) |
| 1 | S-HVT-047 | $2.2 \times 10^3$ | 24/24 (100%) |
| 1 | Controls | | 7/44 (16%) |
| 1 | HVT/SB-1 | | 24/25 (96%) |
| 2 | S-HVT-062 | $7.5 \times 10^2$ | 32/32 (100%) |
| 2 | S-HVT-062 | $1.5 \times 10^3$ | 22/22 (100%) |
| 2 | Controls | | 0/20 (0%) |
| 2 | HVT[c] | $7.5 \times 10^2$ | 17/21 (81%) |
| 2 | HVT/SB-1[c] | $7.5 \times 10^2$ | 21/22 (95%) |

[a]PFU/0.2 ml.
[b]No. protected/Total; Challenge 5 days post-vaccination.
[c]Commercial vaccine.

Example 11
Bivalent Vaccines Against Newcastle Disease and Marek's Disease

Recombinant HVT expressing proteins from NDV make bivalent vaccines protecting against both Marek's Disease and Newcastle disease. We have constructed several recombinant HVT expressing NDV proteins S-HVT-007 (example 11A), S-HVT-048 (example 11B), S-HVT-049 (example 1C), S-HVT-050 (example 1D), and S-HVT-106 (example 11E).

Example 11A
S-HVT-007

S-HVT-007 is a recombinant herpesvirus of turkeys that contains a hybrid E. coli lacZ NDV HN hybrid protein gene under the control of the PRV gX promoter and the NDV F gene under the control of the HSV-1 a 4 promoter inserted into the long unique region. The NDV genes are inserted in the same transcriptional orientation as the UL43 gene.

To construct S-HVT-007 HVT DNA and the plasmid 255-18.B16 were co-transfected according to the DNA TRANSFECTION FOR GENERATING RECOMBINANT VIRUS procedure into primary chick embryo fibroblast (CEF) cells. A blue virus obtained from the transfection stock was purified by successive plaque purifications using the BLUOGAL SCREEN FOR RECOMBINANT HERPESVIRUS procedure. At the end of this procedure, when 100% of the plaques were blue.

Example 11B
S-HVT-048

S-HVT-048 is a recombinant herpesvirus of turkeys that contains the MDV gB and gA genes and the NDV F gene under the control of the HCMV immediate early promoter inserted into the short unique region. The MDV and NDV genes are inserted in the same transcriptional orientation as the US2 gene.

S-HVT-048 was constructed according to the PROCEDURE FOR GENERATING RECOMBINANT HERPESVIRUS FROM SUBGENOMIC DNA FRAGMENTS. The following combination of subgenomic clones and enzymes were used: 407-32.2C3 with NotI, 172-07.BA2 with BamHI, 407-32.5G6 with NotI, 407-32.1C1 with NotI, 437-26.24 with BamHI and HindIII, 437-26.26 with BamHI and HindIII, and 535-70.3 uncut. Insertion of the appropriate DNA was confirmed by southern blot analysis.

Example 11C
S-HVT-049

S-HVT-049 is a recombinant herpesvirus of turkeys that contains the MDV gB and gA genes and the NDV HN gene under the control of the PRV gX promoter inserted into the short unique region. The MDV and NDV genes are inserted in the same transcriptentation as the US2 gene.

S-HVT-049 was constructed according to the PROCEDURE FOR GENERATING RECOMBINANT HERPESVIRUS FROM SUBGENOMIC DNA FRAGMENTS. The following combination of subgenomic clones and enzymes were used: 407-32.2C3 with NotI, 172-07.BA2 with BamHI, 407-32.5G6 with NotI, 407-32.1C1 with NotI, 437-26.24 with BamHI and HindIII, 437-26.26 with BamHI and HindIII, and 549-62.10 uncut. Insertion of the appropriate DNA was confirmed by southern blot analysis.

Example 11D
S-HVT-050

S-HVT-050 is a recombinant herpesvirus of turkeys that contains the MDV gB and gA genes and the NDV HN and F genes. The NDV genes are under the control of the PRV gX and HCMV immediately promoters respectively. All four genes are inserted into the short unique region in the same transcriptional orientation as the US2 gene.

S-HVT-050 was constructed according to the PROCEDURE FOR GENERATING RECOMBINANT HERPESVIRUS FROM SUBGENOMIC DNA FRAGMENTS. The following combination of subgenomic clones and enzymes were used: 407-32.2C3 with NotI, 172-07.BA2 with BamHI, 407-32.5G6 with NotI, 407-32.1C1 with NotI, 437-26.24 with BamHI and HindIII, 437-26.26 with BamHI and HindIII, and 549-24.15 uncut. Insertion of the appropriate DNA was confirmed by southern blot analysis. S-HVT-050 has been deposited pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A.

Example 11E
S-HVT-106

S-HVT-106 is a recombinant herpesvirus of turkeys that contains the MDV gA, gB, gD genes and the NDV HN and F genes. The NDV genes are under the control of the PRV gX and HCMV immediately promoters respectively. All five genes are inserted into the short unique region in the same transcriptional orientation as the US2 gene.

S-HVT-050 was constructed according to the PROCEDURE FOR GENERATING RECOMBINANT HERPESVIRUS FROM SUBGENOMIC DNA FRAGMENTS. The following combination of subgenomic clones and enzymes were used: 407-32.2C3 with NotI, 172-07.BA2 with BamHI, 407-32.5G6 with NotI, 407-32.1C1 with NotI, 437-26.24 with BamHI and HindIII, 437-26.26 with BamHI and HindIII, and 633-13.27 uncut.

Testing of Recombinant HVT Expressing NDV Antigens

Two studies were conducted to demonstrate the effectiveness of these recombinant HVT/MDV/NDV viruses in protecting against challenge with virulent Newcastle and Marek's disease viruses. In Study 1, one-day-old specific pathogen free (SPF) chicks were vaccinated with either S-HVT-048, S-HVT-049, S-HVT-050, or a USDA-licensed, conventional vaccine comprised of NDV B1/B1 virus. Three weeks post-vaccination, vaccinated chicks, and non-vaccinated, control chicks were challenged with NDV. Birds were then observed for clinical signs of disease. The results, in Table 8, show these recombinant viruses (S-HVT-048 and S-HVT-050) gave complete against a challenge that caused Newcastle disease in 100% of non-vaccinated control chicks. Recombinant virus S-HVT-049 gave partial protection against Newcastle disease.

In the second study, one-day-old chicks were vaccinated with S-HVT-050. Two more groups of chicks were vaccinated with a USDA-licensed, conventional vaccines comprised of HVT and a combination HVT and SB-1 viruses. Five days post-vaccination, the vaccinated chicks and a group of non-vaccinated, control chicks were challenged with MDV. The chicks were observed for 8 weeks for clinical signs of Marek's disease, then necropsied and observed for Marek's lesions. This study demonstrated the ability of S-HVT-050 to provide protection greater than the commercial Marek's disease vaccines.

TABLE 8

EFFICACY OF RECOMBINANT HVT/MDV/NDV VIRUSES
AGAINST VIRULENT NEWCASTLE AND
MAREK'S DISEASE VIRUS CHALLENGE

| Study | Vaccine Group | Dose[a] | Protection (%) NDV[b] | MDV[c] |
|---|---|---|---|---|
| 1 | S-HVT-048 | $4.0 \times 10^4$ | 19/19 (100) | |
| 1 | S-HVT-049 | $3.0 \times 10^4$ | 4/20 (20) | |
| 1 | S-HVT-050 | $1.5 \times 10^4$ | 20/20 (100) | |
| 1 | Controls | | 0/20 (0) | |
| 1 | NDV B1/B1[d] | | 18/18 (100) | |
| 2 | S-HVT-050 | $7.5 \times 10^2$ | | 13/14 (93) |
| 2 | S-HVT-050 | $1.5 \times 10^3$ | | 16/17 (94) |
| 2 | Controls | | | 5/23 (22) |
| 2 | HVT[d] | | | 20/26 (77) |
| 2 | HVT/SB-1[d] | | | 10/12 (83) |

[a]PFU/0.2 ml.
[b]No. protected/Total; Challenge 3 weeks post-vaccination.
[c]No. protected/Total; Challenge 5 days post-vaccination.
[d]Commercial vaccine.

Example 12
Bivalent Vaccines Against Infectious Laryngotracheitis and Marek's Disease Recombinant HVT expressing glycoproteins from ILT virus make bivalent vaccines protecting against both Marek's disease and infectious laryngotracheitis. We have constructed several recombinant HVT expressing ILT virus glycoproteins S-HVT-051 (example 12A), S-HVT-052 (example 12B), and S-HVT-104 (example 11C).

Example 12A
S-HVT-051

S-HVT-051 is a recombinant herpesvirus of turkeys that contains the ILT virus gB gene inserted into the short unique region. The ILT gene is inserted in the same transcriptional orientation as the US2 gene.

S-HVT-051 was constructed according to the PROCEDURE FOR GENERATING RECOMBINANT HERPESVIRUS FROM SUBGENOMIC DNA FRAGMENTS. The following combination of subgenomic clones and enzymes were used: 407-32.2C3 with NotI, 172-07.BA2 with BamHI, 407-32.5G6 with NotI, 407-32.1C1 with NotI, 437-26.24 with BamHI and HindIII, 437-26.26 with BamHI and HindIII, and 528-11.34 uncut. Insertion of the appropriate DNA was confirmed by southern blot analysis.

Example 12B
S-HVT-052

S-HVT-052 is a recombinant herpesvirus of turkeys that contains the ILT virus gD gene inserted into the short unique region. The ILT gene is inserted in the opposite transcriptional orientation as the US2 gene.

S-HVT-052 was constructed according to the PROCEDURE FOR GENERATING RECOMBINANT HERPESVIRUS FROM SUBGENOMIC DNA FRAGMENTS. The following combination of subgenomic clones and enzymes were used: 407-32.2C3 with NotI, 172-07.BA2 with BamHI, 407-32.5G6 with NotI, 407-32.1C1 with NotI, 437-26.24 with BamHI and HindIII, 437-26.26 with BamHI and HindIII, and 528-03.37 uncut. Insertion of the appropriate DNA was confirmed by southern blot analysis.

Example 12C
S-HVT-104

S-HVT-104 is a recombinant herpesvirus of turkeys that contains six foreign genes. The MDV gA, gB, and gD genes are inserted in the unique short region in the same transcriptional orientation as the US2 gene. An *E. coli* lacZ marker gene and the ILT gB and gD genes are inserted in BamHI #16 region in the same transcriptional orientation as the UL43 gene.

To construct S-HVT-104 DNA from S-HVT-062 and the plasmid 634-29.16 were co-transfected according to the DNA TRANSFECTION FOR GENERATING RECOMBINANT VIRUS procedure into primary chick embryo fibroblast (CEF) cells.

Testing of Recombinant HVT Expressing ILT Antigens

The following study was conducted to demonstrate the effectiveness of these recombinant HVT/ILT viruses in protecting against challenge with virulent Infectious Laryngotracheitis virus. One-day-old specific pathogen free (SPF) chicks were vaccinated with either S-HVT-051, S-HVT-052, a combination of S-HVT-051 and S-HVT-052, or a USDA-licensed, conventional vaccine comprised of ILT virus. Two to three weeks post-vaccination, vaccinated chicks, and non-vaccinated, control chicks were challenged with ILT. Birds were then observed for clinical signs of disease. The results, in Table 9, show these recombinant viruses (S-HVT-051 and S-HVT-052) gave protection against challenge with ILT virus comparable to a commercial ILT vaccine.

Animals vaccinated with the vaccines described here may be easily differentiated from animals infected with virulent ILT. This is accomplished by testing the suspect birds for antibodies to any ILT antigens other than gB or gD. Examples of such antigens are ILT glycoproteins C, E, and G. Vaccinated, uninfected birds will be negative for these antigens whereas infected birds will be positive.

TABLE 9

EFFICACY OF RECOMBINANT HVT/ILT VIRUSES
AGAINST VIRULENT INFECTIOUS
LARYNGOTRACHEITIS VIRUS CHALLENGE

| Vaccine Group | Dose[a] | Protection[b] |
|---|---|---|
| S-HVT-051 | $2.1 \times 10^3$ | 28/30 (93%) |
| S-HVT-052 | $1.7 \times 10^3$ | 29/29 (100%) |
| S-HVT-051 + | $2.1 \times 10^3$ | 24/24 (100%) |
| S-HVT-052 | $1.7 \times 10^3$ | |
| Controls | | 2/30 (7%) |
| ILT[c] | | 29/30 (97%) |

[a]PFU/0.2 ml.
[b]No. protected/Total; Challenge 2-3 weeks post-vaccination.
[c]Commercial vaccine.

Example 13
Bivalent Vaccines Against Infectious Bursal Disease and Marek's Disease Recombinant HVT expressing proteins from IBDV make bivalent vaccines protecting against both Marek's Disease and infectious bursal disease. We have constructed several recombinant HVT expressing IBDV proteins these viruses include S-HVT-003 (example 2) and S-HVT-096.

S-HVT-096 is a recombinant herpesvirus of turkeys that contains the IBDV VP2 gene, under the control of the HCMV immediate early promoter, inserted into the short unique region. The IBDV gene is inserted in the same transcriptional orientation as the US2 gene.

S-HVT-096 was constructed according to the PROCEDURE FOR GENERATING RECOMBINANT HERPESVIRUS FROM SUBGENOMIC DNA FRAGMENTS. The following combination of subgenomic clones and enzymes were used: 407-32.2C3 with NotI, 172-07.BA2 with BamHI, 407-32.5G6 with NotI, 407-32.1C1 with NotI, 437-26.24 with BamHI and HindIII, 556-60.6 with BamHI, and 602-57.F1 uncut. Insertion of the appropriate DNA was confirmed by southern blot analysis.

Testing of Recombinant HVT Expressing IBDV Antigens

S-HVT-096 was assayed for expression of VP2 by black plaque and western blot analysis. Both assays indicated that the virus was expressing high levels of protein which reacts specifically with an IBDV neutralizing monoclonal antibody. This virus will be useful as a vaccine against infectious bursal disease.

Example 14
Bivalent Vaccines Against Infectious Bronchitis and Marek's Disease

S-HVT-066 is a recombinant herpesvirus of turkeys that contains the MDV gB, gD and gA genes and the IBV spike and matrix genes. The IBV spike and matrix genes are under the control of the HCMV immediate early and PRV gX promoters respectively. All five genes are inserted into the short unique region. The MDV and IBV genes are inserted in the same transcriptional orientation as the US2 gene.

S-HVT-066 was constructed according to the PROCEDURE FOR GENERATING RECOMBINANT HERPESVIRUS FROM SUBGENOMIC DNA FRAGMENTS. The following combination of subgenomic clones and enzymes were used: 407-32.2C3 with NotI, 172-07.BA2 with BamHI, 407-32.5G6 with NotI, 407-32.1C1 with NotI, 437-26.24 with BamHI and HindIII, 556-60.6 with BamHI, and 567-72.1D uncut. Insertion of the appropriate DNA was confirmed by southern blot analysis.

Testing of Recombinant HVT Expressing IBV Antigens

S-HVT-066 was assayed for expression of the IBV spike protein by black plaque and western blot analysis. Both assays indicated that the virus was expressing high levels of protein which reacts specifically with an IBV neutralizing monoclonal antibody. This virus will be useful as a vaccine against infectious bronchitis.

Example 21
Vaccines utilizing HVT to express antigens from various pathogens

We also anticipate that antigens from the following pathogens may also be utilized to develop poultry vaccines: Chick anemia agent, Avian encephalomyelitis virus, Avian reovirus, Avian paramyxoviruses, Avian influenza virus, Avian adenovirus, Fowl pox virus, Avian coronavirus, Avian rotavirus, Salmonella spp E. coli, Pasteurella spp, Haemophilus spp, Chlamydia sppI Mycoplasma sppI Campylobacter spp, Bordetella spp, Poultry nematodes, cestodes, trematodes, Poultry mites/lice, Poultry protozoa (Eimeria spp, Histomonas spp, Trichomonas spp).

REFERENCES

1. Buckmaster et al., *J. Gen. Virol.* 69:2033, 1988.
2. F. A. Ferrari et al., *Journal of Bacteriology* 161, 556–562, 1985.
3. U. Gubler and B. J Hoffman, *Gene* 25, 263–269.
4. D. Hanahan, *Molecular Biology* 166, 557–580, 1983.
5. P. J. Hudson et al., *Nucleic Acid Research* 14, 5001–5012, 1986.
6. T. Igarashi et al., 10*th International Herpesvirus Workshop*, Abstract No. 17, Ann Arbor, Mich., August 1985.
7. T. Ihara et al., *Virus Genes* 3, 127–140, 1989.
8. M. A. Innis et al., *PCR Protocols A Guide to Methods and Applications*, 84–91, Academic Press, Inc., San Diego, 1990.
9. R. J. Isfort et al., 9*th International Herpesvirus Workshop*, Abstract No. 146, Seattle, Wash., August 1984.
10. M. N. Jagadish et al., *J. of Virol.* 62, 1084–1087, 1988.
11. Kawai and Nishizawa *Mol. and Cell Bio.* 4, 1172–1174, 1984.
12. B. Lomniczi et al., *Journal of Virology* 49, 970–979 1984.
13. Maniatis et al., *Molecular Cloning,* Cold Spring Harbor Laboratory, New York, 1982.
14. D. J. McGeoch et al., *Journal of Molecular Biology* 181, 1–13, 1985.
15. S. L. McKnight and R. Kingsbury, *Science* 217, 316–324, 1982.
16. L. J. N. Ross et al., *Journal of General Virology* 70, 1789–1804, 1989.
17. L. J. N. Ross et al., *Journal of General Virology* 72, 949–954, 1991.
18. J. Sambrook et al., *Molecular Cloning A Laboratory Manual Second Edition,* Cold Spring Harbor Press, 1989.
19. M. Zijil et al., *Journal of Virology* 62, 2191–2195, 1988.
20. Maniatis et al., *Intervirology* 16, 201–217, 1981.
21. S. L. Mansour et al., *Proc. Natl. Acad. Sci. USA* 82, 1359–1363, 1985.
22. C. Thummel et al., *Cell* 33, 455–464, 1983.
23. D. Scolnick, *Cell* 24, 135–143, 1981.
24. C. Thummel et al., *Cell* 23, 825–836, 1981.
25. Y. Haj-Ahmed and F. L. Graham, *J. of Virology* 57, 267–274, 1986.
26. M. Mackett et al., *Proc. Natl. Acad. Sci. USA* 79, 7415–7419, 1982.
27. D. Panicali and E. Paoletti, *Proc. Natl. Acad. Sci. USA* 79, 4927–4931, 1982.
28. E. Paoletti et al., *Proc. Natl. acad. Sci. USA* 81, 193–197, 1984.
29. G. L. Smith et al., *Nature* 302, 490–495, 1983.
30. J. H. Gillespie et al., *J. Clin. Microbiology* 23, 283–288, 1986.
31. D. Panicali et al., *Proc. Natl. Acad. Sci. USA* 80, 5364–5368, 1983.
32. G. L. Smith et al., *Proc. Natl. Acad. Sci. USA* 80, 7155–7159, 1983.
33. G. L. Smith et al., *Science* 224, 397–399, 1984.
34. M. Mackett et al., *Science* 227, 433–435, 1985.
35. E. S. Moccarski et al., *Cell* 22, 243–255, 1980.
40. L. E. Post and B. Roizman, *Cell* 25, 227–232, 1981.
41. K. L. Poffenberger et al., *Proc. Natl. Acad. Sci. USA* 80, 2690–2694, 1981.
42. M. G. Gibson and P. G. Spear, *Journal of Virology* 48, 396–404, 1983.
43. G. T.-Y. Lee et al., *Proc. Natl. Acad. Sci. USA* 79, 6612–6616, 1982.
44. M.-F. Shih et al., *Proc. Natl. Acad. Sci. USA* 81, 5867–5870, 1984.
45. R. Desrosiers et al., *Ninth Annual Herpesvirus Meeting, Seattle,* Abstract #280, 1984.
46. M. Arsenakis and B. Roizman, in "The High Technology Route to Virus Vaccines", American Society for Microbiology, Washington D.C., 1985 (Proceedings of the First Annual Southwest Foundation for Biomedical Research International Symposium, Houston, Tex., 8–10 November 1984).
47. L. E. Post et al., *Tenth International Herpesvirus Workshop,* Ann Arbor, August 1985.
48. S. B. Mohanty and S. K. Dutta, *Veterinary Virology,* Lea and Febiger, pubs., Philadelphia, 1981.
49. A. M. Griffin, *Journal of General Virology* 72, 393–398, 1991.
50. D. R. Thomsen et al., *Gene* 16, 207–217, 1981.

What is claimed:

1. A recombinant herpesvirus of turkeys designated S-HVT-062 (ATCC Accession No. VR 2401).

2. A vaccine which comprises an effective immunizing amount of the recombinant herpesvirus of turkeys of claim 1 and a suitable carrier.

3. The vaccine of claim 2, wherein the suitable carrier is a physiologically balanced culture medium containing stabilizing agents.

4. The vaccine of claim 2, wherein the effective immunizing amount is from about $10^2$ to about $10^9$ PFU/dose.

5. A method of immunizing a fowl against Marek's disease virus which comprises administering to the fowl an effective immunizing dose of the vaccine of claim 2.

6. The method of claim 5, wherein the vaccine is administered by intramuscular, subcutaneous, intraperitoneal, or intravenous injection.

7. The method of claim 5, wherein the vaccine is administered intranasally, intraocularly, or orally.

* * * * *